(12) United States Patent
Blium et al.

(10) Patent No.: US 11,426,628 B2
(45) Date of Patent: Aug. 30, 2022

(54) SYSTEM AND METHOD FOR IDENTIFYING AND CORRECTING MUSCULAR AND SKELETAL DISBALANCES THROUGH EXERCISE

(71) Applicants: Elena Balkarova, Malaga (ES); Jevgenij Blium, Malaga (ES)

(72) Inventors: Jevjenij Blium, Malaga (ES); Elena Balkarova, Malaga (ES); Alexey Popyrin, Ventimiglia (IT)

( * ) Notice: Subject to any disclaimer, the term of this patent is extended or adjusted under 35 U.S.C. 154(b) by 0 days.

(21) Appl. No.: 15/954,834

(22) Filed: Apr. 17, 2018

(65) Prior Publication Data
US 2018/0296879 A1  Oct. 18, 2018

Related U.S. Application Data

(63) Continuation of application No. 62/486,131, filed on Apr. 17, 2017.

(51) Int. Cl.
*A63B 24/00* (2006.01)
*A63B 21/06* (2006.01)
(Continued)

(52) U.S. Cl.
CPC .......... *A63B 24/0062* (2013.01); *A61B 5/002* (2013.01); *A61B 5/1036* (2013.01);
(Continued)

(58) Field of Classification Search
CPC ............ A63B 24/0062; A63B 21/4003; A63B 21/4034; A63B 21/4039; A63B 21/0615;
(Continued)

(56) References Cited

U.S. PATENT DOCUMENTS 7,658,695 B1 * 2/2010 Amsbury ........... A63B 24/0021
434/247
7,708,669 B2  5/2010 Rodgers, Jr.
(Continued)

FOREIGN PATENT DOCUMENTS

RU         141826 U1    6/2014
RU         141828 U1    6/2014
(Continued)

*Primary Examiner* — Daniel L Cerioni
(74) *Attorney, Agent, or Firm* — Michael D. Eisenberg

(57) ABSTRACT

A method for identifying and correcting muscular and skeletal disbalances through exercise includes recording, by a processor, using at least one sensor coupled to the processor, an exercise motion performed by a user, identifying, by the processor, a motion deficiency of the user based on the detected exercise motion, formulating, by the processor, a corrective motion based on the detected motion deficiency, and providing, by the processor, the corrective motion to the user, which also includes identifying motion deficiencies as far as range of motion, balance, symmetry, smoothness, strength, stamina and other motion characteristics, formulating corrective exercise program that involves multiple training machines, formulating exercises in terms of number of repetitions, cadence (frequency) or motion, range of motion, added resistance levels, communicating the corrective exercise program via the screen embedded on each machine, and guiding the user through each exercise, directing user to change exercise machines.

21 Claims, 35 Drawing Sheets
(26 of 35 Drawing Sheet(s) Filed in Color)

400

Recording, by an Exercise Device Comprising a Frame and a Pendulum having a Proximal End Journaled on the Frame and a Distal End, Using at Least One Sensor, an Exercise Motion Comprising the User Moving the Pendulum
401

↓

Identifying, by the Exercise Device, a Health Deficit of the User Based on the Detected Exercise Motion
402

(51) Int. Cl.

| | | |
|---|---|---|
| *A63B 21/00* | (2006.01) | |
| *A61B 5/00* | (2006.01) | |
| *A61B 5/103* | (2006.01) | |
| *A61B 5/11* | (2006.01) | |
| *A63B 21/062* | (2006.01) | |
| *A63B 23/02* | (2006.01) | |
| *A63B 71/06* | (2006.01) | |

(52) U.S. Cl.
CPC .......... *A61B 5/1123* (2013.01); *A61B 5/4519* (2013.01); *A61B 5/486* (2013.01); *A61B 5/742* (2013.01); *A63B 21/062* (2013.01); *A63B 21/0615* (2013.01); *A63B 21/0616* (2015.10); *A63B 21/4003* (2015.10); *A63B 21/4034* (2015.10); *A63B 21/4039* (2015.10); *A63B 23/0244* (2013.01); *A63B 71/0622* (2013.01); *A63B 71/0669* (2013.01); *A63B 71/0686* (2013.01); *A61B 2562/0219* (2013.01); *A61B 2562/0247* (2013.01); *A63B 23/0205* (2013.01); *A63B 23/0211* (2013.01); *A63B 23/0216* (2013.01); *A63B 23/0233* (2013.01); *A63B 2024/0009* (2013.01); *A63B 2024/0012* (2013.01); *A63B 2024/0015* (2013.01); *A63B 2024/0068* (2013.01); *A63B 2071/063* (2013.01); *A63B 2071/068* (2013.01); *A63B 2071/0641* (2013.01); *A63B 2071/0652* (2013.01); *A63B 2220/10* (2013.01); *A63B 2220/12* (2013.01); *A63B 2220/24* (2013.01); *A63B 2220/40* (2013.01); *A63B 2220/51* (2013.01); *A63B 2220/52* (2013.01); *A63B 2220/54* (2013.01); *A63B 2220/56* (2013.01); *A63B 2220/72* (2013.01); *A63B 2220/802* (2013.01); *A63B 2220/803* (2013.01); *A63B 2220/806* (2013.01); *A63B 2220/807* (2013.01); *A63B 2220/808* (2013.01); *A63B 2220/833* (2013.01); *A63B 2225/09* (2013.01); *A63B 2225/096* (2013.01); *A63B 2225/102* (2013.01); *A63B 2225/15* (2013.01); *A63B 2225/20* (2013.01); *A63B 2225/54* (2013.01); *A63B 2230/06* (2013.01); *A63B 2230/60* (2013.01)

(58) Field of Classification Search
CPC ..... A61B 5/002; A61B 5/1036; A61B 5/1123; A61B 5/4519; A61B 5/486; A61B 5/742
USPC .......................................................... 600/592
See application file for complete search history.

(56) References Cited

U.S. PATENT DOCUMENTS

| | | | |
|---|---|---|---|
| 7,922,622 B2 | 4/2011 | Holle | |
| 8,608,623 B2 | 12/2013 | Lee | |
| 8,784,115 B1* | 7/2014 | Chuang | A61B 5/486 |
| | | | 434/236 |
| 8,979,709 B2 | 3/2015 | Toback et al. | |
| 9,101,791 B2 | 8/2015 | Boyette | |
| 9,168,418 B2 | 10/2015 | Adamchick et al. | |
| 9,233,275 B2 | 1/2016 | Gatherer | |
| 9,283,429 B2 | 3/2016 | Aragones et al. | |
| 9,289,674 B2 | 3/2016 | Winsper et al. | |
| 9,295,422 B2 | 3/2016 | Tai | |
| 9,546,871 B2 | 1/2017 | Ellis et al. | |
| 2008/0242521 A1* | 10/2008 | Einav | A61B 5/1116 |
| | | | 482/110 |
| 2010/0023293 A1* | 1/2010 | Walthert | G01G 23/3735 |
| | | | 702/101 |
| 2012/0100963 A1* | 4/2012 | Gordon | A61H 1/0237 |
| | | | 482/52 |
| 2013/0072352 A1 | 3/2013 | Jung et al. | |
| 2013/0209979 A1 | 8/2013 | Mihelj et al. | |
| 2014/0074265 A1 | 3/2014 | Arginsky et al. | |
| 2015/0269426 A1 | 9/2015 | Suzuki et al. | |
| 2017/0000386 A1* | 1/2017 | Salamatian | A61B 5/742 |

FOREIGN PATENT DOCUMENTS

| | | |
|---|---|---|
| RU | 141961 U1 | 6/2014 |
| WO | 0218019 A1 | 3/2002 |
| WO | 2015113162 A1 | 8/2015 |

* cited by examiner

400

Recording, by an Exercise Device Comprising a Frame and a Pendulum having a Proximal End Journaled on the Frame and a Distal End, Using at Least One Sensor, an Exercise Motion Comprising the User Moving the Pendulum
401

Identifying, by the Exercise Device, a Health Deficit of the User Based on the Detected Exercise Motion
402

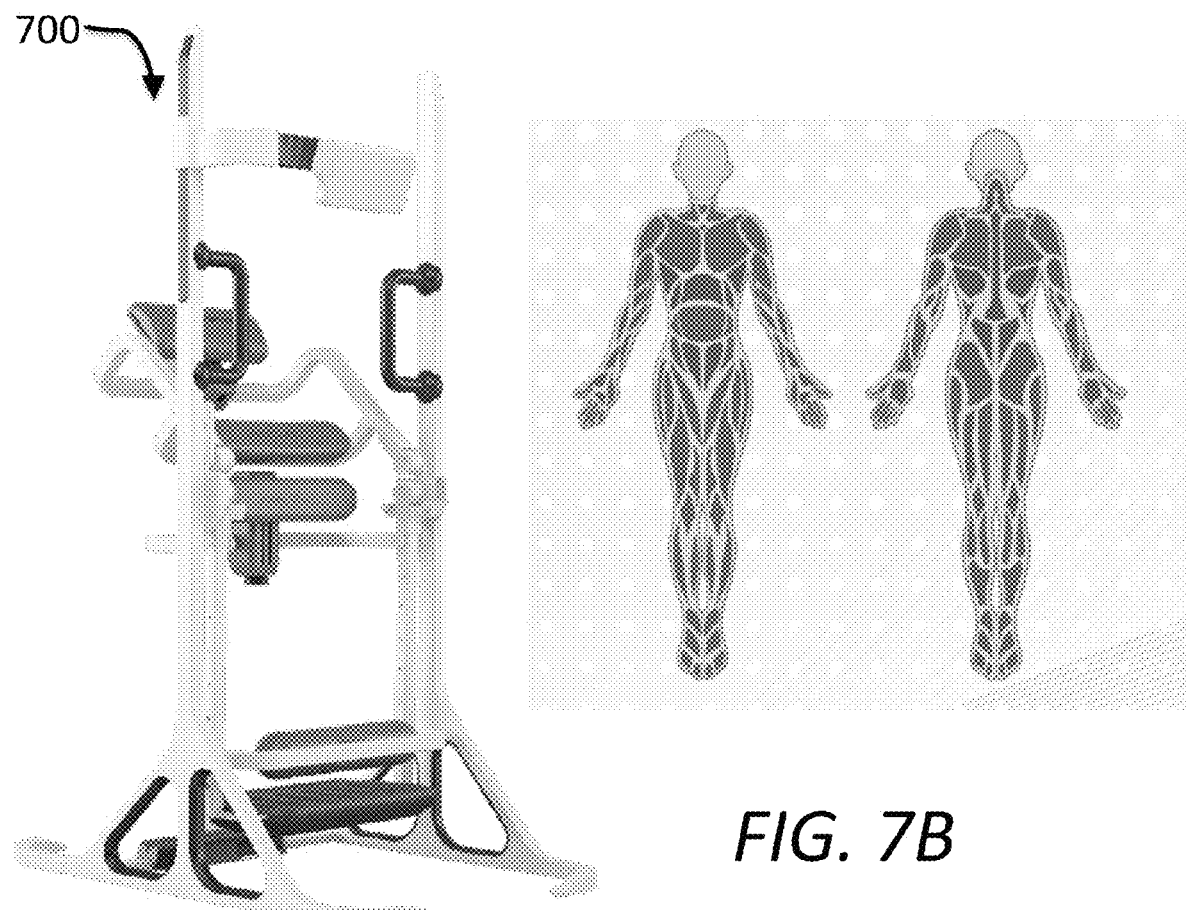
FIG. 7A
FIG. 7B
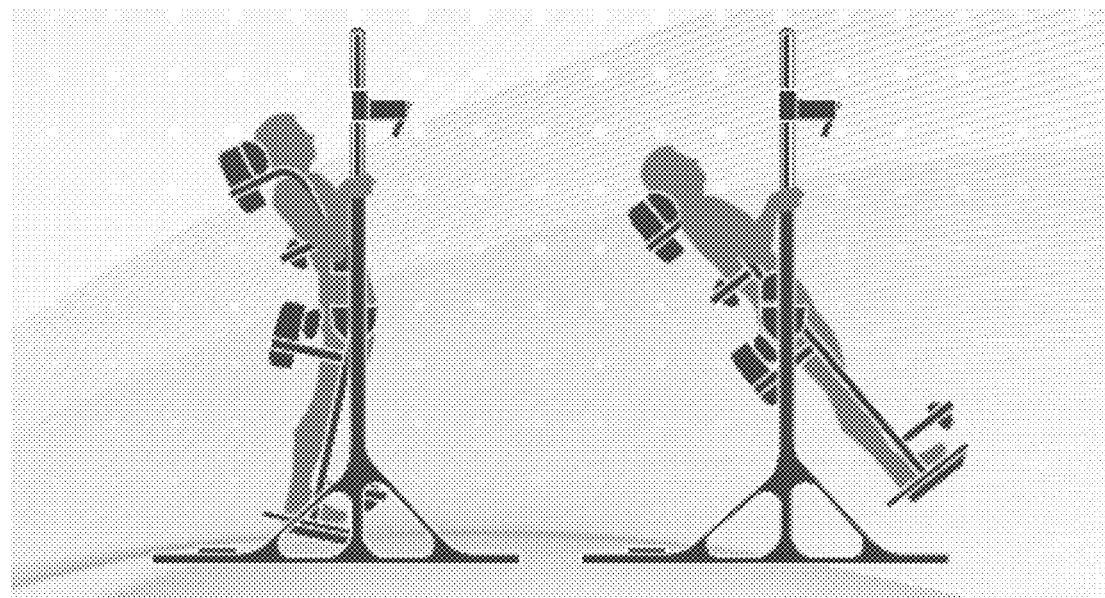
FIG. 7C

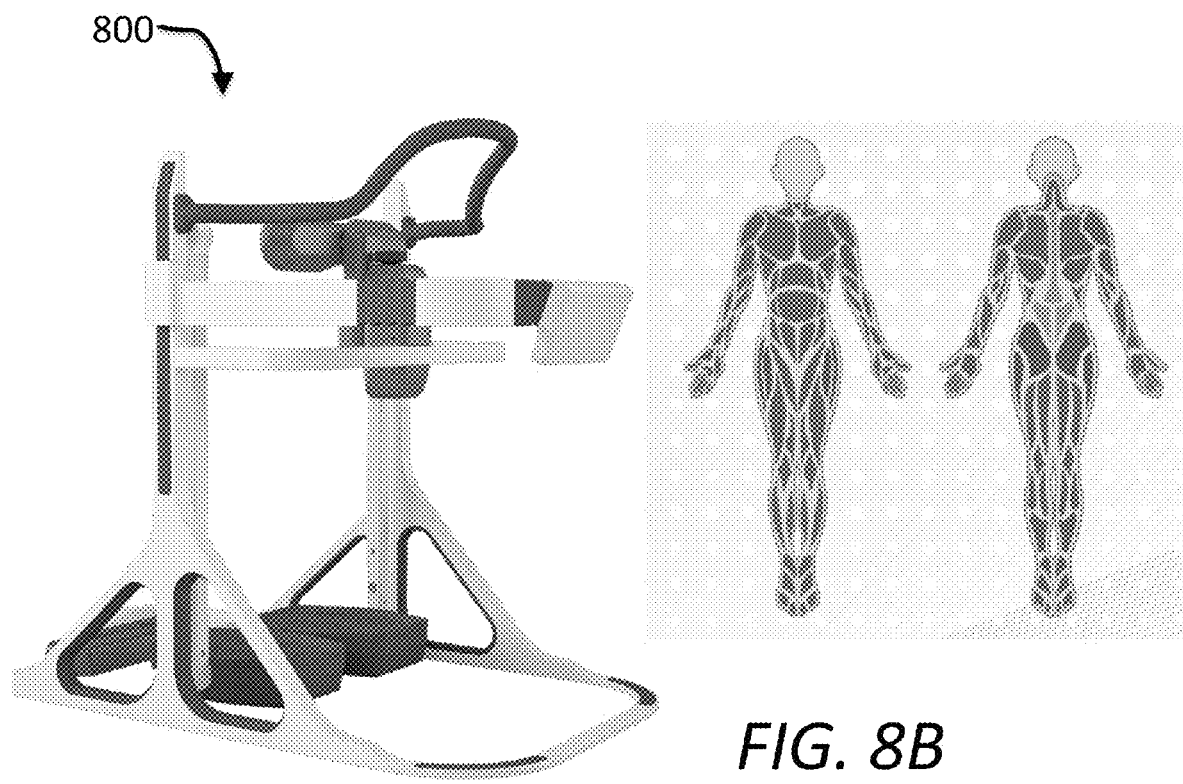
FIG. 8A
FIG. 8B
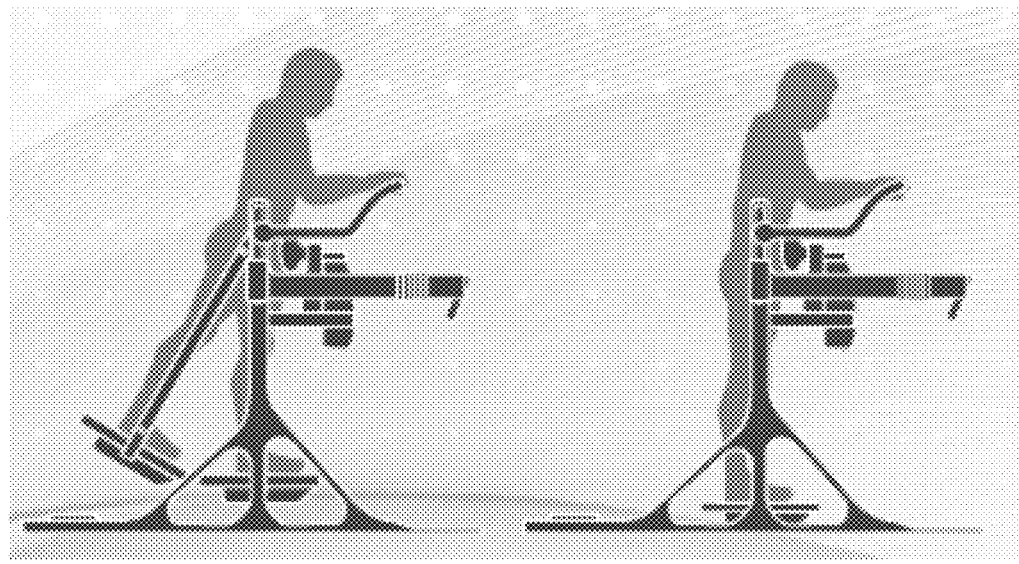
FIG. 8C

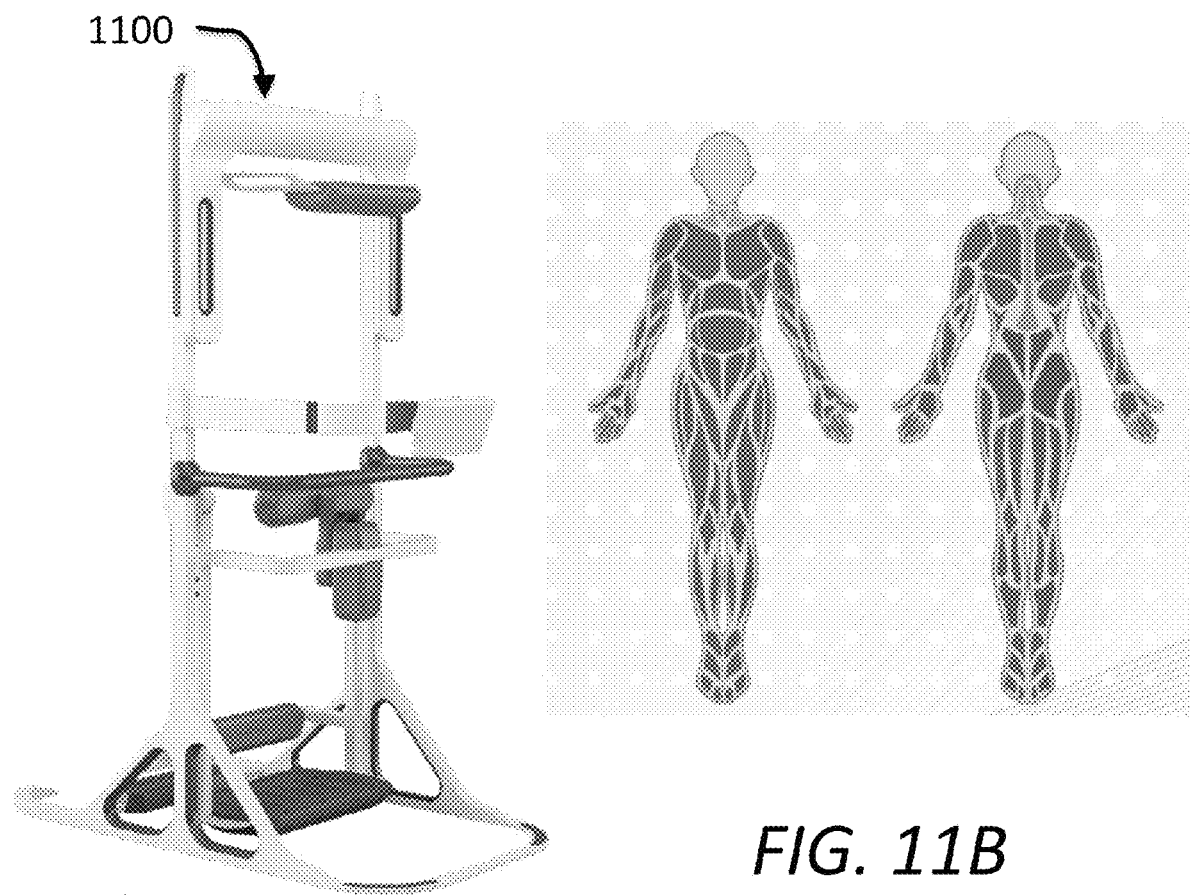
FIG. 11A
FIG. 11B
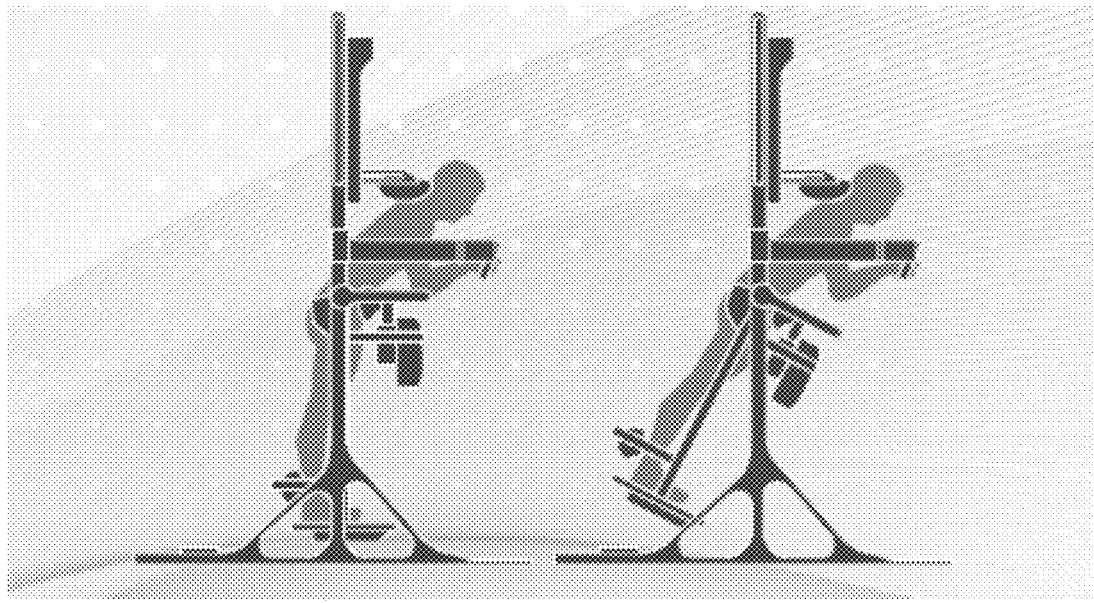
FIG. 11C

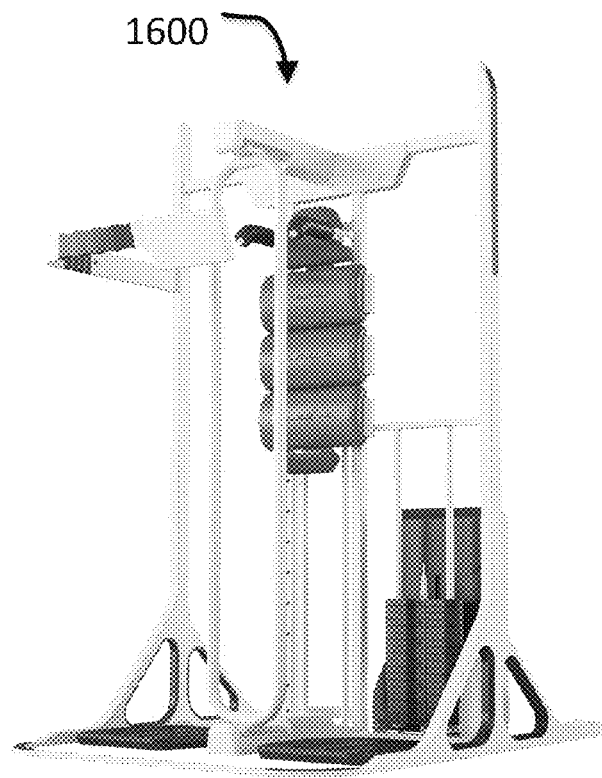
FIG. 16A
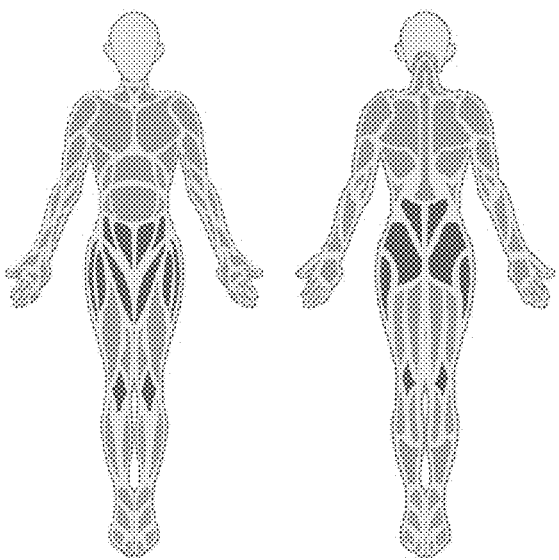
FIG. 16B
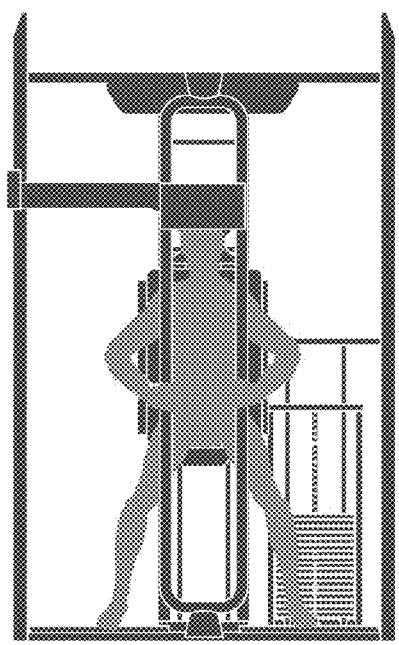
FIG. 16C
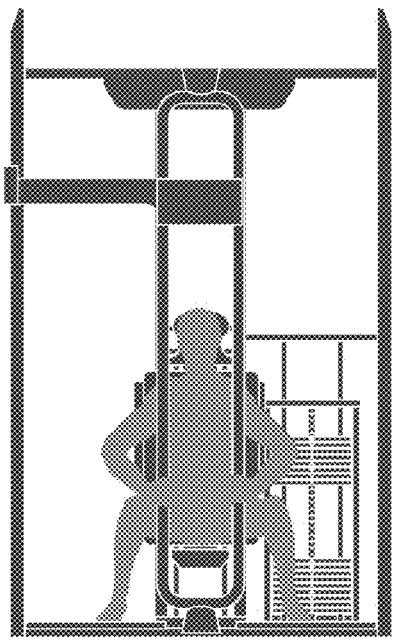

SYSTEM AND METHOD FOR IDENTIFYING AND CORRECTING MUSCULAR AND SKELETAL DISBALANCES THROUGH EXERCISE

TECHNICAL FIELD

This invention relates to exercise equipment and methods for the use of exercise equipment. More particularly, the present invention relates to identifying and correcting motion through exercise.

BACKGROUND ART

The importance of physical fitness for overall health has never been greater. As health care becomes more complex and expensive, the value of preventative care increases, and with it the value of a more balanced and active lifestyle. Regular exercise has been shown to reduce the risk of various illnesses, particularly those associated with weight gain and sedentary tendencies. However, many people who could benefit from exercise suffer from physical issues that prevent them from reaching their potential. These issues, ranging from deficient core strength and unbalanced physiques to spinal and joint problems, can prevent many people from getting the exercise they need for optimal health. Moreover, some issues can have severe health impacts of their own if left uncorrected; for instance, people with core strength deficiencies may be more likely to suffer a severe fall as they age. Trainers and physical therapists can help to correct these problems, but are expensive to employ and still rely on their patients to exercise at home between sessions. In many cases, people lack the expertise and motivation to follow their assigned exercise routines.

In view of the above, there is a need for an inexpensive and accurate way to identify motion deficiencies, formulate corrective measures, and assist users in performing those corrective measures to alleviate the identified deficiencies.

SUMMARY OF THE EMBODIMENTS

The present invention provides a system for identifying and correcting motion deficiencies through exercise. The system includes a frame, a pendulum having a proximal end journaled on the frame and a distal end, a platform at the distal end of the pendulum, the platform sized to accommodate both feet of a user, and at least one sensor configured to sense an exercise motion performed by a user standing on the platform.

In some instances, a sensor can include at least one pressure sensor. A pressure sensor can include two pressure sensors. The sensor can be incorporated into the platform. The sensor can include one or more motion sensors. The motion sensor can be incorporated in the pendulum. The motion sensor can include at least one accelerometer or at least one gyroscope.

According to one embodiment of the present invention, the system can include a processor coupled to the at least one sensor, the processor configured to record, using the at least one sensor, an exercise motion performed by a user, to identify a motion deficiency of the user based on the detected exercise motion, to formulate a corrective motion based on the detected motion deficiency, and to provide the corrective motion to the user.

In some instances, the system can include a wireless identification device, which can include a near-field communication reader. The system can also include a display coupled to one or more sensors. The system can include one or more support cushions attached to the pendulum or the frame. In some embodiments, the support cushion can be attached to an adjustment mechanism that is configured to modify a distance of the at least one support cushion from the at least one of the frame, the platform, or the pendulum. In some instances the adjustment mechanism is electrical.

A method for identifying and correcting motion deficiencies through exercise using the system of the present invention is also disclosed. The method includes the steps of recording, by a processor, using at least one sensor coupled to the processor, an exercise motion performed by a user, identifying, by the processor, a motion deficiency of the user based on the detected exercise motion, formulating, by the processor, a corrective motion based on the detected motion deficiency, and providing, by the processor, the corrective motion to the user.

In some instances, recording the exercise motion can include recording the user swinging a pendulum through an arc, or recording the user performing a squat, or recording pressure applied by the user on at least one pressure sensor. The method can include recording distribution of pressure between two limbs of the user during the exercise motion, and in some instances, recording an acceleration of the exercise motion, or recording a change in orientation of the exercise motion.

Other aspects, embodiments and features of the device and method will become apparent from the following detailed description when considered in conjunction with the accompanying figures. The accompanying figures are for schematic purposes and are not intended to be drawn to scale. In the figures, each identical or substantially similar component that is illustrated in various figures is represented by a single numeral or notation. For purposes of clarity, not every component is labeled in every figure. Nor is every component of each embodiment of the device and method shown where illustration is not necessary to allow those of ordinary skill in the art to understand the device and method.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description of the disclosed system and method will be better understood when read in conjunction with the attached drawings. For the purpose of illustrating the system and method, presently preferred embodiments are shown in the drawings. It should be understood, however, that neither the system nor the method is limited to the precise arrangements and instrumentalities shown.

FIG. 7A is a schematic diagram of an embodiment of the disclosed system;

FIG. 7B is a schematic diagram showing body segments that can be targeted using the embodiment of FIG. 7A;

FIG. 7C is a schematic diagram showing the embodiment of FIG. 7A in action;

FIG. 8A is a schematic diagram of an embodiment of the disclosed system;

FIG. 8B is a schematic diagram showing body segments that can be targeted using the embodiment of FIG. 8A;

FIG. 8C is a schematic diagram showing the embodiment of FIG. 8A in action;

FIG. 11A is a schematic diagram of an embodiment of the disclosed system;

FIG. 11B is a schematic diagram showing body segments that can be targeted using the embodiment of FIG. 11A;

FIG. 11C is a schematic diagram showing the embodiment of FIG. 11A in action;

FIG. 16A is a schematic diagram of an embodiment of the disclosed system;

FIG. 16B is a schematic diagram showing body segments that can be targeted using the embodiment of FIG. 16A;

FIG. 16C is a schematic diagram showing the embodiment of FIG. 16A in action;

DETAILED DESCRIPTION OF SPECIFIC EMBODIMENTS

Figure 1A:
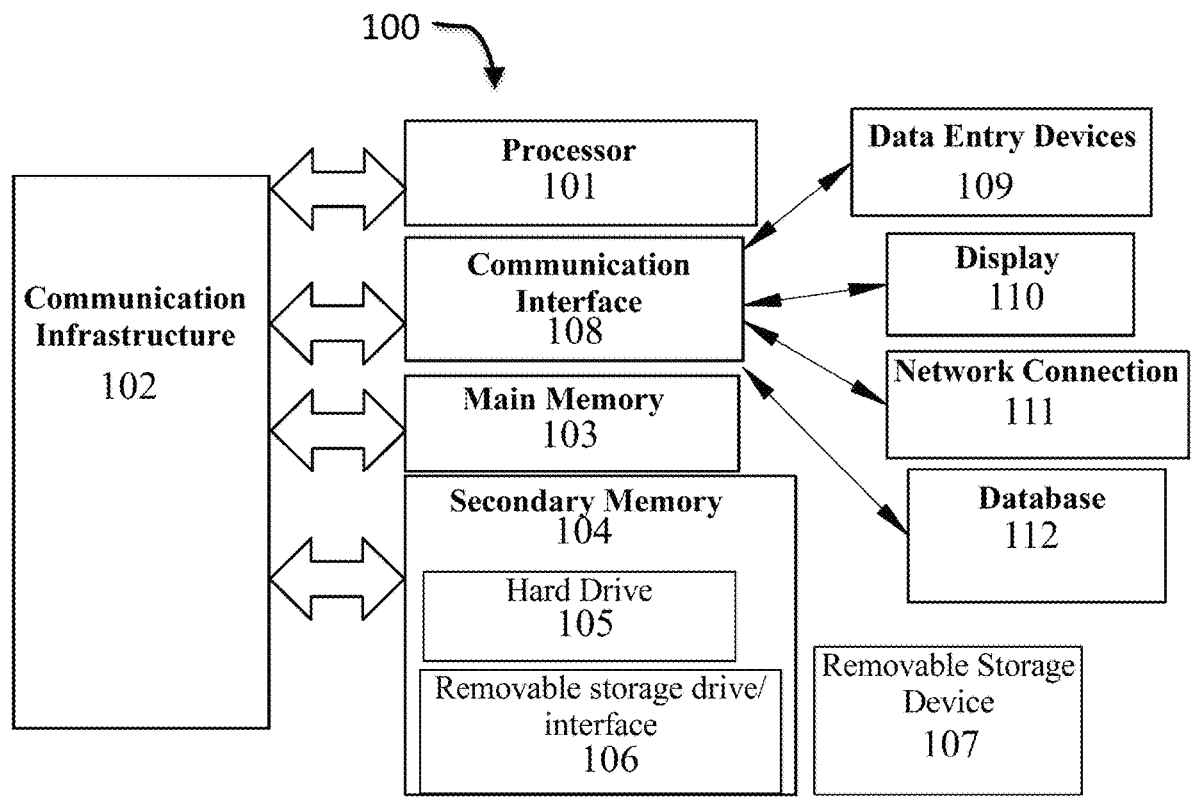
FIG. 1A is a schematic diagram depicting an example of a computing device as described herein.

Some embodiments of the disclosed system and methods will be better understood by reference to the following comments concerning computing devices. A "computing device" may be defined as including personal computers, laptops, tablets, smart phones, and any other computing device capable of supporting an application as described herein. The system and method disclosed herein will be better understood in light of the following observations concerning the computing devices that support the disclosed application, and concerning the nature of web applications in general. An exemplary computing device is illustrated by FIG. 1A. The processor 101 may be a special purpose or a general-purpose processor device. As will be appreciated by persons skilled in the relevant art, the processor device 101 may also be a single processor in a multi-core/multiprocessor system, such system operating alone, or in a cluster of computing devices operating in a cluster or server farm. The processor 101 is connected to a communication infrastructure 102, for example, a bus, message queue, network, or multi-core message-passing scheme. In some embodiments, the processor 101 includes a central processing unit (CPU), which performs arithmetic, memory exchange, and logical operations in response to instructions entered from memory or input-output devices, described in further detail below. The processor 101 may include a plurality of CPUs. The processor 101 may include a graphical processing unit (GPU), which is a circuit designed to process memory in a manner that optimizes the manipulation of computer graphics; the GPU may be able to perform many tasks simultaneously through extensive parallel processing.

The computing device also includes a main memory 103, such as random access memory (RAM), and may also include a secondary memory 104. Secondary memory 104 may include, for example, a hard disk drive 105, a removable storage drive or interface 106, connected to a removable storage unit 107, or other similar means. As will be appreciated by persons skilled in the relevant art, a removable storage unit 107 includes a computer usable storage medium having stored therein computer software and/or data. Examples of additional means creating secondary memory 104 may include a program cartridge and cartridge interface (such as that found in video game devices), a removable memory chip (such as an EPROM, or PROM) and associated socket, and other removable storage units 107 and interfaces 106 which allow software and data to be transferred from the removable storage unit 107 to the computer system. In some embodiments, to "maintain" data in the memory of a computing device means to store that data in that memory in a form convenient for retrieval as required by the algorithm at issue, and to retrieve, update, or delete the data as needed.

The computing device may also include a communications interface 108. The communications interface 108 allows software and data to be transferred between the computing device and external devices. The communications interface 108 may include a modem, a network interface (such as an Ethernet card), a communications port, a PCMCIA slot and card, or other means to couple the computing device to external devices. Software and data transferred via the communications interface 108 may be in the form of signals, which may be electronic, electromagnetic, optical, or other signals capable of being received by the communications interface 108. These signals may be provided to the communications interface 108 via wire or cable, fiber optics, a phone line, a cellular phone link, and radio frequency link or other communications channels. Other devices may be coupled to the computing device 100 via the communications interface 108. In some embodiments, a device or component is "coupled" to a computing device 100 if it is so related to that device that the product or means and the device may be operated together as one machine. In particular, a piece of electronic equipment is coupled to a computing device if it is incorporated in the computing device (e.g. a built-in camera on a smart phone), attached to the device by wires capable of propagating signals between the equipment and the device (e.g. a mouse connected to a personal computer by means of a wire plugged into one of the computer's ports), tethered to the device by wireless technology that replaces the ability of wires to propagate signals (e.g. a wireless BLUETOOTH® headset for a mobile phone), or related to the computing device by shared membership in some network consisting of wireless and wired connections between multiple machines (e.g. a printer in an office that prints documents to computers belonging to that office, no matter where they are, so long as they and the printer can connect to the internet). A computing device 100 may be coupled to a second computing device (not shown); for instance, a server may be coupled to a client device, as described below in greater detail.

The communications interface in the system embodiments discussed herein facilitates the coupling of the computing device with data entry devices 109, the device's display 110, and network connections, whether wired or wireless 111. In some embodiments, "data entry devices" 109 are any equipment coupled to a computing device that may be used to enter data into that device. This definition includes, without limitation, keyboards, computer mice, touchscreens, digital cameras, digital video cameras, wireless antennas, Global Positioning System devices, audio input and output devices, gyroscopic orientation sensors, proximity sensors, compasses, scanners, specialized reading devices such as fingerprint or retinal scanners, and any hardware device capable of sensing electromagnetic radiation, electromagnetic fields, gravitational force, electromagnetic force, temperature, vibration, or pressure. A computing device's "manual data entry devices" is the set of all data entry devices coupled to the computing device that permit the user to enter data into the computing device using manual manipulation. Manual entry devices include without limitation keyboards, keypads, touchscreens, track-pads, computer mice, buttons, and other similar components. A computing device may also possess a navigation facility. The computing device's "navigation facility" may be any facility coupled to the computing device that enables the device accurately to calculate the device's location on the surface of the Earth. Navigation facilities can include a receiver configured to communicate with the Global Positioning System or with similar satellite networks, as well as any other system that mobile phones or other devices use to ascertain their location, for example by communicating with cell towers.

In some embodiments, a computing device's "display" 110 is a device coupled to the computing device, by means of which the computing device can display images. The Display 210 may include without limitation monitors, screens, television devices, and projectors.

Computer programs (also called computer control logic) are stored in main memory 103 and/or secondary memory 104. Computer programs may also be received via the communications interface 108. Such computer programs, when executed, enable the processor device 101 to implement the system embodiments discussed below. Accordingly, such computer programs represent controllers of the system. Where embodiments are implemented using software, the software may be stored in a computer program product and loaded into the computing device using a removable storage drive or interface 106, a hard disk drive 105, or a communications interface 108.

The computing device may also store data in database 112 accessible to the device. A database 112 is any structured collection of data. As used herein, databases can include "NoSQL" data stores, which store data in a few key-value structures such as arrays for rapid retrieval using a known set of keys (e.g. array indices). Another possibility is a relational database, which can divide the data stored into fields representing useful categories of data. As a result, a stored data record can be quickly retrieved using any known portion of the data that has been stored in that record by searching within that known datum's category within the database 112, and can be accessed by more complex queries, using languages such as Structured Query Language, which retrieve data based on limiting values passed as parameters and relationships between the data being retrieved. More specialized queries, such as image matching queries, may also be used to search some databases. A database can be created in any digital memory. A database may be stored on a single computing device, or distributed between two or more computing devices. A database may be stored in a cloud service, or may be stored in part locally and in part in the cloud.

Persons skilled in the relevant art will also be aware that while any computing device must necessarily include facilities to perform the functions of a processor 101, a communication infrastructure 102, at least a main memory 103, and usually a communications interface 108, not all devices will necessarily house these facilities separately. For instance, in some forms of computing devices as defined above, processing 101 and memory 103 could be distributed through the same hardware device, as in a neural net, and thus the communications infrastructure 102 could be a property of the configuration of that particular hardware device. Many devices do practice a physical division of tasks as set forth above, however, and practitioners skilled in the art will understand the conceptual separation of tasks as applicable even where physical components are merged. Computing devices as described herein include any device that may be described as above, including without limitation single board "system on chip" devices, microcontrollers, smartphones, tablets, laptops, desktop computers, mainframes, servers, and data center machines.

The computing device 100 may employ one or more security measures to protect the computing device 100 or its data. For instance, the computing device 100 may protect data using a cryptographic system. In one embodiment, a cryptographic system is a system that converts data from a first form, known as "plaintext," which is intelligible when viewed in its intended format, into a second form, known as "cyphertext," which is not intelligible when viewed in the same way. The cyphertext is may be unintelligible in any format unless first converted back to plaintext. In one embodiment, the process of converting plaintext into cyphertext is known as "encryption." The encryption process may involve the use of a datum, known as an "encryption key," to alter the plaintext. The cryptographic system may also convert cyphertext back into plaintext, which is a process known as "decryption." The decryption process may involve the use of a datum, known as a "decryption key," to return the cyphertext to its original plaintext form. In embodiments of cryptographic systems that are "symmetric," the decryption key is essentially the same as the encryption key: possession of either key makes it possible to deduce the other key quickly without further secret knowledge. The encryption and decryption keys in symmetric cryptographic systems may be kept secret, and shared only with persons or entities that the user of the cryptographic system wishes to be able to decrypt the cyphertext. One example of a symmetric cryptographic system is the Advanced Encryption Standard ("AES"), which arranges plaintext into matrices and then modifies the matrices through repeated permutations and arithmetic operations with an encryption key.

In embodiments of cryptographic systems that are "asymmetric," either the encryption or decryption key cannot be readily deduced without additional secret knowledge, even given the possession of the corresponding decryption or encryption key, respectively; a common example is a "public key cryptographic system," in which possession of the encryption key does not make it practically feasible to deduce the decryption key, so that the encryption key may safely be made available to the public. An example of a public key cryptographic system is RSA, in which the encryption key involves the use of numbers that are products of very large prime numbers, but the decryption key involves the use of those very large prime numbers, such that deducing the decryption key from the encryption key requires the practically infeasible task of computing the prime factors of a number which is the product of two very large prime numbers. Another example is elliptic curve cryptography, which relies on the fact that given two points P and Q on an elliptic curve over a finite field, and a definition for addition where A+B=R, the point where a line connecting point A and point B intersects the elliptic curve, where "0," the identity, is a point at infinity in a projective plane containing the elliptic curve, finding a number k such that adding P to itself k times results in Q is computationally impractical, given correctly selected elliptic curve, finite field, and P and Q.

Figure 1B:
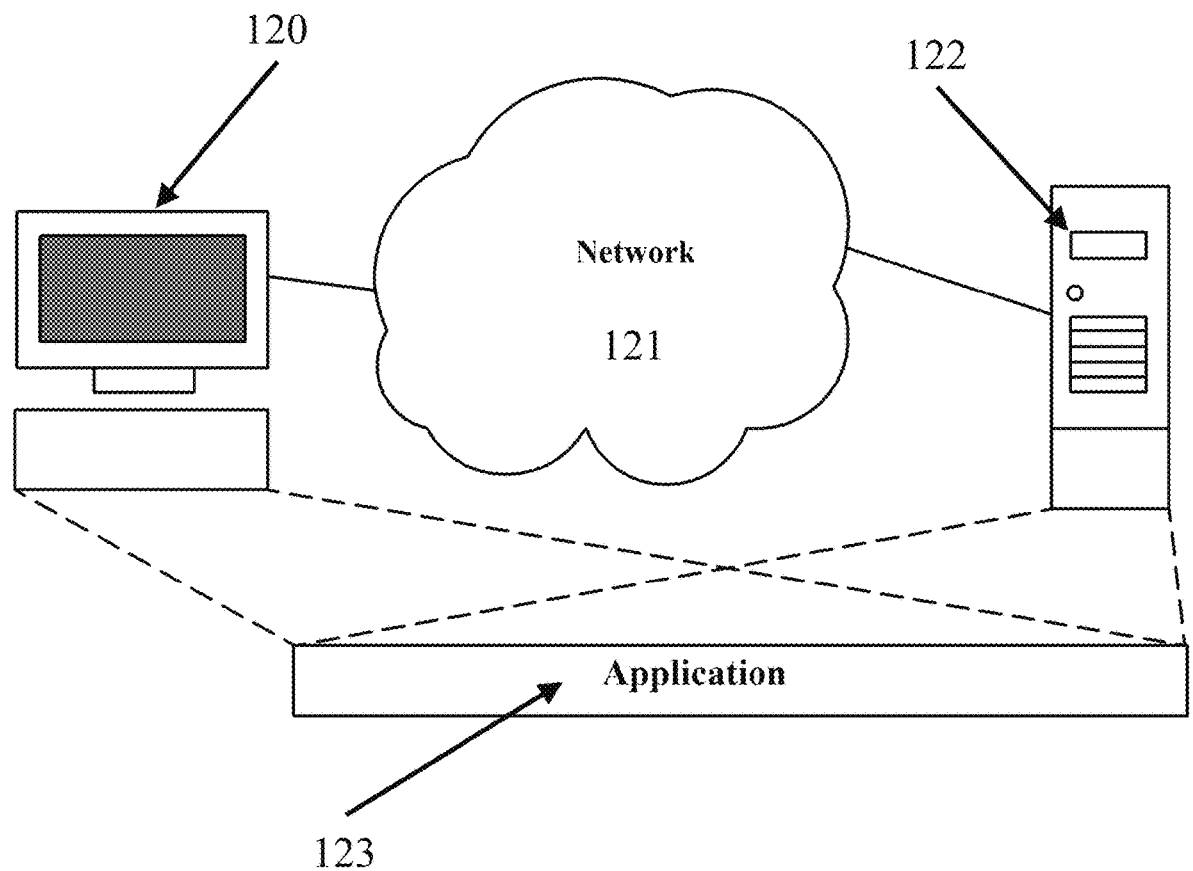
FIG. 1B is a schematic diagram of a network-based platform, as disclosed herein.

The systems may be deployed in a number of ways, including on a stand-alone computing device, a set of computing devices working together in a network, or a web application. Persons of ordinary skill in the art will recognize a web application as a particular kind of computer program system designed to function across a network, such as the Internet. A schematic illustration of a web application platform is provided in FIG. 1B Web application platforms typically include at least one client device 120, which is a computing device as described above. The client device 120 connects via some form of network connection to a network 121, such as the Internet. The network 121 may be any arrangement that links together computing devices 120, 122, and includes without limitation local and international wired networks including telephone, cable, and fiber-optic networks, wireless networks that exchange information using signals of electromagnetic radiation, including cellular communication and data networks, and any combination of those wired and wireless networks. Also connected to the network 121 is at least one server 122, which is also a computing device as described above, or a set of computing devices that communicate with each other and work in concert by local or network connections. Of course, practitioners of ordinary skill in the relevant art will recognize that a web application can, and typically does, run on several servers 122 and a vast and continuously changing population of client devices 120. Servers 122 as used herein may include computing devices used to support cloud applications, such as the computing devices used in one or more data centers. Tasks and data of the server 122 or servers may be distributed among physical devices according to any suitable protocol, including cloud architecture, load-balancing architecture, and other schemes for task and data distribution. This may include "serverless" architecture, wherein the cloud service running on the one or more servers 122 replaces conventional server use at one or more junctures of the network. The network 121 can be divided into sub-networks as well, such as a network in which the computing devices making up the server 122 are nodes, or a network in which the nodes are computing devices participating in particular coordinated actions. Computer programs on both the client device 120 and the server 122 configure both devices to perform the functions required of the web application 123. Web applications 123 can be designed so that the bulk of their processing tasks are accomplished by the server 122, as configured to perform those tasks by its web application program, or alternatively by the client device 120. Some web applications 123 are designed so that the client device 120 solely displays content that is sent to it by the server 122, and the server 122 performs all of the processing, business logic, and data storage tasks. Such "thin client" web applications are sometimes referred to as "cloud" applications, because essentially all computing tasks are performed by a set of servers 122 and data centers visible to the client only as a single opaque entity, often represented on diagrams as a cloud. Some web applications treat the network 121 or a part thereof as a "peer-to-peer" network, which distributes computing tasks and resources among its nodes; where each computing device making up a node of the network 121 can act as a client 120 or a server 122 depending on the task the protocols of the peer-to-peer network direct it to perform.

Many computing devices, as defined herein, come equipped with a specialized program, known as a web browser, which enables them to act as a client device 120 at least for the purposes of receiving and displaying data output by the server 122 without any additional programming. Web browsers can also act as a platform to run so much of a web application as is being performed by the client device 120, and it is a common practice to write the portion of a web application calculated to run on the client device 120 to be operated entirely by a web browser. Such browser-executed programs are referred to herein as "client-side programs," and frequently are loaded onto the browser from the server 122 at the same time as the other content the server 122 sends to the browser. However, it is also possible to write programs that do not run on web browsers but still cause a computing device to operate as a web application client 120. Thus, as a general matter, web applications 123 require some computer program configuration of both the client device (or devices) 120 and the server 122. The computer program that comprises the web application component on either computing device's system FIG. 1A configures that device's processor 200 to perform the portion of the overall web application's functions that the programmer chooses to assign to that device. Persons of ordinary skill in the art will appreciate that the programming tasks assigned to one device may overlap with those assigned to another, in the interests of robustness, flexibility, or performance. Furthermore, although the best known example of a web application as used herein uses the kind of hypertext markup language protocol popularized by the World Wide Web, practitioners of ordinary skill in the art will be aware of other network communication protocols, such as File Transfer Protocol, that also support web applications as defined herein.

The one or more client devices 120 and the one or more servers 122 may communicate using any protocol according to which data may be transmitted from the client 120 to the server 122 and vice versa. As a non-limiting example, the client 120 and server 122 may exchange data using the Internet protocol suite, which includes the transfer control protocol (TCP) and the Internet Protocol (IP), and is sometimes referred to as TCP/IP. Other protocols may include, without limitation, Internet Control Message Protocol (ICMP). In some embodiments, the client and server 122 encrypt data prior to exchanging the data, using a cryptographic system as described above. In one embodiment, the client 120 and server 122 exchange the data using public key cryptography; for instance, the client and the server 122 may each generate a public and private key, exchange public keys, and encrypt the data using each others' public keys while decrypting it using each others' private keys.

In some embodiments, the client 120 authenticates the server 122 or vice-versa using digital certificates. In one embodiment, a digital certificate is a file that conveys information and links the conveyed information to a "certificate authority" that is the issuer of a public key in a public key cryptographic system. The certificate in some embodiments contains data conveying the certificate authority's authorization for the recipient to perform a task. The authorization may be the authorization to access a given datum. The authorization may be the authorization to access a given process. In some embodiments, the certificate may identify the certificate authority.

The linking may be performed by the formation of a digital signature. In one embodiment, a digital signature is an encrypted mathematical representation of a file using the private key of a public key cryptographic system. The signature may be verified by decrypting the encrypted mathematical representation using the corresponding public key and comparing the decrypted representation to a purported match that was not encrypted; if the signature protocol is well-designed and implemented correctly, this means the ability to create the digital signature is equivalent to possession of the private decryption key. Likewise, if the mathematical representation of the file is well-designed and implemented correctly, any alteration of the file will result in a mismatch with the digital signature; the mathematical representation may be produced using an alteration-sensitive, reliably reproducible algorithm, such as a hashing algorithm. A mathematical representation to which the signature may be compared may be included with the signature, for verification purposes; in other embodiments, the algorithm used to produce the mathematical representation is publically available, permitting the easy reproduction of the mathematical representation corresponding to any file. In some embodiments, a third party known as a certificate authority is available to verify that the possessor of the private key is a particular entity; thus, if the certificate authority may be trusted, and the private key has not been stolen, the ability of an entity to produce a digital signature confirms the identity of the entity, and links the file to the entity in a verifiable way. The digital signature may be incorporated in a digital certificate, which is a document authenticating the entity possessing the private key by authority of the issuing certificate authority, and signed with a digital signature created with that private key and a mathematical representation of the remainder of the certificate. In other embodiments, the digital signature is verified by comparing the digital signature to one known to have been created by the entity that purportedly signed the digital signature; for instance, if the public key that decrypts the known signature also decrypts the digital signature, the digital signature may be considered verified. The digital signature may also be used to verify that the file has not been altered since the formation of the digital signature.

The server 122 and client 120 may communicate using a security combining public key encryption, private key encryption, and digital certificates. For instance, the client 120 may authenticate the server 122 using a digital certificate provided by the server 122. The server 122 may authenticate the client 120 using a digital certificate provided by the client 120. After successful authentication, the device that received the digital certificate possesses a public key that corresponds to the private key of the device providing the digital certificate; the device that performed the authentication may then use the public key to convey a secret to the device that issued the certificate. The secret may be used as the basis to set up private key cryptographic communication between the client 120 and the server 122; for instance, the secret may be a private key for a private key cryptographic system. The secret may be a datum from which the private key may be derived. The client 120 and server 122 may then use that private key cryptographic system to exchange information until the session in which they are communicating ends. In some embodiments, this handshake and secure communication protocol is implemented using the secure sockets layer (SSL) protocol. In other embodiments, the protocol is implemented using the transport layer security (TLS) protocol. The server 122 and client 120 may communicate using hyper-text transfer protocol secure (HTTPS).

Embodiments of the disclosed system and method use sensors to record user performance of exercises, and use the recorded data to identify a motion deficiency, such as lack of core strength, balance, or range of motion. In some embodiments, the system develops an exercise the user can follow to correct the motion deficiency, and instructs the user in performing the exercise. The system may also provide feedback in real time, allowing the user to improve the performance of the corrective exercise; the program may also incrementally add to the exercise as the user's condition improves.

Figure 2A:
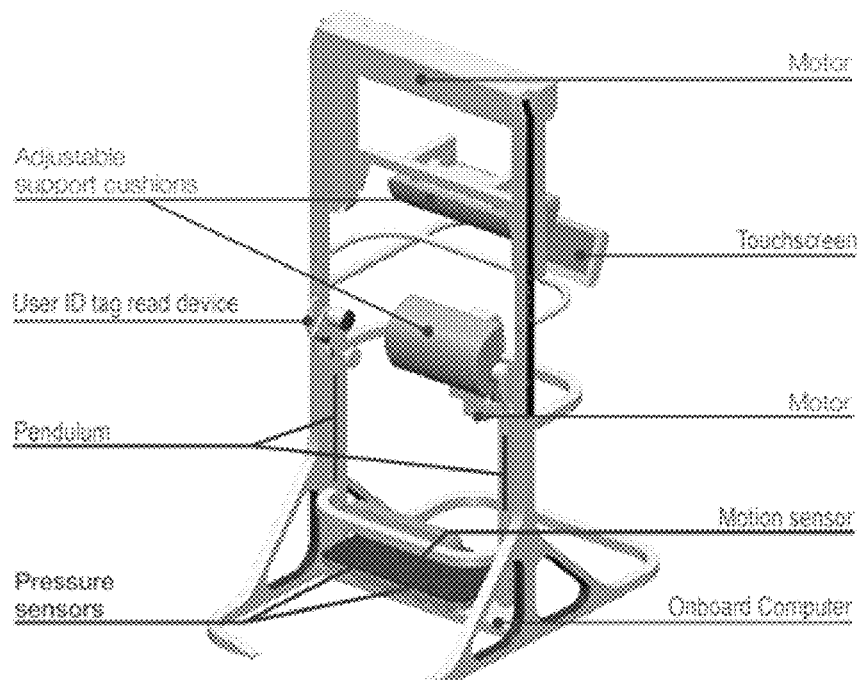
FIG. 2A is a schematic diagram of an embodiment of the disclosed system.
Figure 2B:
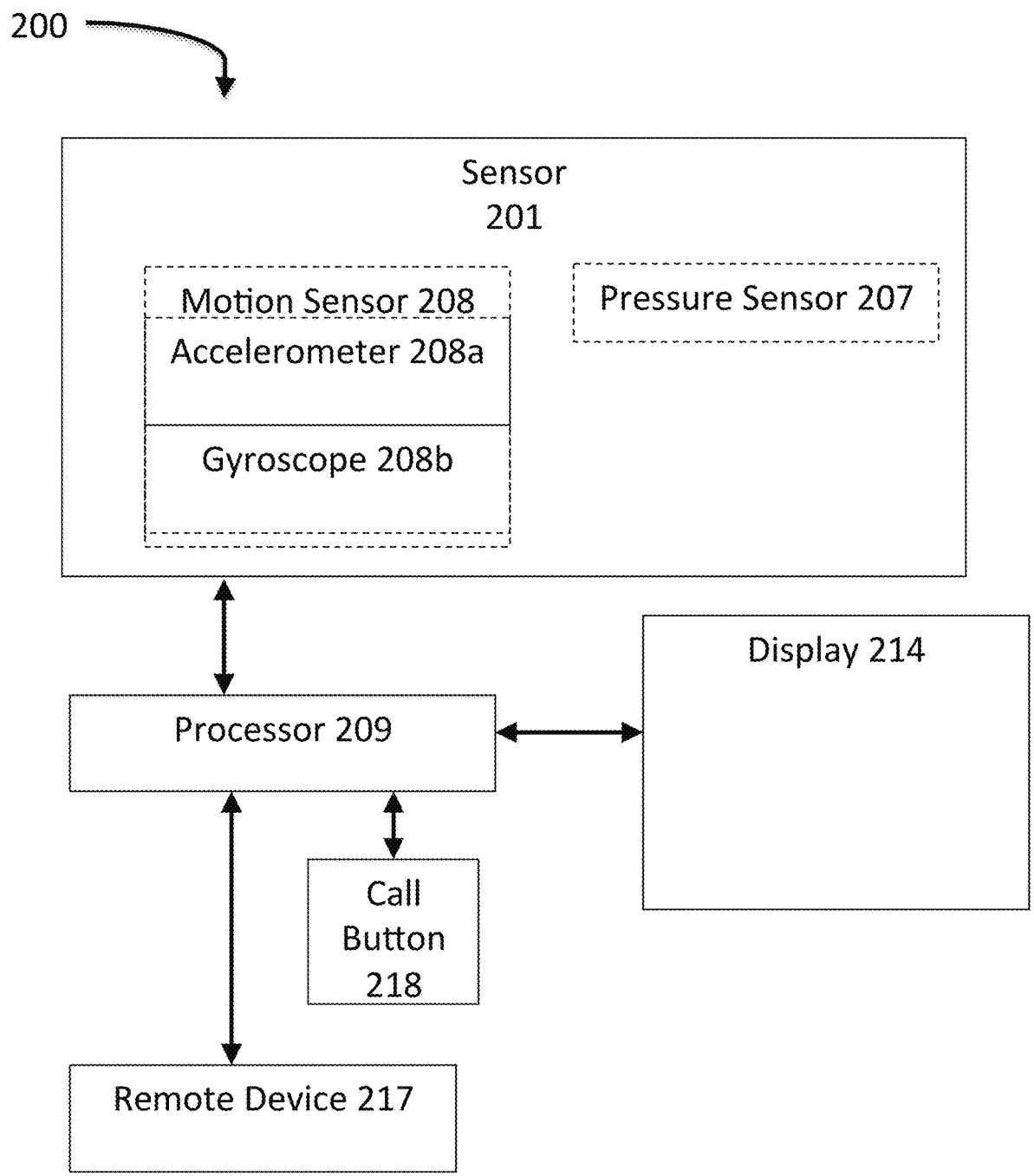
FIG. 2B is a block diagram of an embodiment of the disclosed system.

FIGS. 2A-B illustrates an embodiment of a system 200 for identifying and correcting motion through exercise. As an overview, the system 200 includes at least one sensor 201. The system 200 may include an exercise machine having a frame 202. The system may include a pendulum 203. The pendulum 203 may have a proximal end 204 journaled on the frame and a distal end 205. The system 200 may include a platform 206 at the distal end 205 of the pendulum 203; the platform 206 may be sized to accommodate both feet of a user.

Referring to FIGS. 2A-B in further detail, the at least one sensor 201 may include at least one pressure sensor 207. The at least one pressure sensor 207 may be any sensor that detects pressure or force being applied to the sensor and converts the detected pressure or force to an electric signal that reflects the degree of pressure or force being applied to the sensor 207. As a non-limiting example, the at least one pressure sensor 207 may include a load cell. The at least one pressure sensor 207 may include a plurality of pressure sensors; for instance, the at least one pressure sensor 207 may include a plurality of load cells distributed over a surface, and able together to determine the distribution of force or pressure being applied to the surface. In some embodiments, where the system 200 includes a platform 206, the at least one pressure sensor is incorporated in the platform. The platform 206 may, as a non-limiting example, be a balance-sensing platform that can detect the distribution of force being applied to the platform when the user stands on the platform; this may enable the system 200 to determine the distribution of weight or other forces on the user's feet. The at least one pressure sensor 207 may include a dynamometer.

In some embodiments, the at least one sensor 201 includes at least one motion sensor 208. Where the system 200 includes a pendulum 203, the at least one motion sensor 208 may be incorporated in the pendulum 203. The at least one motion sensor 208 may be incorporated in the platform 206, where present. The at least one motion sensor 208 may include a plurality of motion sensors, which may be included in a plurality of locations in the system 200. In some embodiments, the at least one motion sensor 208 includes at least one accelerometer 208*a*. The at least one accelerometer 208*a* may include a plurality of accelerometers, which may be oriented so that together they can detect acceleration in two dimensions or three dimensions; for instance, the accelerometers may be mutually orthogonal, so that two of them can detect acceleration in any direction in two dimensions, and three of them can detect acceleration in any direction in three dimensions. In some embodiments, a sensor can be a heart rate monitor sensor attached to or embedded in the handles of the exercise machine. In some embodiments, the heart rate monitor sensor can be attached to or embedded into various parts of the exercise machine, such as bars, support and safety cushions, etc. In some embodiments the heart rate monitor sensor can be attached to or embedded into a neck device described infra and shown in FIGS. 17A-B.

In some embodiments, the at least one motion sensor 208 includes at least one gyroscope 208*b*. The at least one gyroscope 208*b* may be able to detect changes in orientation. In some embodiments, the at least one gyroscope 208*b* includes a plurality of gyroscopes, which may detect changes in orientation in two or three dimensions; for instance, three gyroscopes with mutually orthogonal axes may be able to detect orientation changes in three dimensions. The at least one motion sensor 208 may combine at least one gyroscope 208*b* and at least one accelerometer 208*a* in a single unit or circuit, such as an inertial measurement unit (IMU). The at least one sensor 201 may also include, without limitation, infrared or other distance/displacement measurement sensors that determine the distance between parts of the machine, angular encoders, torque meters, or combination of torque meters with angular encoders. The at least one sensor 201 may be placed anywhere on the exercise machine, including without limitation axis points of rotating pendulums, platforms, and cushions.

The system 200 may include a processor 209 coupled to the at least one sensor 201. The processor 209 may be any processor as described above in reference to FIGS. 1A-B. The processor 209 may be incorporated in a computing device, including without limitation a microcontroller. The processor 209 may be configured to record, using the at least one sensor, an exercise motion performed by a user, to identify a motion deficiency of the user based on the detected exercise motion, to formulate a corrective motion based on the detected motion deficiency, and to provide the corrective motion to the user, as set forth in further detail below in connection with FIG. 3A. The processor 209 may be connected to one or more other electrical components, such as a transceiver; the processor 209 may be coupled to another computing device (not shown), which may perform some or all of the method steps described below in FIG. 3A. The method steps may be distributed among two or more computing devices or implemented as a web application or cloud application as described above in reference to FIGS. 1A-B.

In some embodiments, where the system 200 includes a frame 202, the frame 202 is made of a substantially rigid, strong material. The frame 202 may be constructed at least in part of metal; for instance, the frame 202 may be made of steel. The frame 202 may be constructed at least in part of polymer material. The frame 202 may be constructed at least in part of composite material. The frame 202 may be constructed at least in part of wood. The frame 202 may include a base; the base may be broad enough to prevent the frame from tipping over when the user is performing exercise motions and corrective motions as described in further detail below in reference to FIGS. 3A-4. The frame 202 may include one or more vertical bars; in some embodiments, two or more vertical bars are joined to each other by at least one horizontal bar, to form one or more rectangular sections. The frame 202 may include one or more braces connecting the rest of the frame 202 to the base; the braces may add stability to the frame 202 by resisting shear stresses and flexion, and may include without limitation triangular braces. The height, width, or other dimensions of the frame 202 may be manually adjustable; for instance, the frame 202 may include one or more mutually slidable sections which can be fixed or moved with respect to each other using a manual control, such as a pin inserted through a hole, a latch joining the sections, or a screw that secures sections together or advances the sections past each other, so that a user is able to slide the sections mutually to increase or decrease a dimension of the frame 202. The height, width, or other dimensions of the frame 202 may be electrically adjustable; for instance, an electric motor 210 may be connected to two or more mutually slidable sections of the frame 202 so that the electric motor may be activated to lengthen or shorten a dimension of the frame 202. The electric motor may be controlled by the processor 209 if present, or by a manual switch or other control device. The frame 202 may include one or more cushions 212; the one or more cushions may be formed of any padding or flexible material, including without limitation textiles, natural or artificial polymer sheets such as rubber, leather, natural or artificial foam, which may be closed or open cell foam, fiber padding, and the like. The one or more cushions 212 may be attached to an adjustment mechanism 210 that modifies a distance of the at least one support cushion from at least one of the frame, the platform, and the pendulum. The adjustment mechanism may be mechanical or electrical; the adjustment mechanism may be implemented similarly to the mechanism to adjust a dimension of the frame 202, and may be the mechanism to adjust a dimension of the frame 202. The one or more cushions may be weighted.

In some embodiments of the system 200 that include a pendulum 203, the pendulum is joined to the frame 202 at one or more points; for instance, the pendulum 203 may include at least one bar joined to at least one vertical bar of the frame 202. The pendulum 203 may include two bars journaled on two vertical bars of the frame 202. The joint attaching the proximal end 204 of the pendulum 203 to the frame 202 may include at least one very low-friction bearing, such as a ball bearing or electrodynamic bearing. In some embodiments, the pendulum 203 is connected to a resistance mechanism (not shown), such as a weight, a cable attached to a weight via a pulley system, elastic materials such as natural or synthetic rubber, or any combination of these elements. In other embodiments, the pendulum 203 does not have a resistance mechanism; in other words, the user's weight or momentum, or both, may supply the resistance in exercising with the pendulum 203. The pendulum 203 may include one or more cushions 213*a-b*. The one or more cushions 213*a-b* may include a safety support cushion 213*b*; the safety support cushion 213*b* may act to help secure the user to the pendulum 203, for instance making it more difficult for the user's feet to slip off of the platform 206 during exercise. The one or more cushions 213*a-b* may include a support cushion 213*a* that can hold the user's weight during the traversal of the pendulum. The one or more cushions 213*a-b* may be constructed of any material or combination of materials suitable for the construction of the one or more cushions 212 included in the frame 202 as described above. The one or more cushions 213 may be attached to an adjustment mechanism 211 that modifies a distance of the at least one support cushion from at least one of the frame, the platform, and the pendulum; the adjustment mechanism may be implemented as described above. The height, width, or other dimensions of the pendulum 203 may be manually adjustable; for instance, the pendulum 203 may include one or more mutually slidable sections which can be fixed or moved with respect to each other using a manual control 211, such as a pin inserted through a hole, a latch joining the sections, or a screw that secures sections together or advances the sections past each other, so that a user is able to slide the sections mutually to increase or decrease a dimension of the pendulum 203. The height, width, or other dimensions of the frame 202 may be electrically adjustable; for instance, an electric motor may be connected to two or more mutually slidable sections of the frame 202 so that the electric motor may be activated to lengthen or shorten a dimension of the frame 202. The electric motor may be controlled by the processor 209 if present, or by a manual switch or other control device.

Figure 16D:
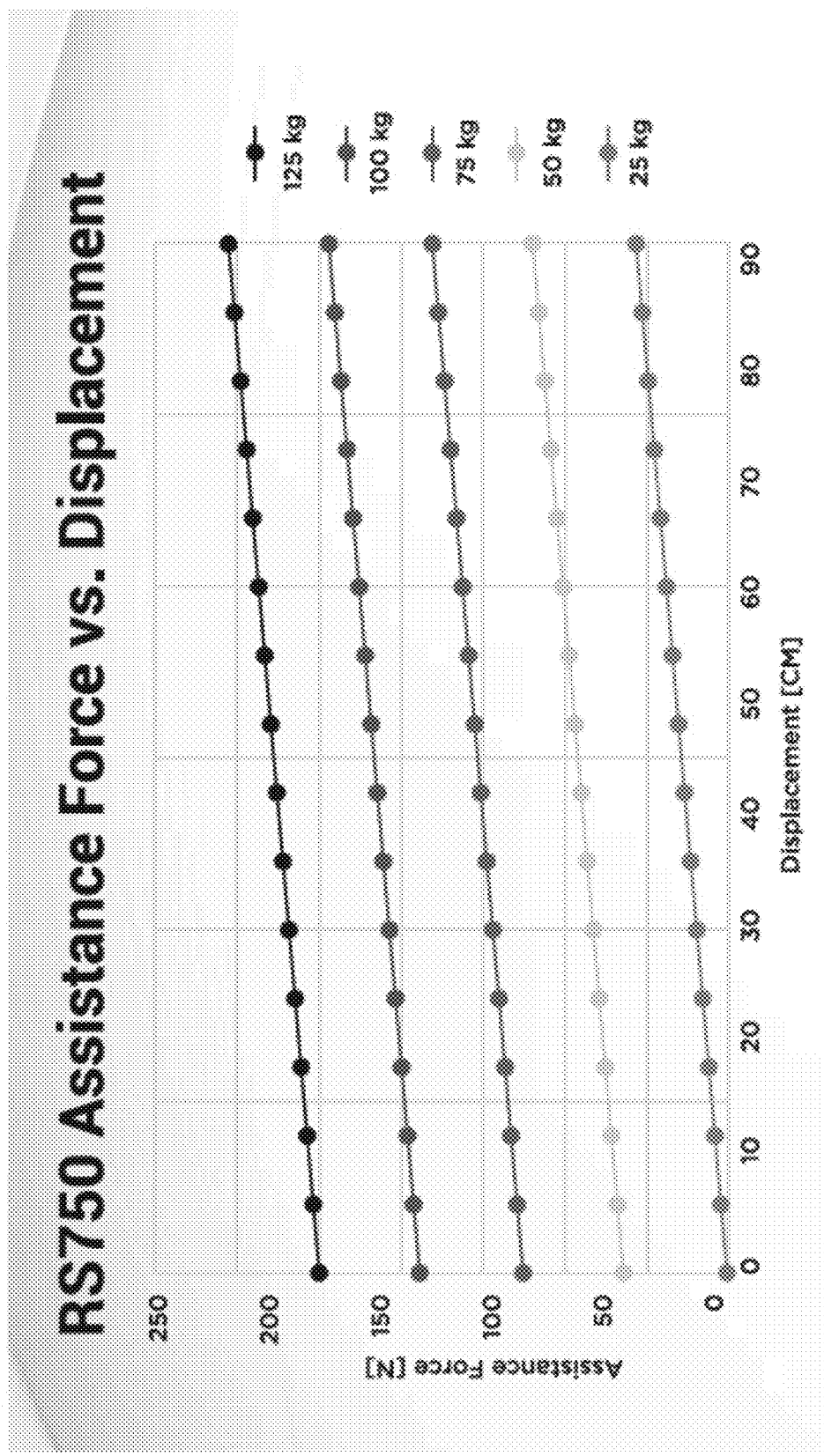
FIG. 16D is a graph of a function exhibited by the embodiment of FIG. 16A.
Figure 16E:
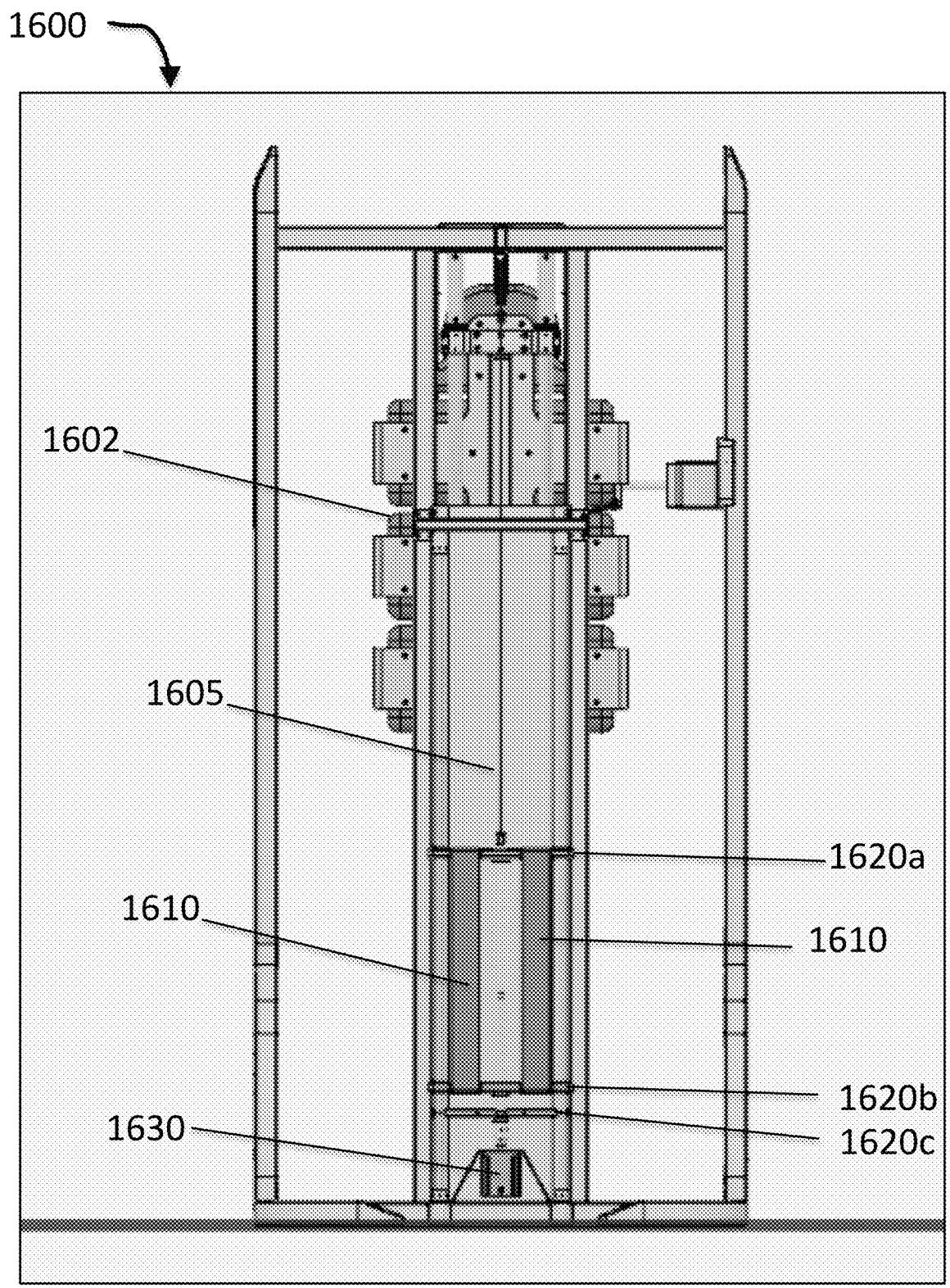
FIG. 16E is a schematic diagram showing the back side view of the embodiment of FIG. 16A with an alternative weight counterbalance mechanism.
Figure 17A:
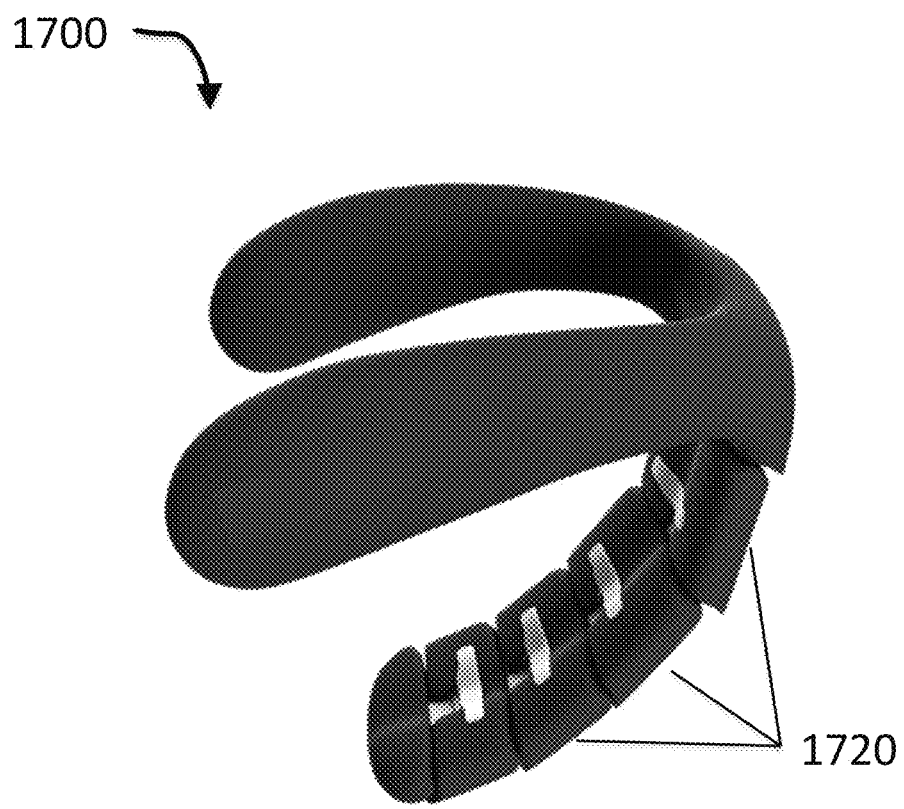
FIG. 17A is a schematic diagram showing an embodiment of the disclosed system.
Figure 17B:
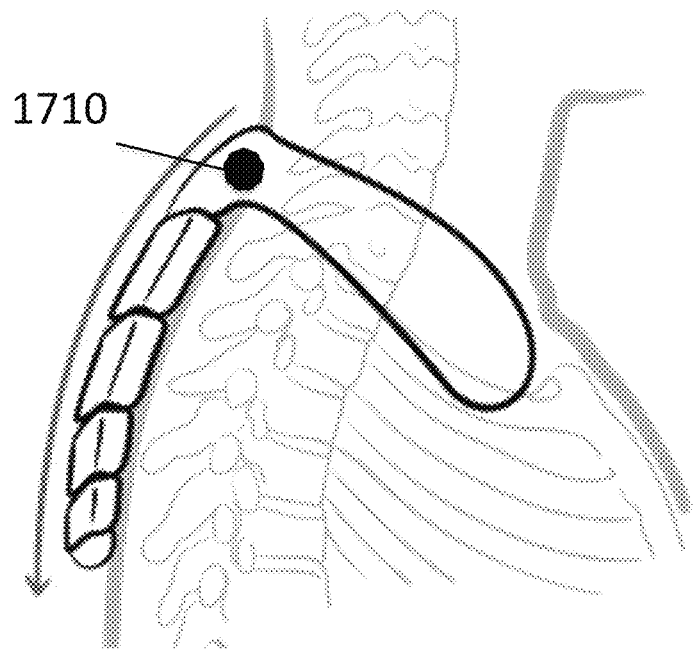
FIG. 17B is a schematic diagram illustrating the embodiment of FIG. 17A.

Additional embodiments of the exercise machine may include a machine, as illustrated in FIGS. 6A-6D, having a moving weighted cushion that loads the spine while the user stands on knees and elbows (e.g. performing a cat and camel exercise), a guided squat device, as illustrated in FIGS. 16A-16E, where a seat moves up and down assisted by a counterweight, a fixed board, as shown in FIGS. 12A-12D and FIGS. 13A-13E where the machine is static but a separate neck collar, as illustrated in FIGS. 17A-17B, is placed on the person, the device having a sensor inside to measure the movements of the spine, wherein the sensor is placed above the C7 vertebra allowing to measure the motion of thoracic spine and disregard the motion of the head. The following is a more detailed discussion of each exercise machine, which when used together, form a comprehensive system that produces a synergetic effect manifested in improved mobility of various body segments.

Figure 5A:
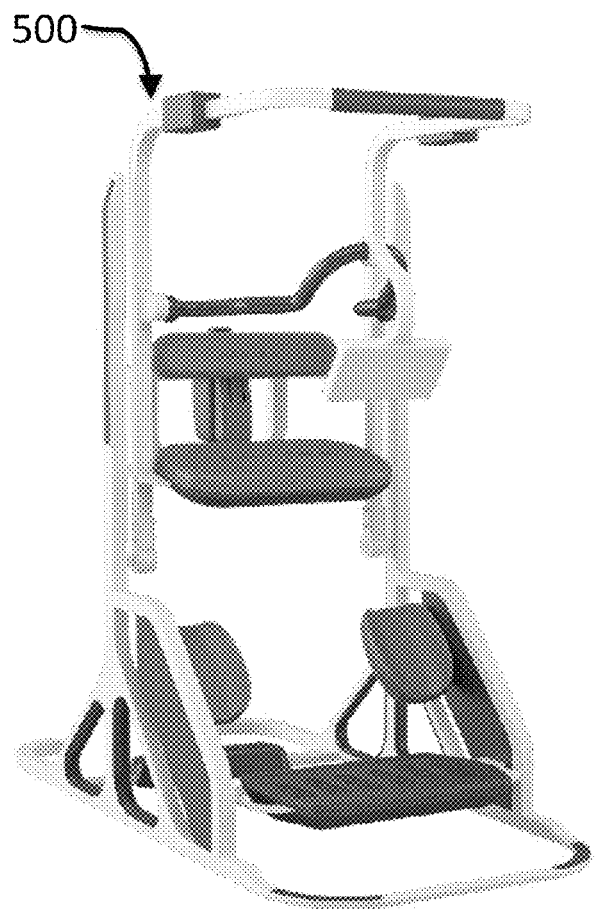
FIG. 5A is a schematic diagram of an embodiment of the disclosed system.
Figure 5B:
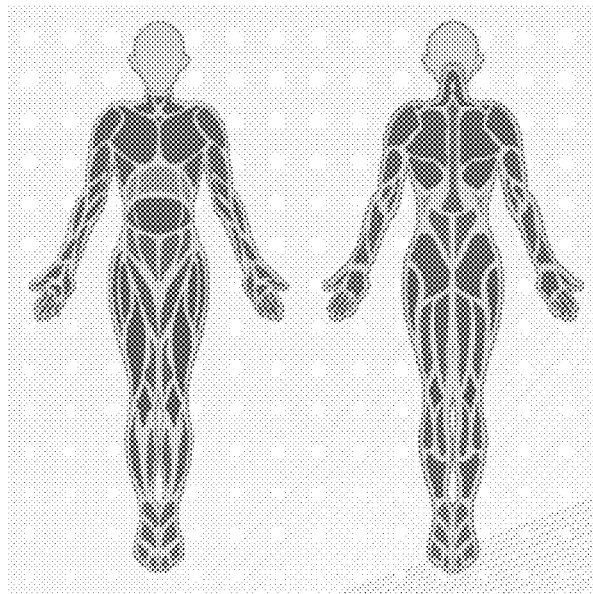
FIG. 5B is a schematic diagram showing body segments that can be targeted using the embodiment of FIG. 5A.
Figure 5C:
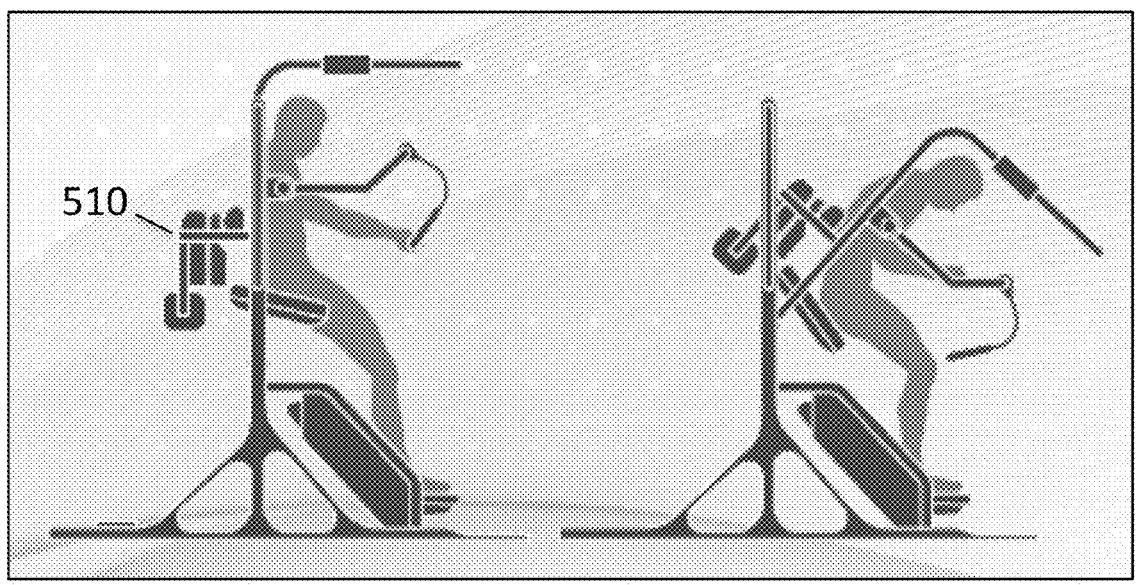
FIG. 5C is a schematic diagram showing the embodiment of FIG. 5A in action.
Figure 5D:
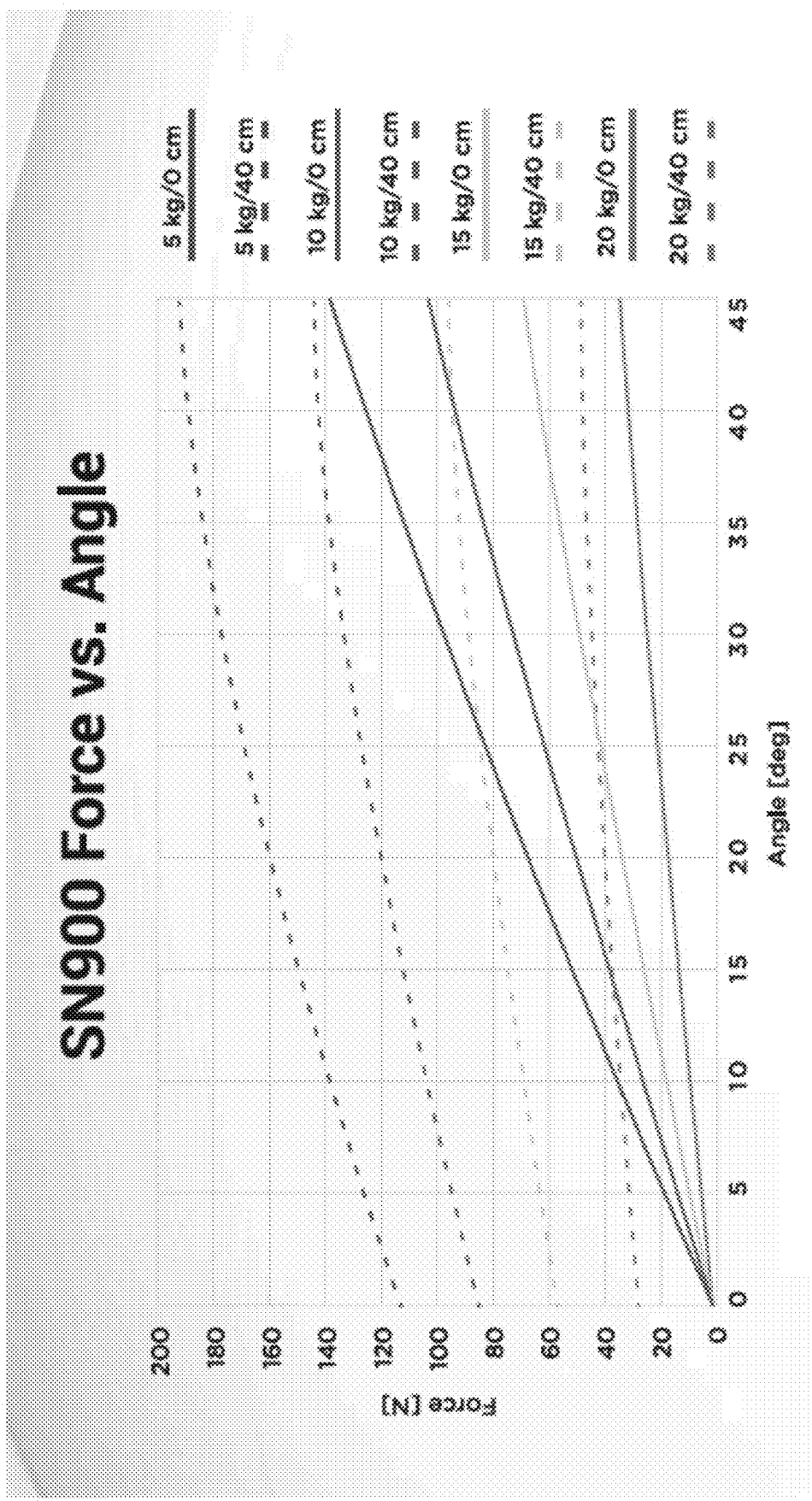
FIG. 5D is a graph of a function exhibited by the embodiment of FIG. 5A.

Referring to FIGS. 5A-5D, a torso engagement trainer exercise machine features a zero-friction pendulum, safety support cushion, precision motion sensors, balance and force plates, active cushion, an IoT connected processing touch screen and an NFC reader. The machine can be made of industry grade steel and can have antibacterial surfaces. According to an embodiment of the present invention, various parts of the exercise machine (such as handles, knobs, arm rests, etc.) can be coated with an antimicrobial coating. The antimicrobial coating can be formed from antimicrobial metals such as copper or silver. The antimicrobial metal can be provided as a powder and deposited on various parts of the exercise machine using cold spray method, for example. The thickness of an antibacterial coating can be in the range from 100 nm to 5 mm, or in some instances from 5 mm to 10 mm. In some embodiments, the thickness of the coating can be in the range from 500 nm to 5000 microns, and in some embodiments in the range from 1 micron to 5000 microns. The coating can include metals such as copper, brass, silver, alloys or combination thereof. In some instances, an antimicrobial substance can be incorporated into the materials that cushions and other parts of the machines are made of. The substance can be a commercially available product such as Biomaster made by Addmaster Ltd, a UK-based provider of high performance antibacterial additives. As illustrated in FIG. 5B, exercises performed on this machine can target various body segments such as target joints (thoracolumbar junction, lumbosacral spine, anterior pelvic arch, pelvic floor, hips, knees, ankles), target ligaments (aponeurotic roots of thoracolumar fascia, posterior longitudinal, sacroiliac ligaments, sacrotuberous, liolumbar, liotibial band, patellar reinaculums and ligament) and target muscles such as erectors sponaer, interrspinalis, latissimus dorsi, quadratus lumborum, glutes, vastus lateralis, quadrecips, and Iliopsoas. The load or resistance can be changed by using plates of various weights and/or by changing the position of the weight plate by moving it along bar 510 (FIG. 5C), thereby changing the distances from the fulcrum to where the input and output forces are applied to the lever, hence changing the ratio of the output force to the input force in accordance with the law of the lever, as illustrated in FIG. 5D showing the dependence of the exerted force on the displacement angle at various distances of the weight plate from the proximate end of bar 510.

Figure 6A:
FIG. 6A is a schematic diagram of an embodiment of the disclosed system.
Figure 6B:
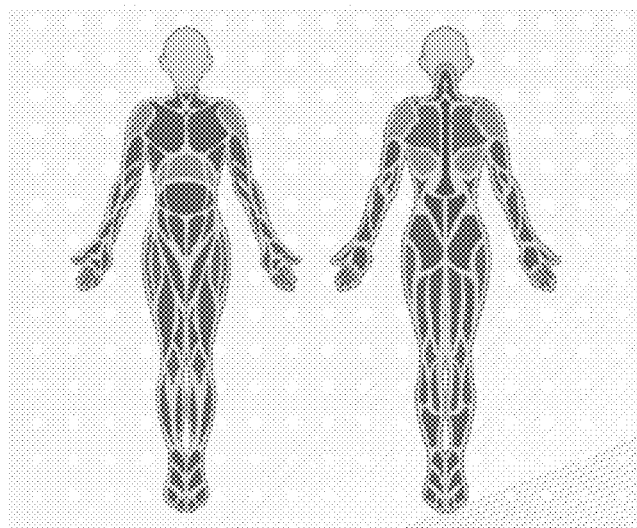
FIG. 6B is a schematic diagram showing body segments that can be targeted using the embodiment of FIG. 6A.
Figure 6C:
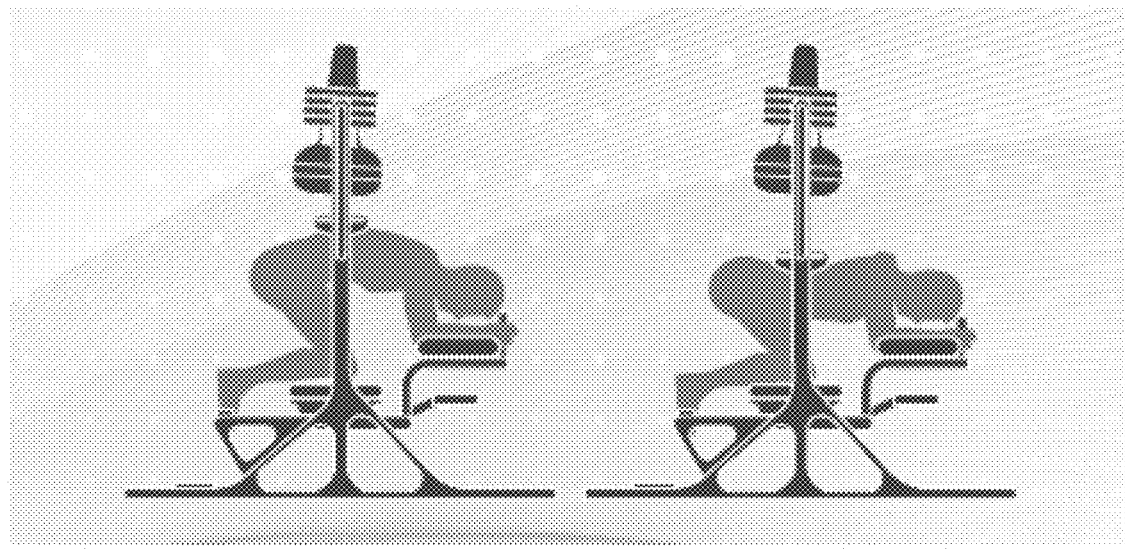
FIG. 6C is a schematic diagram showing the embodiment of FIG. 6A in action.
Figure 6D:
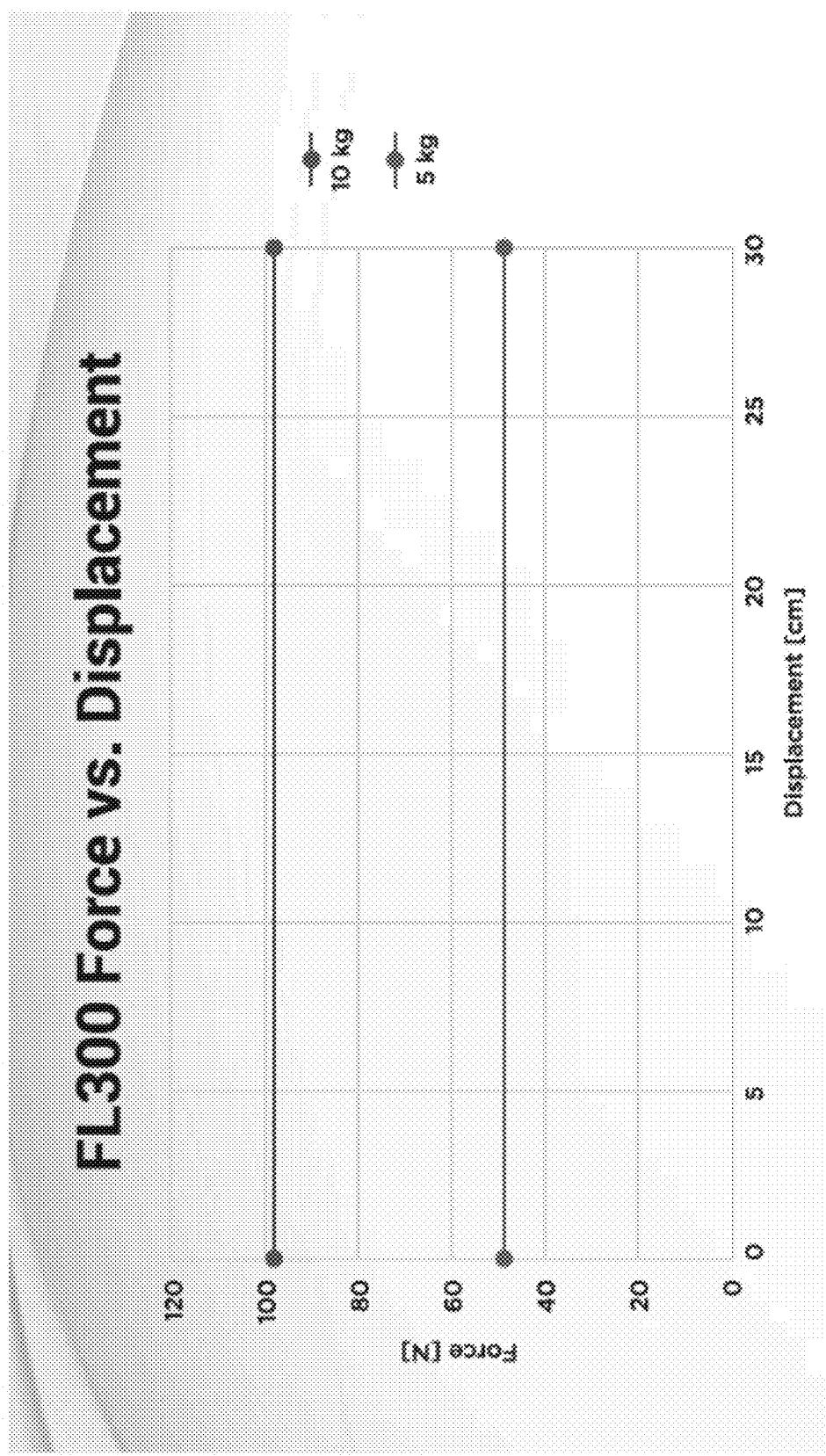
FIG. 6D is a graph of a function exhibited by the embodiment of FIG. 6A.

Referring to FIGS. 6A-6D, a torso trainer exercise machine features an industry grade steel construction, electrical height adjustment, active cushion, variable loading, antibacterial surfaces, screen protector, precision motion sensors, balance and force plates, an IoT connected processing TFT touch screen and an NFC reader. As shown in FIG. 6B, performing a cat and camel exercise can target various body segments such as target joint (shoulders, cervical thoracic junction, thoracic spine, thoracolumbar junction, lumbosacral spine, diaphragm arch, pelvic floor, hops and knees), target ligament such as anterior longitudinal, posterior longitudinal, thoracolumbar fascia, costotransverse, rectus sheath, external oblique aponeurosis, paraspinal retinacular sheath, as well as target muscles such as serratus posterior superior, rhomboids, latissimus dorsi, diaphragms, deep extensors (semispinalis and multifidus), and erectors spinae (iliocostalis, spinalis, longissimus). FIG. 6D illustrates the dependence of the force on the displacement of the active cushion using a 10 kg weigh plate and a 5 kg weigh plate.

Figure 7D:
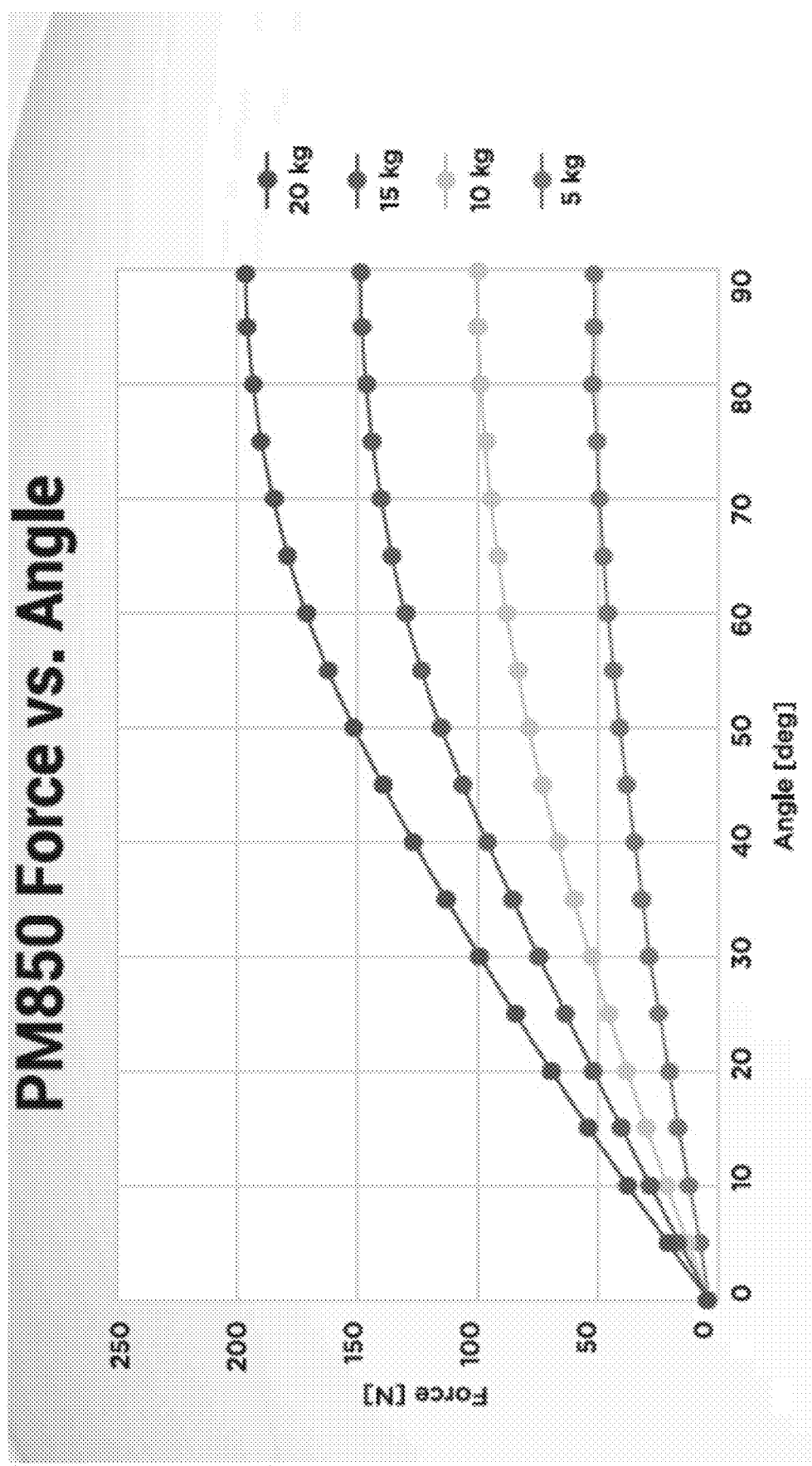
FIG. 7D is a graph of a function exhibited by the embodiment of FIG. 7A.

Referring to FIGS. 7A-7D, a lumbar spine trainer exercise machine features an industry grade steel construction, safety support cushion, zero-friction pendulum, active cushion, antibacterial surfaces, precision motion sensors, balance and force plates, IoT connected processing TFT touch screen and an NFC reader. As illustrated in FIG. 7B, performing exercise on this machine can target joints such as thoracic spine, thoracolumbar junction, lumbar spine, lumbosacral junction, diaphragm arch, pubic arch, target ligaments such as anterior longitudinal posterior longitudinal, aponeurotic roots of thoracolumbar fascia, costotransverse, rectus sheath, falx inguinalis, paraspinal retinacular sheath, as well as target muscles such as serratus posterior inferior, serratus anterior, latissimus dorsi, diaphragm, rectus abdominis, deep extensors (semispinalis and multifidus), and erectors spinae thoracis (iliocostalis, spinalis, longissimus). FIG. 7D illustrates the dependence of the force on the displacement angle at different weight loads ranging from 5 kg to 20 kg.

Figure 8D:
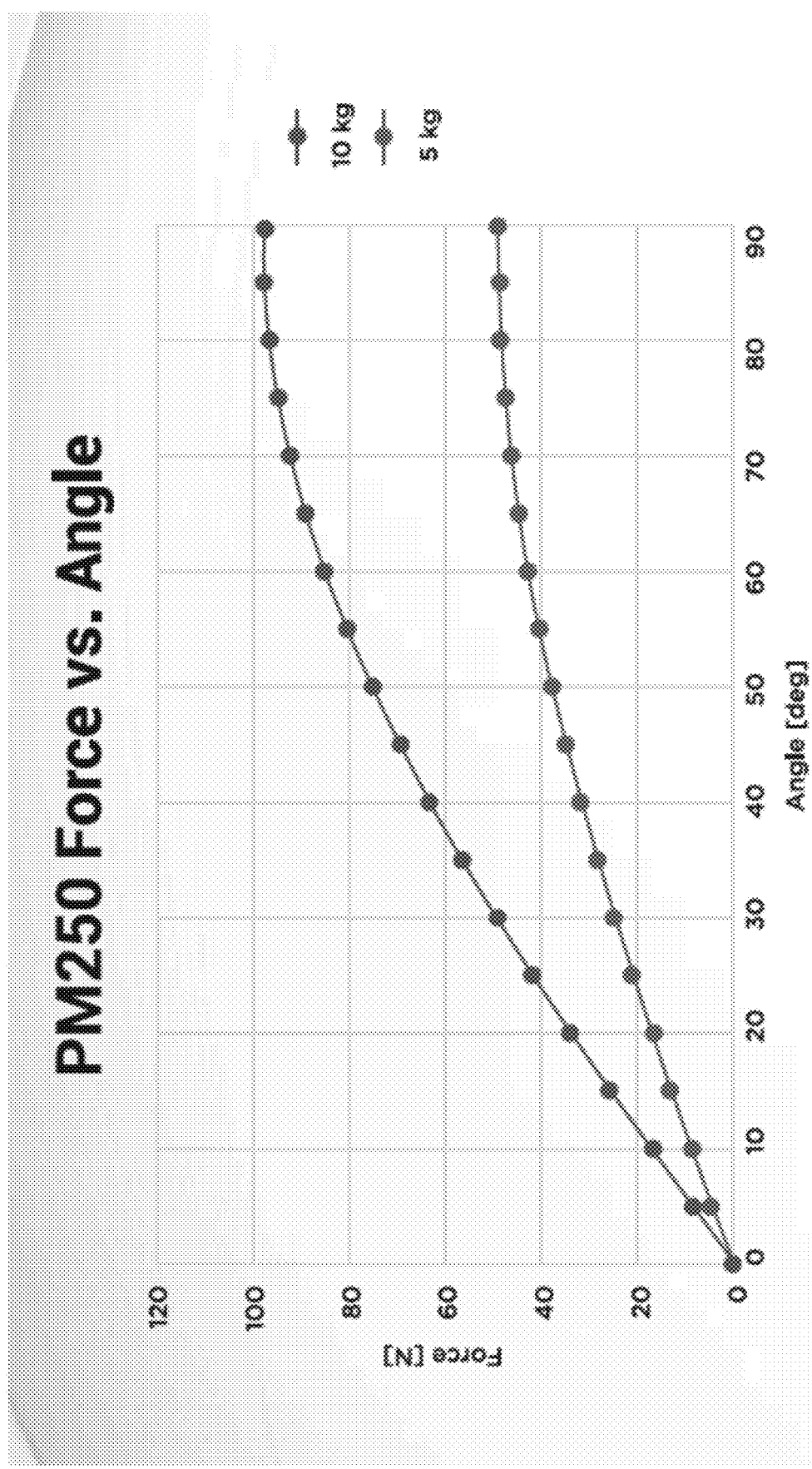
FIG. 8D is a graph of a function exhibited by the embodiment of FIG. 8A.

FIGS. 8A-8D illustrate an embodiment of a pelvic support trainer machine featuring an industry grade steel construction, safety support cushion, zero-friction pendulum, active cushion, antibacterial surfaces, precision motion sensors, balance and force plates, an IoT connected processing TFT touch screen and an NFC reader. FIG. 8B illustrates various body segments targeted by performing exercises on this machine and target joint such as thoracolumbar junction, lumbar, lumbosacral junction, lumboiliac junctions, lilac crests inferior attachments, hips, pelvic floor, target ligaments such as supraspinous, gluteal aponeurosis, sacroiliac ligaments, sacrotuberous, lliolumbar, lliotibial band, sacrococcygeal, lliolumbar ligaments as well as target muscles such as erectors spinae (iliocostalis, spinalis, longissimus), glutes, pelvic floor muscles, rectus femoris, tensor fasciae latae, llippsoas, and piriformis. The machine is characterized by the dependence of the force on the displacement angle as showing in FIG. 8D, at 5 kg weight plate and 10 kg weight plate.

Figure 9A:
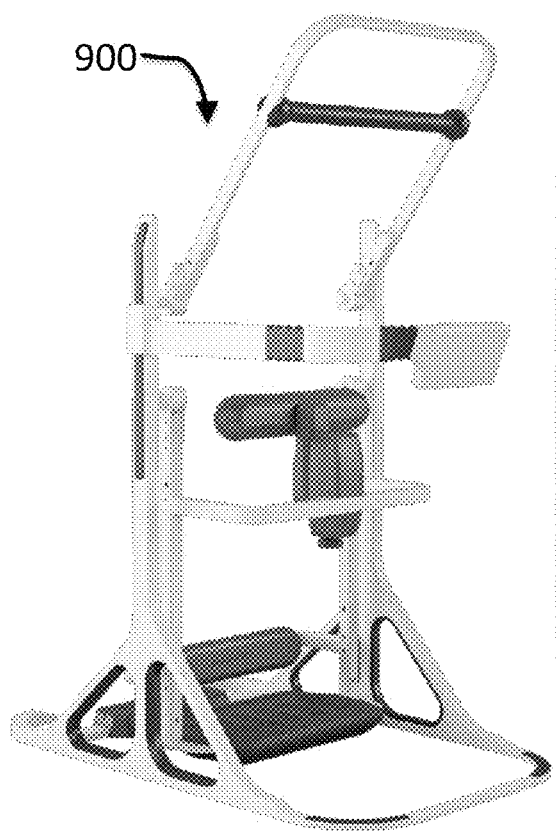
FIG. 9A is a schematic diagram of an embodiment of the disclosed system.
Figure 9B:
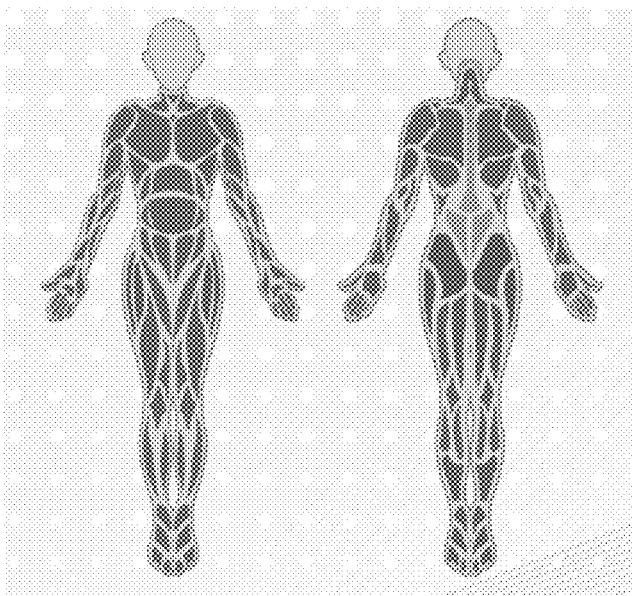
FIG. 9B is a schematic diagram showing body segments that can be targeted using the embodiment of FIG. 9A.
Figure 9C:
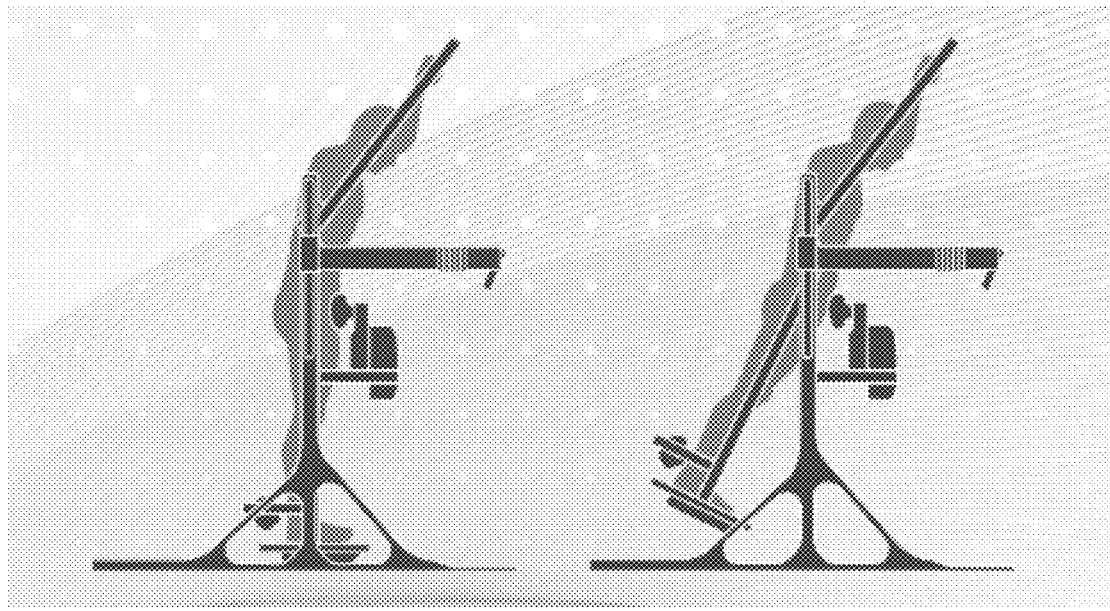
FIG. 9C is a schematic diagram showing the embodiment of FIG. 9A in action.
Figure 9D:
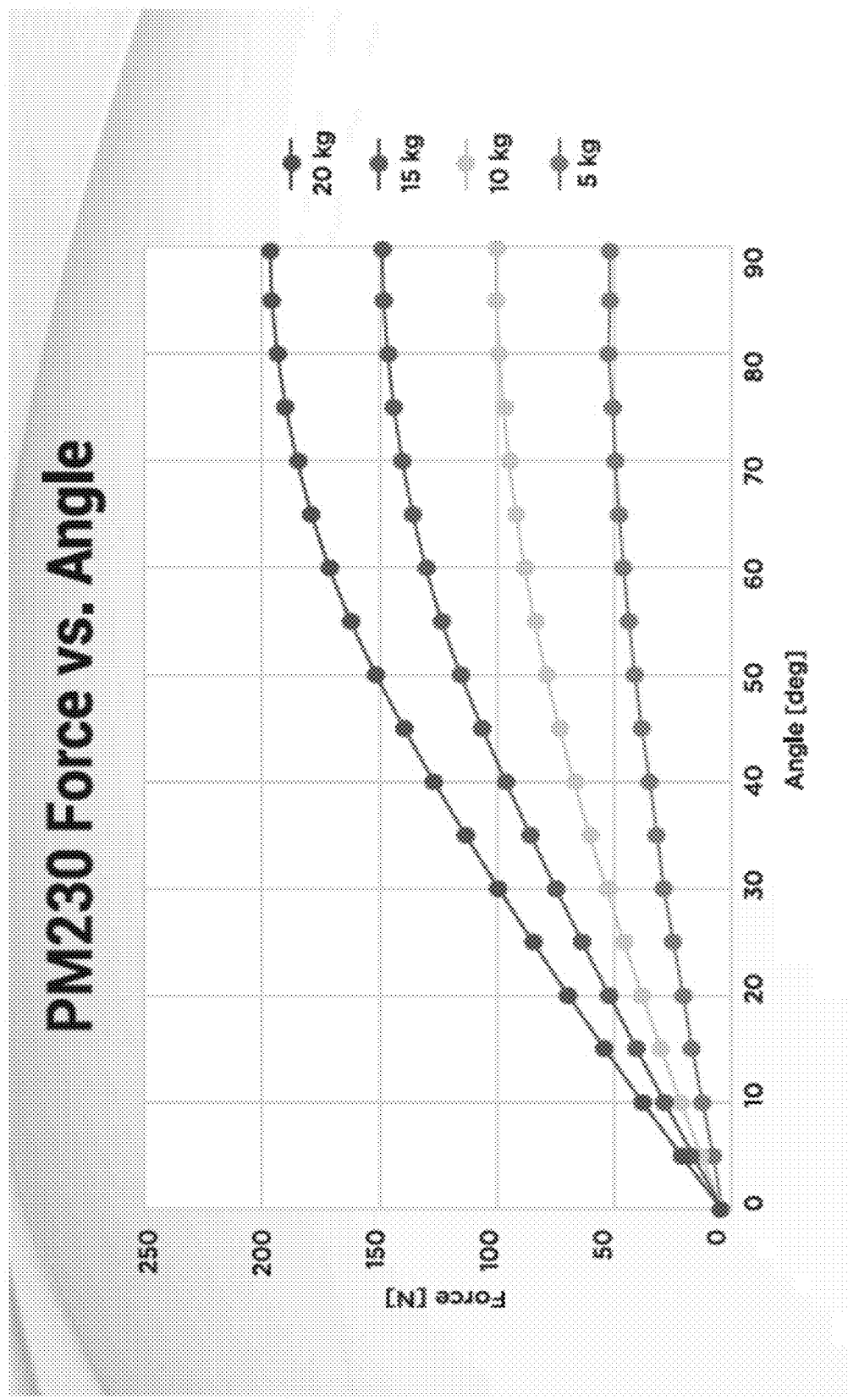
FIG. 9D is a graph of a function exhibited by the embodiment of FIG. 9A.

FIGS. 9A-9D show an embodiment of a shoulder/spine/pelvis trainer exercise machine, which features a zero-friction pendulum, industry grade steel construction, safety support cushion, active cushion, antibacterial surfaces, precision motion sensors, balance and force plates, an IoT connected processing TFT touch screen and an NFC reader. As shown in FIG. 9B, various body segments can be targeted by performing exercises on this machine, affecting joints such as thoracic spine, thoracolumbar junction, lumbar spine, lumbosacral junction, lumboiliac junctions, lilac crests superior attachments and hips; as well as target ligaments such as anterior longitudinal, posterior longitudinal, aponeurotic roots of thoracolumbar fascia, lumbosacral ligaments, external oblique aponeurois, auadratus lumborum fascia, as also target muscles such as deep extensors (spinalis, thoracis and multifidus), serratus posterior infriro, glutes, internal and external obliques, transverus abdominis liocostalis lumborum, and interspinalis lumborum. The machine can be characterized by the force vs. angle dependence as shown in FIG. 9D, using weight plates ranging from 5 kg to 20 kg.

Figure 10A:
FIG. 10A is a schematic diagram of an embodiment of the disclosed system.
Figure 10B:
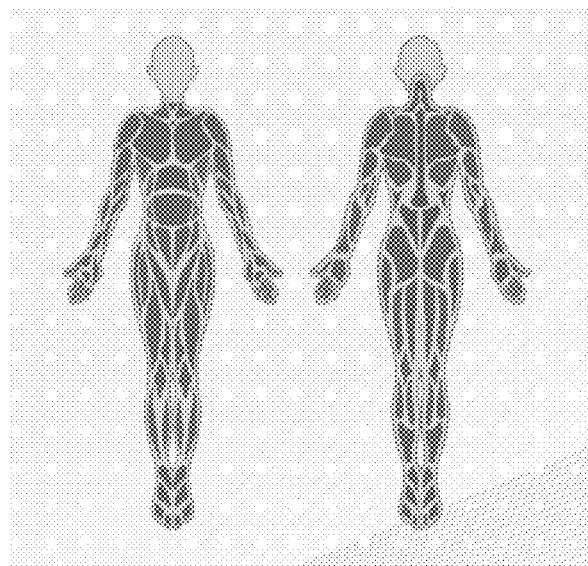
FIG. 10B is a schematic diagram showing body segments that can be targeted using the embodiment of FIG. 10A.
Figure 10C:
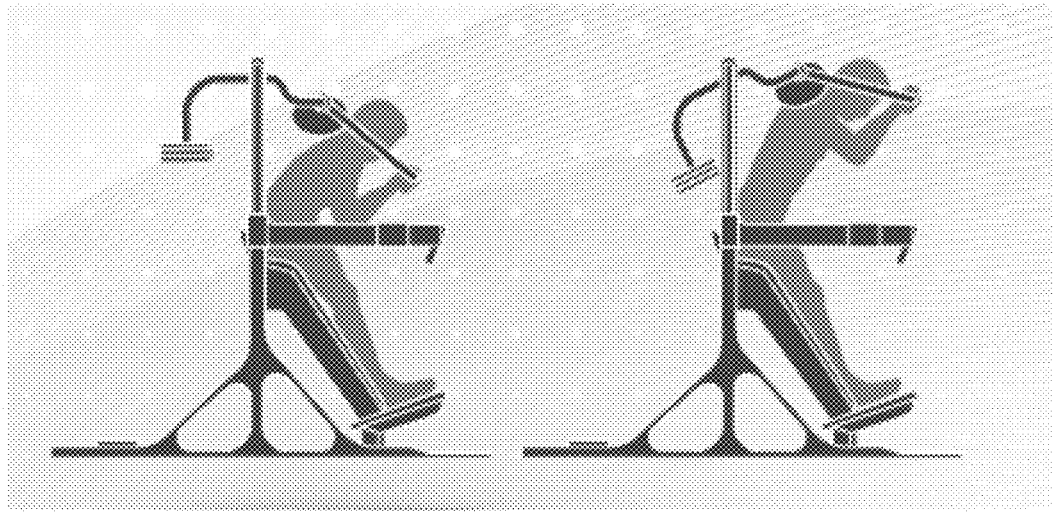
FIG. 10C is a schematic diagram showing the embodiment of FIG. 10A in action.
Figure 10D:
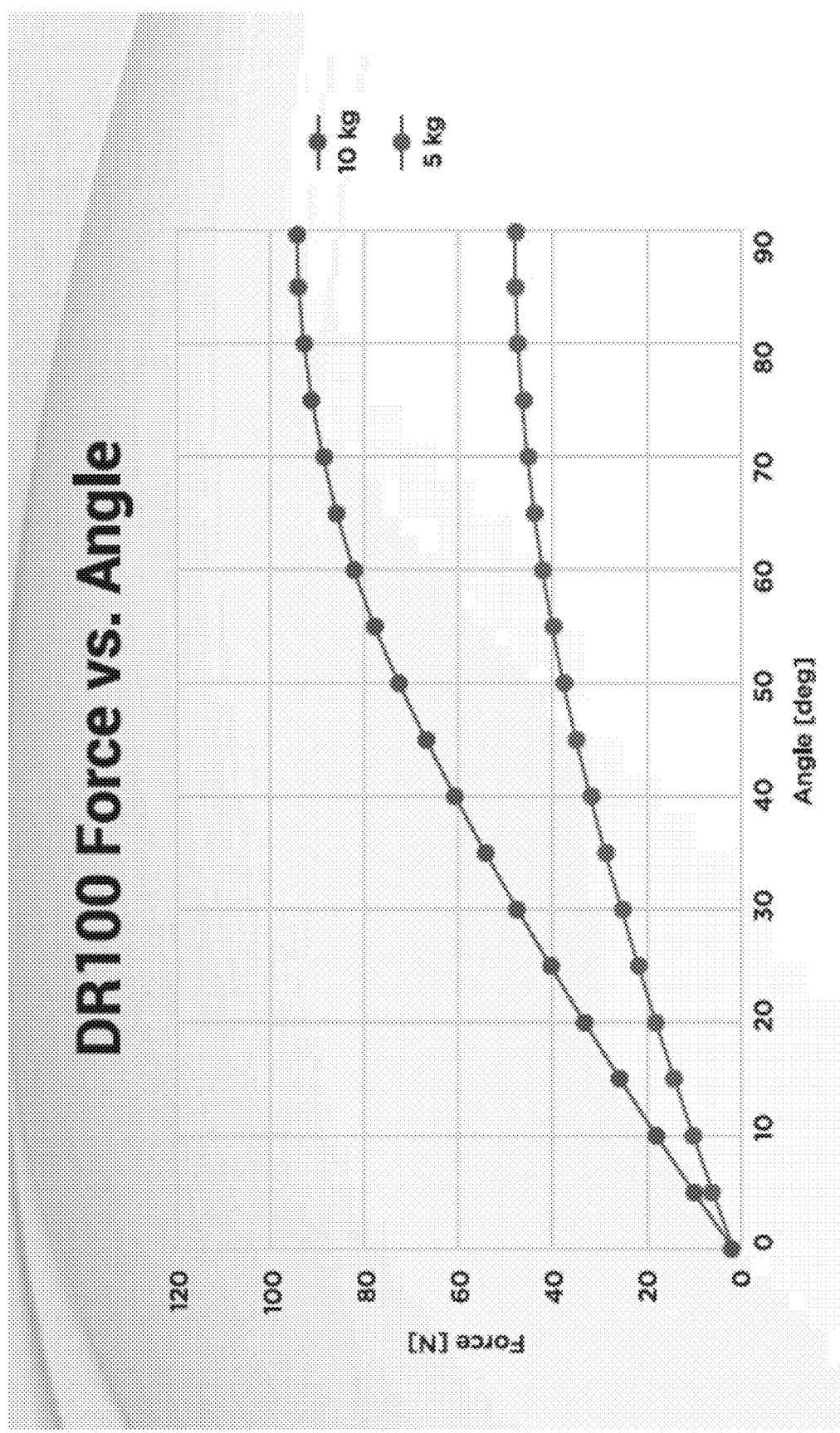
FIG. 10D is a graph of a function exhibited by the embodiment of FIG. 10A.

FIGS. 10A-10D show an embodiment of a spinal stability trainer apparatus that can be used to develop optimal coordination among the body's core posterior sector components. The machine features an industry grade steel construction, variable load option, safety limiters, antibacterial surfaces, precision motion sensors, balance and force plates, an IoT connected processing TFT touch screen and an NFC reader. As illustrated in FIG. 10B, performing exercises on this machine can target various body segments such as joints (cervical-thoracic junction, thoracic spine, thoracolumbar junction, lumbar spine, lumbosacral junction, lumboiliac junctions, lilac crests superior attachments), as well as ligaments such as anterior longitudinal, posterior longitudinal, thoracolumar fascia, quadratus lumborum fascia, paraspinalis retinacular sheath, ligament flava luborum, lumbosacral ligaments, llilumbar ligaments; and also target muscles such as longissimus capitis, spinalis cervicis, levatores costarum, longissimus thoracis, deep extensors (semispinails an dmultifidus, interspinalis lumborum, and lliocostalis lumborum). The machine is characterized by the force vs. angle dependence as illustrated in FIG. 10D, at 5 kg weight load and 10 kg weight load.

Figure 11D:
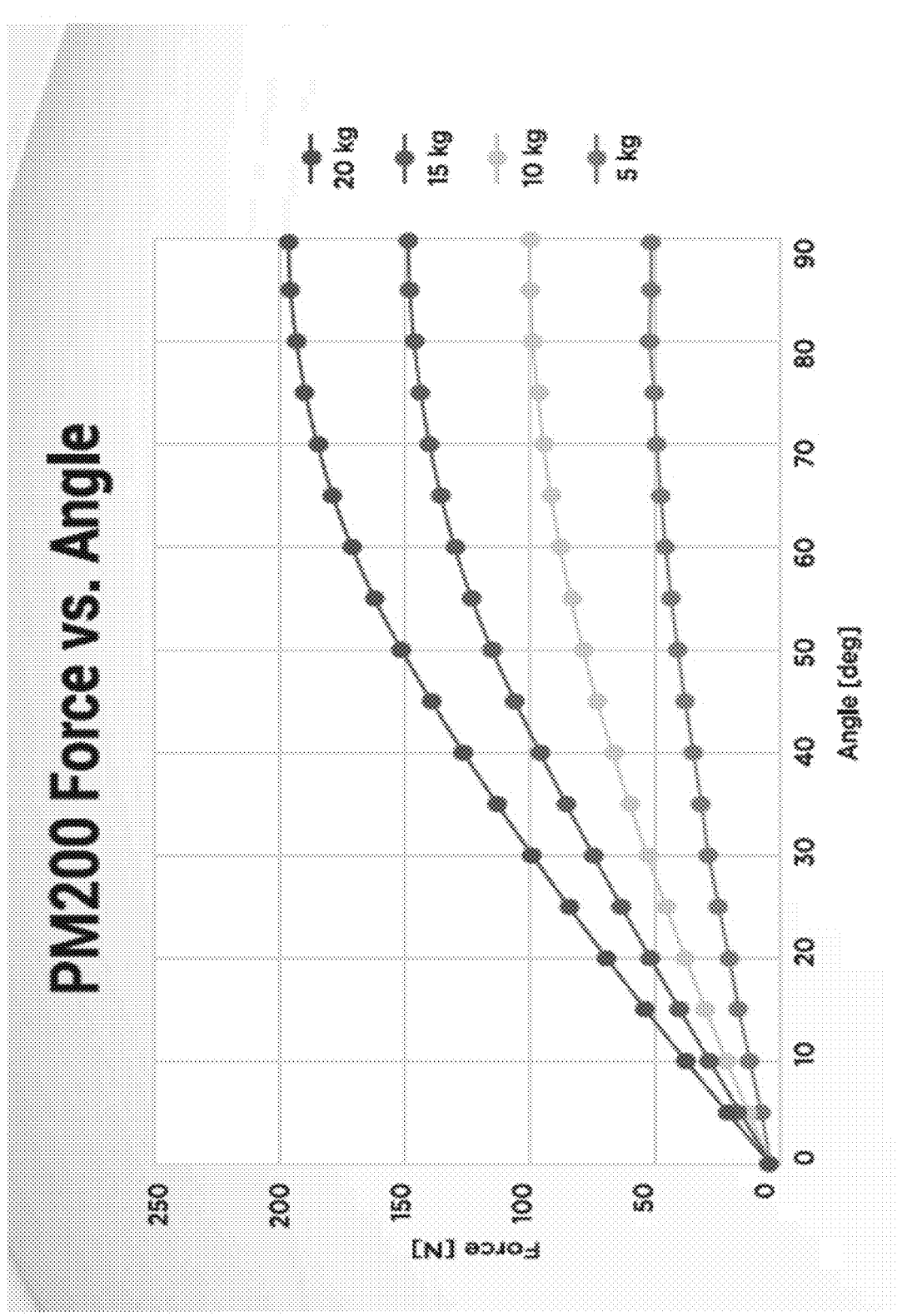
FIG. 11D is a graph of a function exhibited by the embodiment of FIG. 11A.

FIGS. 11A-11D and FIG. 2A illustrate an embodiment of a pelvic/spine trainer apparatus that can be used to develop optimal coordination among the body's core posterior sector components. The machine features a zero-friction pendulum, industry grade steel construction, safety support cushion, active cushion, antibacterial surfaces, precision motion sensors, balance and force plates, an IoT connected processing TFT touch screen and an NFC reader, as described above in detail, in the section of this specification related to FIG. 2A. As shown in FIG. 11B, performing exercises using this apparatus can target various body segments such as target joint (thoracolumbar junction, lumbar, lumbosacral junction, luboiliac junctions, lilac crests inferior attachments, and hips), as well as target ligaments such as anterior longitudinal, posterior longitudinal, quadratus lumborum fascia, gluteal aponeurosis, sacroiliac ligaments, lliolumbar, hip joint capsule, sacrococcygeal, sacrotuberous; and also target muscles such as deep extensors (spinalis and multifidus), quadratus lumborum, glutes, posas, lliacus, gemeliuses, obturator, and piriformis. The machine can be characterize by the force vs. angle dependence, as illustrated in FIG. 11D, using various weight loads ranging from 5 kg to 20 kg.

Figure 12A:
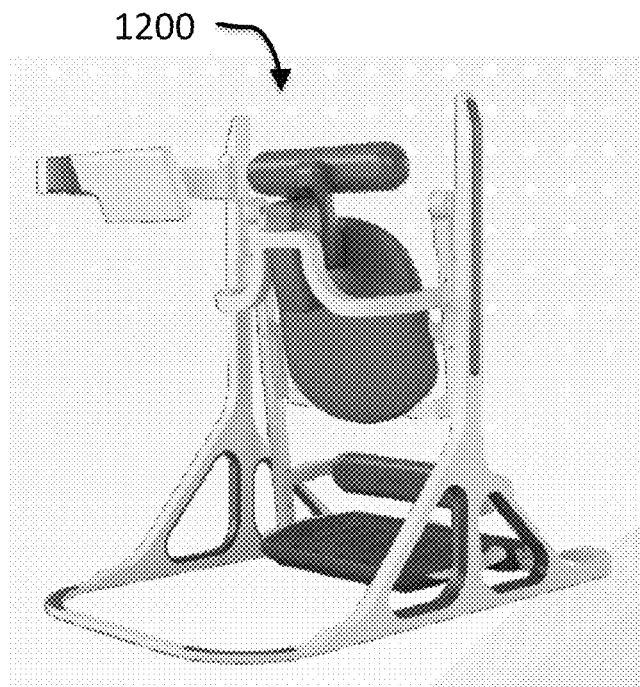
FIG. 12A is a schematic diagram of an embodiment of the disclosed system.
Figure 12B:
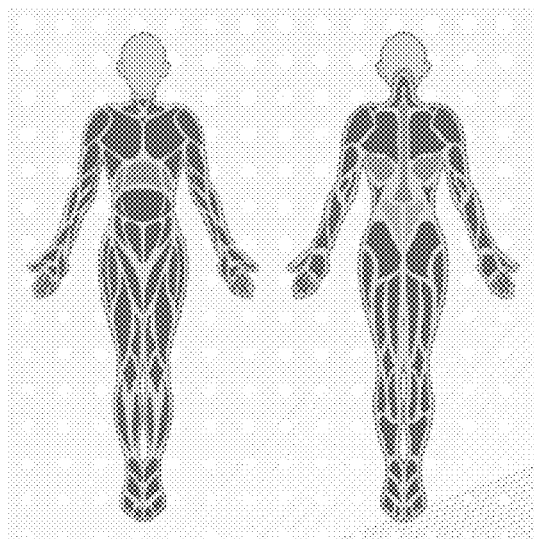
FIG. 12B is a schematic diagram showing body segments that can be targeted using the embodiment of FIG. 12A.
Figure 12C:
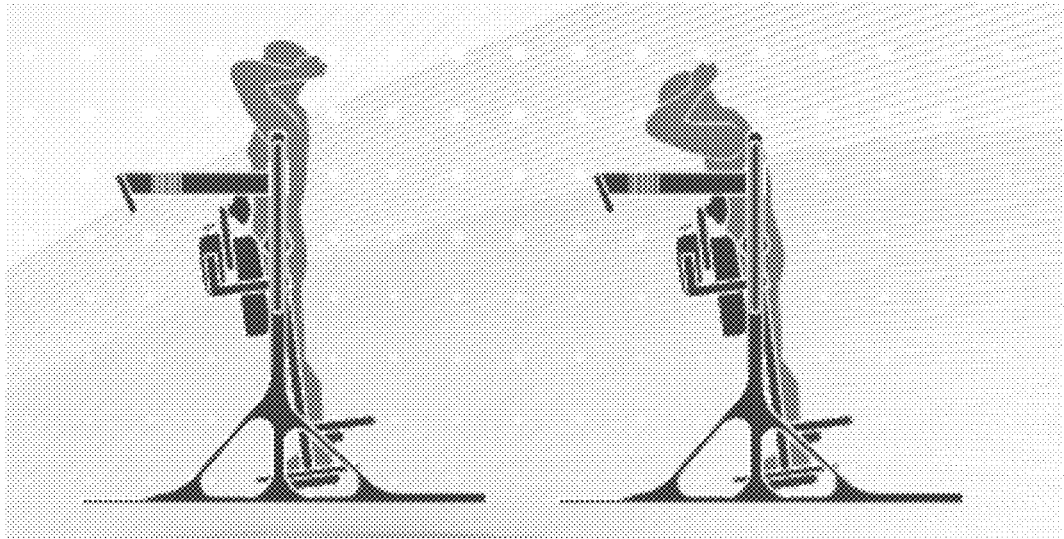
FIG. 12C is a schematic diagram showing the embodiment of FIG. 12A in action.
Figure 12D:
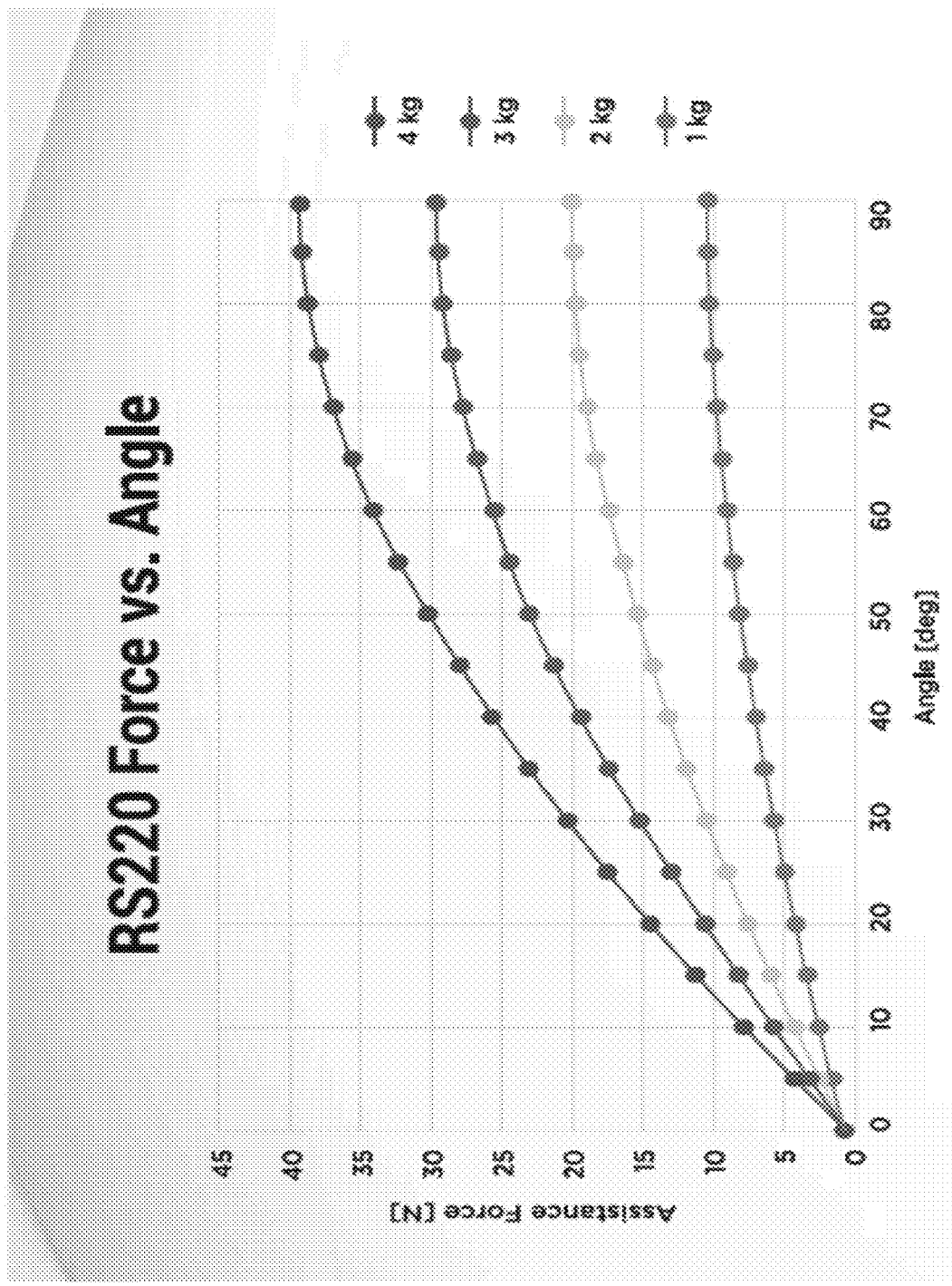
FIG. 12D is a graph of a function exhibited by the embodiment of FIG. 12A.

FIGS. 12A-12D illustrate an embodiment of a spine trainer exercise machine that can be used to develop optimal coordination among the body's core posterior sector components. The machine features an industry grade steel construction, safety support cushion, active cushion, antibacterial surfaces, precision motion sensors, balance and force plates, an IoT connected processing TFT touch screen and an NFC reader. As shown in FIG. 12B, performing exercises using this machine can target various body segments such as joints (cervical and thoracic spine, strenoclavicular, acromioclavicular, scapula, and scapulothoracic), ligaments such as anterior longitudinal, posterior longitudinal, nuchal, flaval, supraspinous interspinous, and also muscles such as infrahyoids, serratus posterior superior, rectus capitis, scalenes, trapezius, SCMs, and supraspinatus. The machine can be characterized by the force vs. angle dependence, as illustrated in FIG. 12D, using various loads ranging from 1 kg to 4 kg.

Figure 13A:
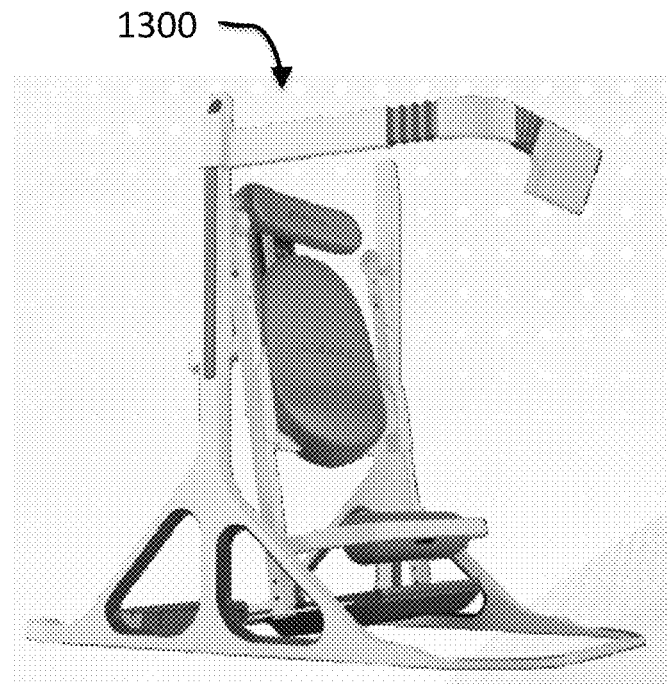
FIG. 13A is a schematic diagram of an embodiment of the disclosed system.
Figure 13B:
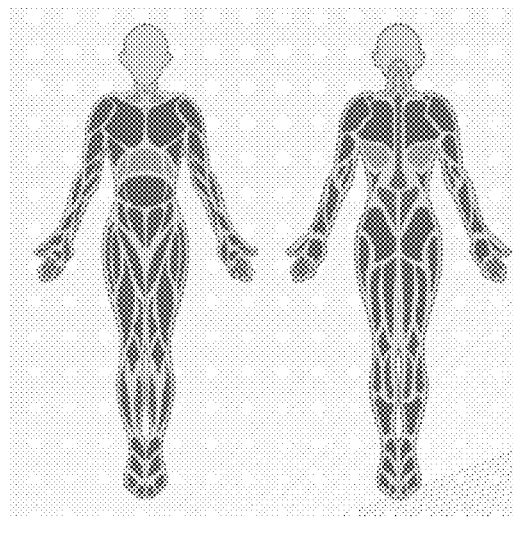
FIG. 13B is a schematic diagram showing body segments that can be targeted using the embodiment of FIG. 13A.
Figure 13C:
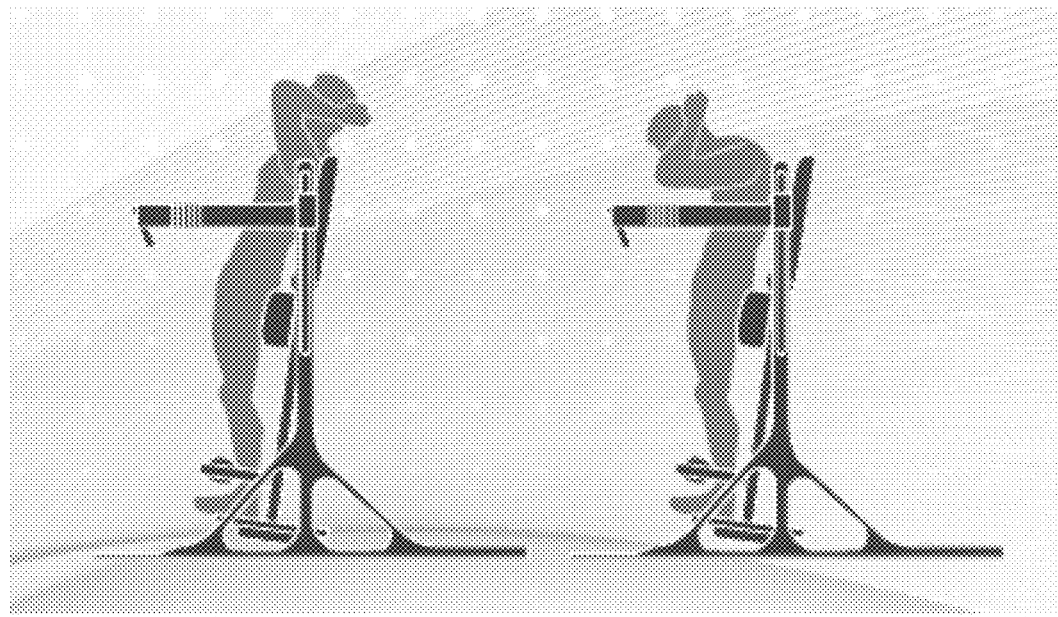
FIG. 13C is a schematic diagram showing the embodiment of FIG. 13A in action.
Figure 13D:
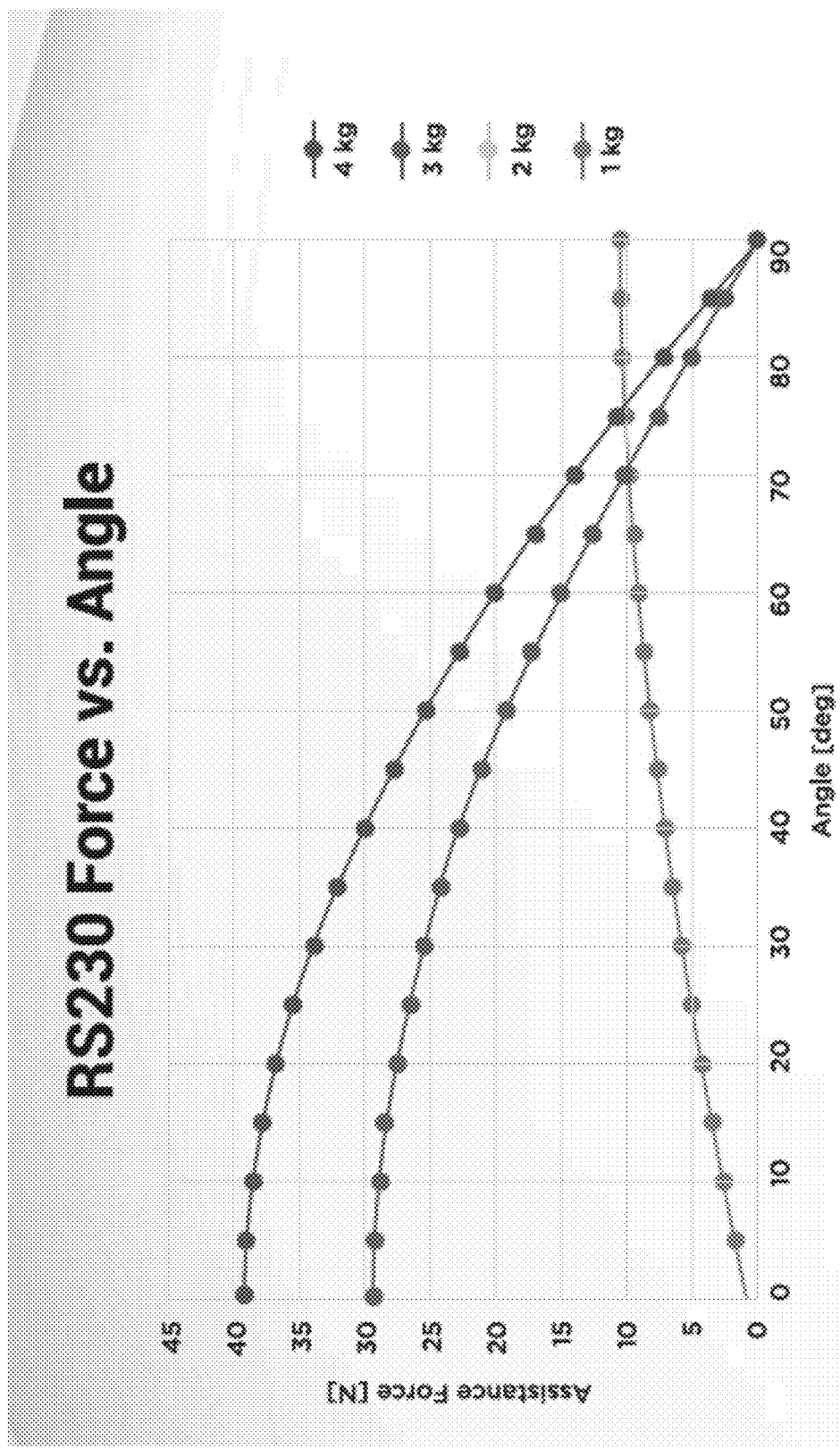
FIG. 13D is a graph of a function exhibited by the embodiment of FIG. 13A.
Figure 13E:
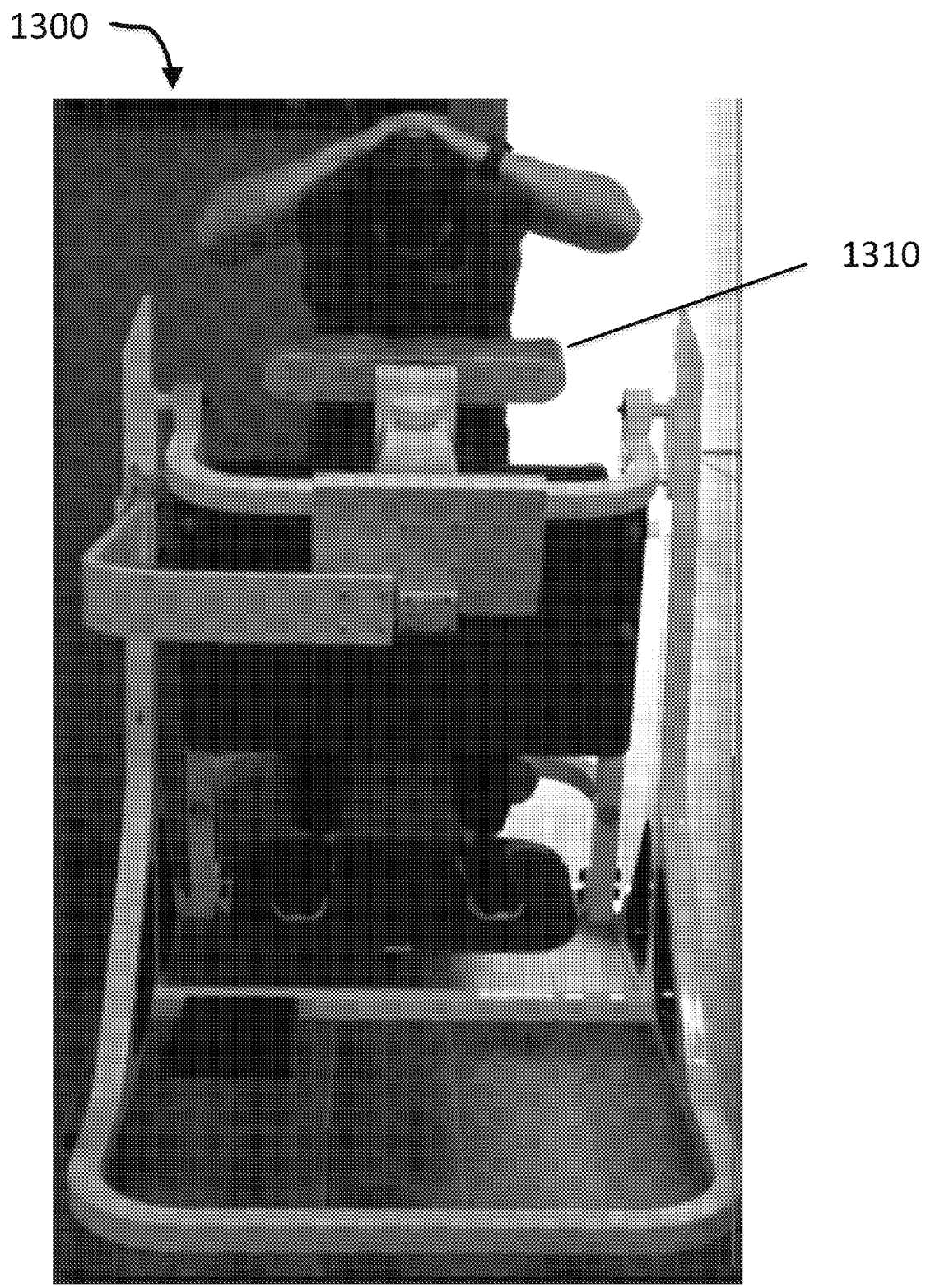
FIG. 13E is a schematic diagram of the embodiment of FIG. 13A, showing a motion limiter.

FIGS. 13A-13E illustrate an embodiment of a spine trainer exercise apparatus that can be used to develop optimal coordination among the body's core posterior sector components. The apparatus features an industry grade steel construction, safety support cushion, active cushion, antibacterial surfaces, precision motion sensors, balance and force plates, an IoT connected processing TFT touch screen and an NFC reader. As shown in FIG. 13B, performing exercises using this machine can target various body segments such as joint (upper and lower thoracic spine, lumbar spine, thoracolumbar junction, costovertebarals, lumbosacral junction), ligaments such as thoracolumbar fascia, supraspinous, anterior longitudinal, posterior longitudinal, quadratus lumborum fascia, interspinous, costotransverse; as wll as muscles such as semispinalis thoracic, multifidus, intercostals, qudratus luborum, lliocostalis, trapezius, serratus posterior inferior. The machines is characterized by the assistance force vs. displacement angle dependence, as shown in FIG. 13D, using various loads ranging from 1 kg to 4 kg. Some embodiments of the present invention employ motion limiters such as motion limiter 1310 shown in FIG. 13E, for primarily improving mobility of the thoracic spine.

Figures 14A, 14B:
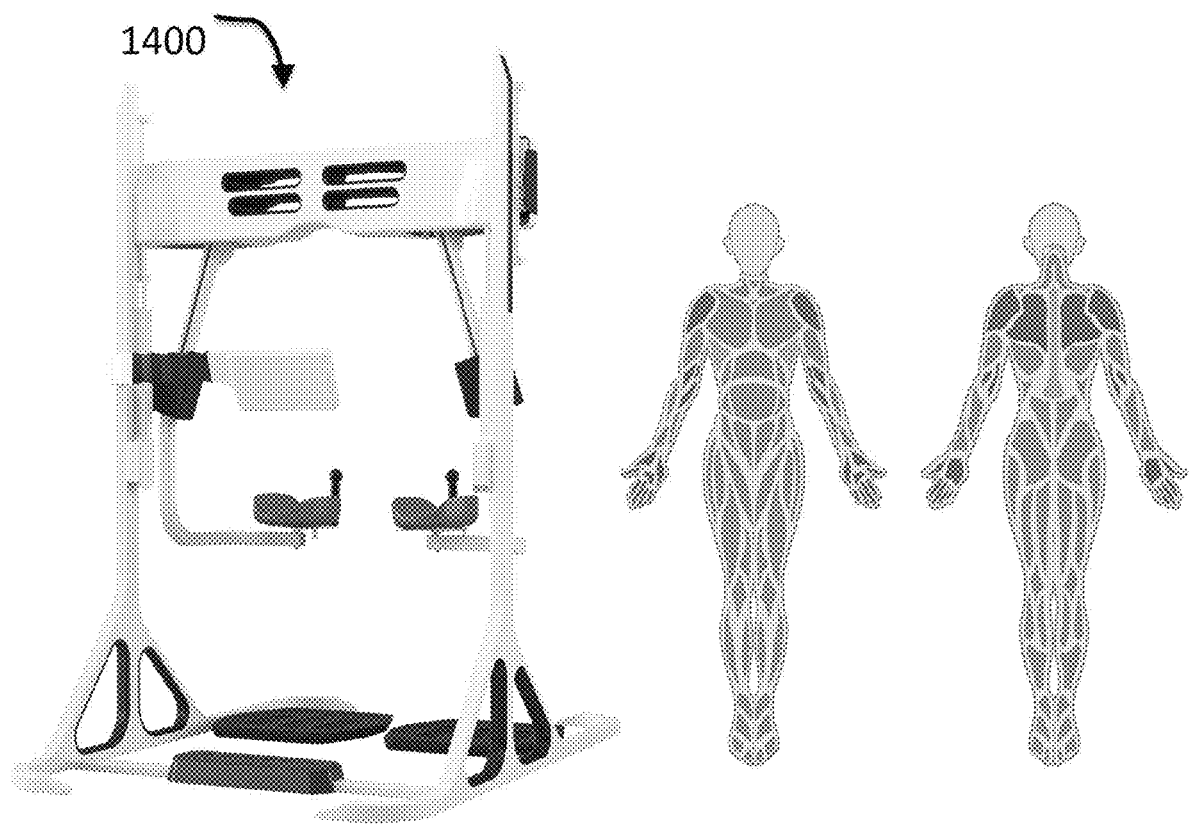
FIG. 14A is a schematic diagram of an embodiment of the disclosed system.
FIG. 14B is a schematic diagram showing body segments that can be targeted using the embodiment of FIG. 14A.
Figure 14C:
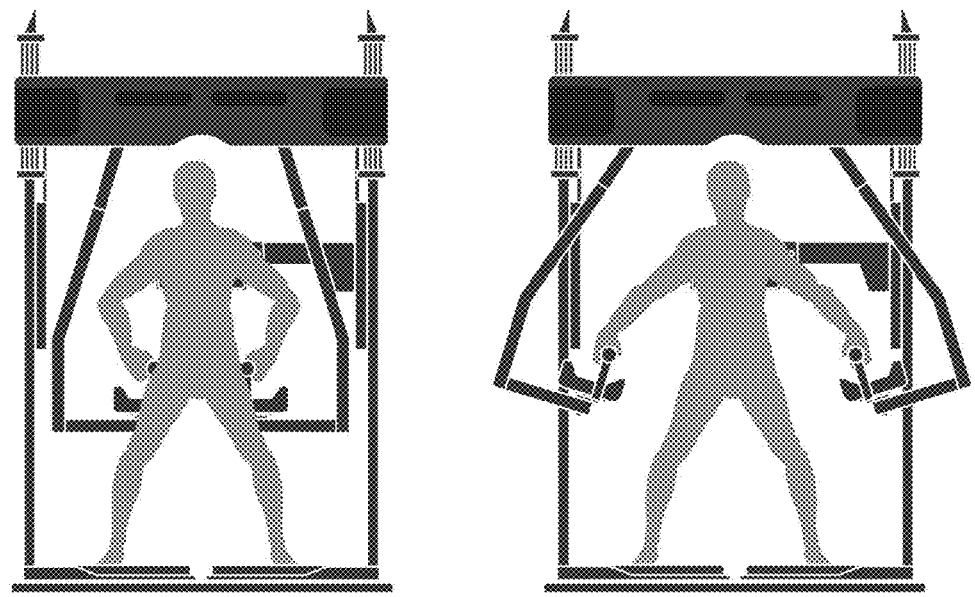
FIG. 14C is a schematic diagram showing the embodiment of FIG. 14A in action.
Figure 14D:
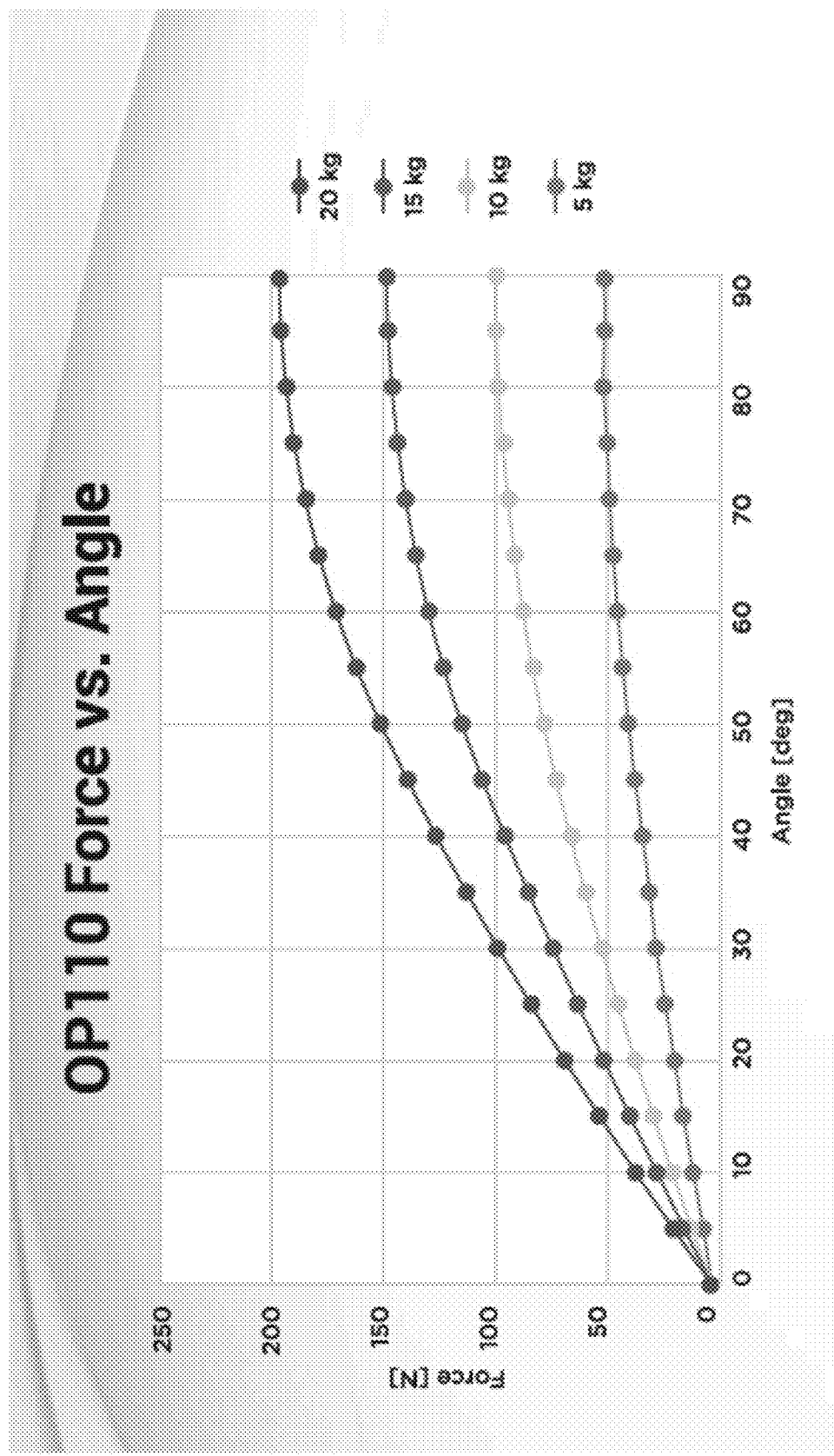
FIG. 14D is a graph of a function exhibited by the embodiment of FIG. 14A.

FIGS. 14A-14D illustrate an embodiment of a lateral shoulder trainer apparatus that can be used to develop optimal coordination among the body's core posterior sector components. The machine features two zero-friction pendulums, industry grade steel construction, safety support cushion, antibacterial surfaces, precision motion sensors, balance and force plates, an IoT connected processing TFT touch screen and an NFC reader. As illustrated in FIG. 14B, performing exercise on this machine can target various body segments such as joints (cervical-thoracic junction, medial border of scapula, superior border of scapula, glenohumeral joint, acromioclavicular joint, elbows, writs, and hands), ligaments (deep and superficial cervical fascia, glenohumeral joint capsule, acromioclavicular, coracoacromial, coracoclavicular, sternoclavicular, radial and ulnar collateral ligaments/elbows, dorsal wrist ligament) and muscles (serratrus posterior superior, trapezius, rhomboids, deltoids, levator scapulate, infraxpinatus, teres major and minor, supraspinatus, serratus anterior, triceps brachii, ankoneus, and wrist extensors). The machine can be characterized by the force vs. angle dependence, as shown in FIG. 14D, at various loads ranging from 5 kg to 20 kg.

Figures 15A, 15B:
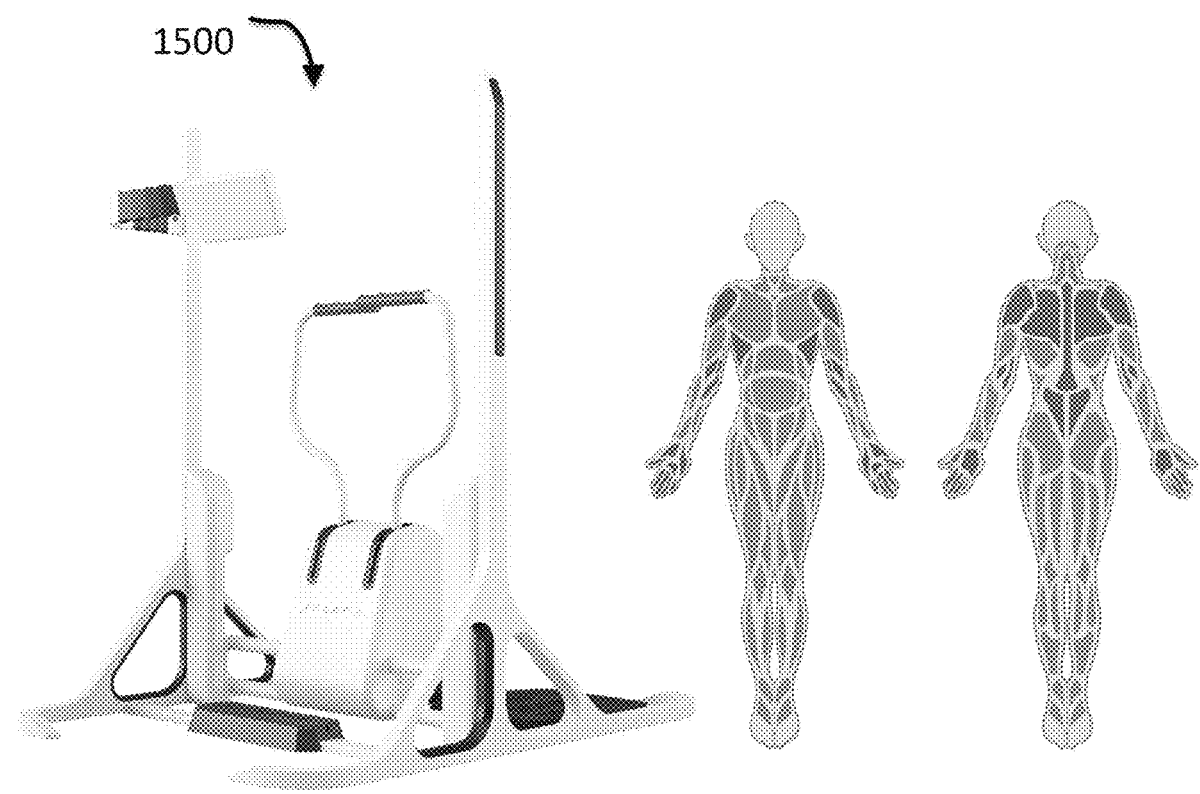
FIG. 15A is a schematic diagram of an embodiment of the disclosed system.
FIG. 15B is a schematic diagram showing body segments that can be targeted using the embodiment of FIG. 15A.
Figure 15C:
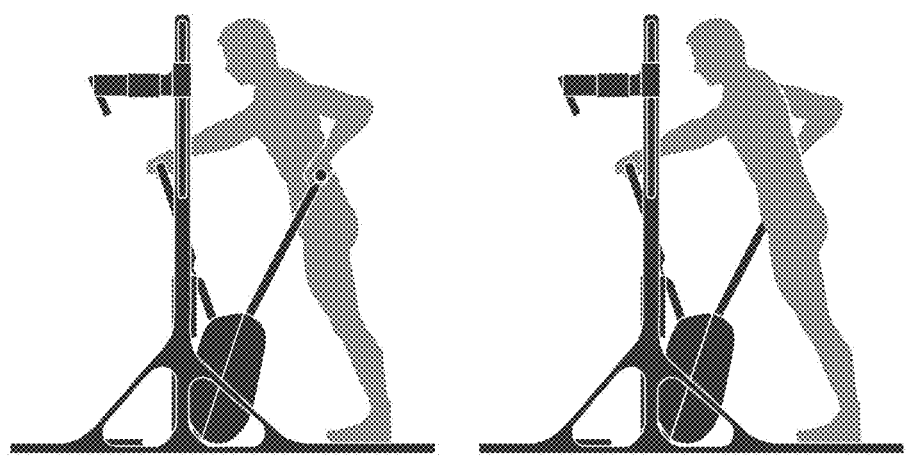
FIG. 15C is a schematic diagram showing the embodiment of FIG. 15A in action.
Figure 15D:
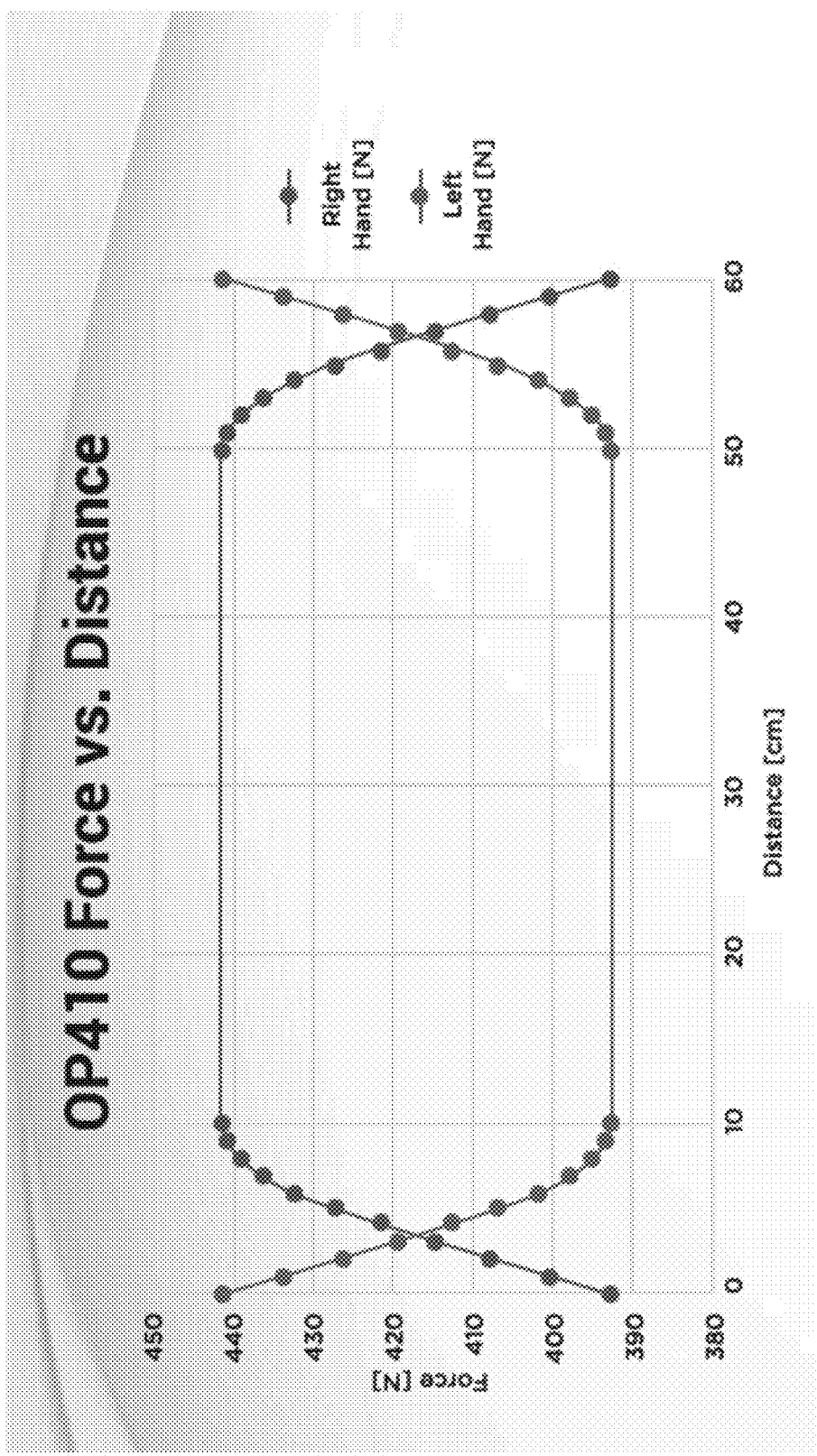
FIG. 15D is a graph of a function exhibited by the embodiment of FIG. 15A.

FIGS. 15A-15D illustrate an embodiment of a shoulder arch trainer apparatus that can be employed to develop optimal coordination among the body's core posterior sector components. The machine features an industry grade steel construction, hydraulic pendulums, antibacterial surfaces, precision motion sensors, balance and force plates, an IoT connected processing TFT touch screen and an NFC reader. Each pendulum is connected to an actuator to cause the pendulums to move back and forth to exert resistance to movement of the user's arms initiated by the user. In some instances the actuators are hydraulic actuators. In other instances the actuators can be pneumatic or electric, or some combination thereof. In some embodiments, each pendulum is connected to an actuator to assist the movement of the arms of the user engaging the pendulum. In some embodiments, each pendulum is coupled to two actuators, one actuator configured to assist the movement of the arms and another actuator configured to exert resistance to movement of the user's arms. In some embodiments a heart rate monitor sensor can be embedded in or attached to the handles of the exercise machine. As illustrated in FIG. 15B, performing exercises on this machine can target various body segments such as joints (cervical thoracic junction, medial border of scapula, glenohumeral joint, sternoclavicular joint, acromioclavicular joint, elbows, wrists, hands), ligaments (coracoclavicular, sternoclavicular, glenohumeral joint capsule, costotransverse ligaments, rotator cuff tendons, triceps tendon, radial and ulnar collateral ligaments/elbow/wrist, wrist flexor and extensor retinaculum), and muscles (erectors spinae, latissimus dorsi, serratus anterior, rhomboids, rotator cuff complex, coracobrachialis, pectoralis minor, tricepts brachii, forearm pronators and supinators). The apparatus can be characterized by the force vs. distance dependence for right hand and left hand, as shown in FIG. 15D.

FIGS. 16A-16D illustrate an embodiment of a torso/pelvis/legs trainer exercise machine that can be used to develop optimal coordination among the body's core posterior sector components. The machine features an industry grade steel construction, counter weight stack, back support cushion, antibacterial surfaces, balance and force plates, an IoT connected processing TFT touch screen and an NFC reader. As shown in FIG. 16B, performing exercise on this machine can target various body segments such as joints (lumbosacral junction, luboiliac junctions, lliac crests inferior attachments, hips, pelvic floor, knees, and ankles), ligaments (gluteal aponeurosis, lliolumbar ligaments, sacrococcygeal, sacrospinous, rectus sheath, lliofemoral, sacrotuberous, lliotibial band, patellar retinaculums and ligament, Achilles tendon), and muscles (erectors spinae iliocostalis and longissimus, glutes, pubococcygeal, tensor fasciae latae, llioposoas, piroformis, adductors, quadricepts, and gastrocnemius). The apparatus can be characterized by the assistance force vs. displacement dependence at various weight loads ranging from 25 kg to 125 kg, as shown in FIG. 16D. In some embodiments of the present invention, instead of a counterweight stack system, the machine can employ a rubber band mechanism operated by an electric motor. Referring to FIG. 16E that shows back side of the machine, seating platform 1602 is attached by cable 1605 to a counter balance rubber band system, which comprises top bar 1620*a* and bottom bar 1620*b* and one or more rubber bands 1610 coupled to the bars, wherein cable 1605 is attached to bar 1620*a* and electric motor 1630 is coupled to bar 1620*b* by a cable. In some embodiments, the system can comprise an additional bar, such as bar 1620*c* that is coupled to the motor and bottom bar 1620*b* by the cable. The electric motor is configured to adjust the distance between the bars stretching the rubber bands thereby increasing the resistance of the counter balance system. The rubber bands can be permanently attached to the bars, for example with glue, or can be releasably attached to the bars by stretching around the bars. According to some alternative embodiments of the present invention, one or more springs can be used instead of rubber bands.

In some embodiments, a neck device can be preferably used in conjunction with the machines shown in FIGS. 12A-12D and FIGS. 13A-13E, for example; or it can be used in connection with any other machines of the present invention. Referring to FIGS. 17A and 17B, neck device 1700 can be placed on a person performing various exercises on these machines. The neck device can comprise sensor 1710 embedded inside of the neck device, as shown in FIG. 17B. In some embodiments, the sensor can be releasably attached to the neck device. In some embodiments, the sensor can be permanently attached to the neck device. The sensor can be a gyroscope or accelerometer, or both. In some instances, the sensor can be a pulse meter sensor, temperature sensor, pressure sensor, heart rate monitor, or combination thereof. The sensor can comprise other sensors described throughout this specification. The sensor can be wired or wirelessly connected to the processor of the machine and is configured to measure the movements of the spine, wherein the sensor is preferably placed above the C7 vertebra thereby allowing to measure the motion of thoracic spine and disregard the motion of the head, as shown in FIG. 17B. The neck device can be a neck collar completely enclosing a neck of the user. In some embodiments, the neck device can be partially enclosed as shown in FIG. 17A. In some embodiments, the neck device can comprise one integral part (for example, it can be made by means of injection molding). In some embodiments, the neck device can have separate segments 1720, as shown in FIG. 17A. The segments can be detachable from each other or can be permanently secured. The detachable segments can have different weights, ranging from 1 kg to 4 kg, for example. The detachable segments can all have the same weight. In some embodiments the neck device can have one detachable segment. In some embodiments, the neck device can have more than one detachable segment. The neck device can be made of polyurethane plastic, stainless steel, silicone and rubber materials, or combination thereof. The parts can be detachably secured to one another using various attaching means such as hooks and loops, spring-loaded pins and corresponding openings, protrusions or tabs and corresponding indentations, for example. The parts can be movable in relation to each other, forming a shape that follows the curve of a back.

In some embodiments, the system 200 includes a display 214. The display 214 may be any device that converts an electrical signal into an image, including without limitation a light-emitting diode (LED) display, a liquid crystal display (LCD), a plasma screen, or a cathode-ray monitor. The display 214 may be coupled to the at least one sensor 201; that is, the display 214 may display the output of the at least one sensor 201 directly. In other embodiments, the display 214 is coupled to the processor 209. The display 214 may be used to provide a corrective motion to the user as described below in reference to FIG. 3A. The display 214 may be used to provide feedback to the user as described below in reference to FIG. 3A.

The system 200 may include a wireless identification device 215. The wireless identification device 215 may be any device by means of which an electric circuit can communicate with another electronic circuit, including without limitation a transceiver, a receiver, a transmitter, a transponder, and the like. The wireless identification device 215 may include a near-field communication (NFC) device. The NFC device may be a device that communicates with a corresponding device via radio frequency at short range; as a non-limiting example, the NFC device may be a passive radio frequency identification (RFID) tag or an interrogator for an RFID tag. In some embodiments, a user of the system 200 possesses an RFID tag or similar device that contains information identifying the user, from which the NFC device extracts the identifying information. The NFC device may be coupled to the processor 209, which may match the identifying information with user data stored in memory of the processor 209 or in memory of a remote device (not shown) in communication with the processor 209. In some embodiments, the information identifying the user is linked to additional user data, such as the user's name, age, height, weight, ethnicity, or sex. The user information may also include health history, exercise history, user concerns, and other information as described below in reference to FIG. 3A. The user may enter this information during a registration step using a web application, mobile app, or the like.

The system 200 may include a remote device 217 that communicates with the processor 209. For instance, the remote device 217 may be a computing device such as a tablet or workstation operated by a gym administrator. The remote device 217 may provide user information to the processor 209, for instance when the processor 209 receives user identifying information from a user. The processor 209 may convey information such as exercise motion data to the remote device 217 during or after the use of the exercise machine. Alerts may be sent to the remote device 217; for instance, if the sensor data from the at least one sensor 201 indicates that the user is performing the exercise motion or corrective motion in an unsafe or otherwise problematic way, an alert may notify an administrator or trainer by way of the remote device 217. The remote device 217 may enable an administrator or trainer to control the processor 209 by entering commands or data; this may include without limitation, modifying the exercise motion or corrective motion, sending a message to be displayed to the user on the display 214, or switching off one or more components of the system. In some embodiments, the exercise machine includes a call button 218 that when activated by the user causes the processor to relay a message to the remote device 217; the message may be a request for attention from a physical trainer, for instance, who may be operating the remote device 217. The call button 218 may be any manual data entry device, including without limitation a push button, a switch, a key, a touchpad, or a virtual button on a touchscreen.

Figure 3A:
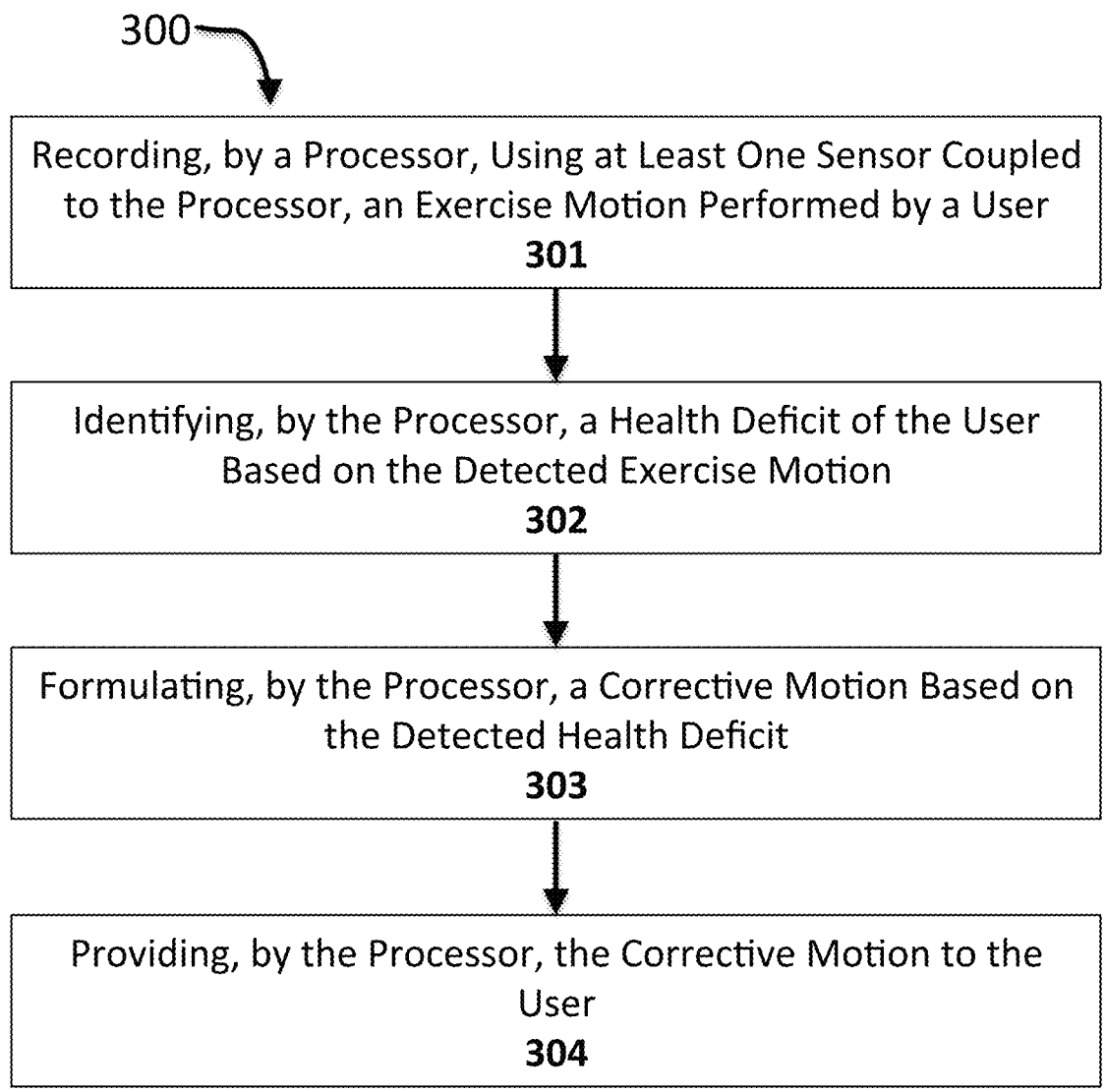
FIG. 3A is a flow diagram illustrating one embodiment of the disclosed method.
Figure 3B:
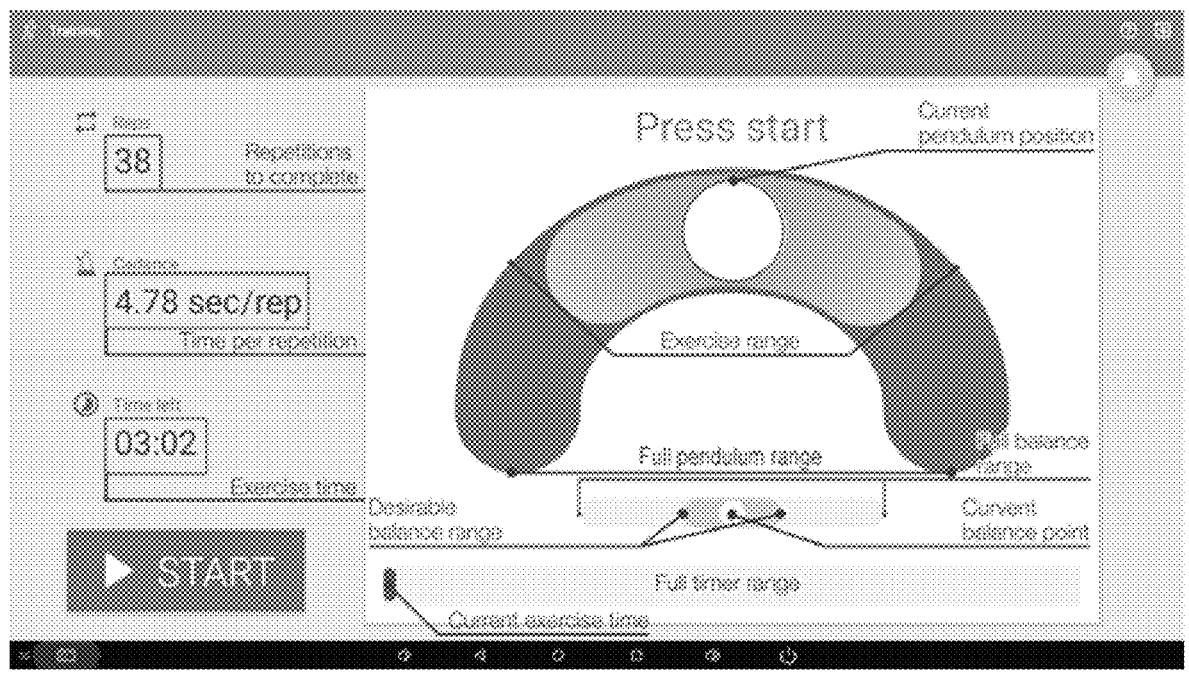
FIG. 3B is a screen capture illustrating one embodiment of a display presented to a user.

FIG. 3A illustrates some embodiments of a method 300 for identifying and correcting motion deficiencies through exercise. The method 300 includes recording, by a processor, using at least one sensor coupled to the processor, an exercise motion performed by a user (301). The method 300 includes identifying, by the processor, a motion deficiency of the user based on the detected exercise motion (302). The method 300 includes formulating, by the processor, a corrective motion based on the detected motion deficiency (303). The method 300 includes providing, by the processor, the corrective motion to the user (304).

Referring to FIG. 3A in greater detail, and by reference to FIGS. 2A-B, the processor 209 records an exercise motion. The exercise motion may include one or more movements or sets of movements that test the health and physical fitness of the user. The exercise motion may include, without limitation, simultaneous or separate leg extensions, spine pronation, arm extensions, squats, torso rotations, neck extensions, or any other physiologically safe and natural movement. As a further non-limiting example, the motions may involve any motion that target the following body segments in combination or separately (as an isolated example): (A) joints including (1) the thoracic spine; (2) the thoracolumbar junction; (3) the lumbar spine; (4) the lumbosacral junction; (5) the lumboiliac junctions; (6) the iliac crests superior attachments; or (7) hips; (B) ligaments including (1) the anterior longitudinal; (2) the posterior longitudinal; (3) aponeurotic roots of thoracolumbar fascia; (4) lumbosacral ligaments; (5) external oblique aponeurosis; or (6) quadratus lumborum fascia; (C) muscles including (1) deep extensors (spinalis thoracis and multifidus); (2) serratus posterior inferior; (3) glutes, internal and external; (4) obliques; (5) transversus abdominis iliocostalis lumborum; or (6) interspinalis lumborum.

In some embodiments, the exercise motion is selected by the processor 209 based on user data. For instance, the processor 209 or a remote device 217 may contain exercise motions that match users demographically, such as a different set of movements for older users than for younger users, or a different set of motions for men than for women. The processor 209 may also match the exercise motion to health and fitness information already recorded for the user; for instance, if the user has been involved in this method 300 or a similar method in the past, data may describe the user's past performance of an exercise motion, and the exercise motion in this case may be the same as or similar to that past exercise motion. Likewise, the user may enter information about the user's current state of health on a web application, mobile app, or other program that inputs user information; the user may enter information including but not limited to injury history, diagnoses of one or more injuries or maladies, exercise history, fitness or health goals the user possesses, or concerns the user has. The exercise motion may be selected based on this information; for instance, if the user is concerned about core strength or symmetry, the exercise motion may be selected to test core strength or symmetry.

Where the exercise motion is performed on an exercise device including a frame 202 and pendulum 203 as described above, the processor 209 may record the user swinging the pendulum 203 through an arc. For example, the user may stand on the platform 206 and holding the frame 202 swing his or her legs or legs and torso along with the pendulum. The processor 209 may record the pressure the feet of the user exerts on the platform 206 using at least one pressure sensor 207. The processor 209 may record the acceleration of the pendulum 203 using at least one accelerometer 208*a*. The processor 209 may record the change in orientation of the pendulum 203 using at least one gyroscope 208*b*. The exercise motion may be a motion besides swinging a pendulum; for instance, the user may squat on a platform having pressure sensors, or stand on a platform having pressure sensors while sitting against a wall.

In some embodiments, the system 200 informs the user what exercise motion to perform. In some embodiments, the system 200 informs the user how to perform the exercise motion. The system 200 may inform the user using the display 214. For instance, in some embodiments where the exercise motion is performed on the pendulum 203, the display 214 may indicate to the user how far to swing the pendulum in either direction. The display 214 may indicate to the user how many times to swing the pendulum. The display 214 may indicate to the user how rapidly to swing the pendulum 203, or how many times to complete a swing in a particular time period such as a minute. This may be performed as described below in reference to FIG. 3B. Similarly, the display may indicate to the user to perform a squat or other exercise, verbally or using images.

The processor 209 may record the exercise motion by recording pressure applied by the user on at least one pressure sensor; for instance, the at least one pressure sensor 207 may be in the platform 206, and may record the force with which the user presses down on the platform during a pendulum swing, squat, or other exercise. In some embodiments, the processor 209 uses the at least one pressure sensor 207 to record distribution of pressure between two limbs of the user during the exercise motion. For instance during the pendulum swing or squat, the user may exert more pressure on the pressure sensor 207 under the user's right foot than on the pressure sensor 207 under the user's left foot; this may indicate uneven weight distribution. Similarly, in an exercise motion in which the user is pressing with both arms against an object containing pressure sensors, the user may press more forcefully with one arm than the other. The processor 209 may record this information.

In some embodiments, recording the exercise motion includes recording an acceleration of the exercise motion. The processor 209 may use one or more accelerometers 208*a* to record the acceleration. In some embodiments, recording the exercise motion also includes recording a change in orientation of the exercise motion. The processor 209 may use at least one gyroscope 208*b* to record the change in orientation. The at least one motion sensor 208 may record more subtle data as well; for instance, the at least one accelerometer 208*a* may record vibration, and thus detect the vibration of an exhausted muscle of the user, which may indicate fatigue.

The method 300 includes identifying, by the processor, a motion deficiency of the user based on the detected exercise motion (302). In some embodiments, the processor 209 compares the recorded exercise motion to baseline data. The baseline data may be a set of parameters representing a desired level of performance of the exercise motion. The baseline data may include any expected sensor data consistent with the desired level of performance, including without limitation data concerning negative or positive acceleration, data concerning a path traversed during the exercise, data concerning overall pressure on pressure sensors, and data concerning pressure distribution. The baseline may be produced by recording an earlier exercise motion by the user; for instance, if the user performed the exercise motion at a time when the user was known to be free from injury or was in good athletic form, the sensor data from that performance may be used to determine whether the user's current performance has changed, indicating an injury or loss of ability. The baseline may be produced by recording an earlier exercise motion by another user; the other user may be an athlete or trainer, or another user who is known to be fit and to perform the exercise effectively. The other user may be demographically matched to the user; for instance, the baseline data may be acquired from a performance of the exercise motion by a user who is in the same age group as the user. The baseline data may be acquired from a performance by a user who is of the same sex or gender as the user. The baseline data may be acquired from a performance by a user who from the same ethnic group as the user. The baseline data may be acquired from a performance by a user having a similar body type to the user. This may be accomplished by having users meeting various demographic categories who are known to be healthy perform the In other embodiments, the baseline is created by recording a plurality of exercise motions by a plurality of users and aggregating the plurality of recorded exercise motions to produce the baseline. Each of the plurality of exercise motions may be the same as the exercise motion performed by the user. The baseline may be produced from the plurality of exercise motions by averaging the sensor data recorded from each of the plurality of exercise motions, for instance by computing an arithmetic or geometric mean. As an example, the acceleration detected by the at least one accelerometer at the a given point in the exercise motion for each or the plurality exercise motions may be averaged with the acceleration detected at the corresponding point in each of the remaining exercise motions of the plurality of exercise motions. The users that performed the plurality of exercise motions may be matched demographically to the user as described above. In some embodiments, the plurality of exercise motions is performed by users known to be fit enough to perform the exercise motion effectively; in other embodiments, the users are chosen as a representative sample of the demographic to which the user is matched, comparing the user to average performance in that demographic.

In other embodiments, the baseline is created using one or more ideal performance characteristics. An ideal performance characteristic may a sensor reading or set of sensor readings corresponding to a desired performance of the exercise motion. As an example, one exercise motion intended to test the strength of a user may include placing both feet on the platform 206, swinging the pendulum 203 upward to the front or back, swinging the pendulum back down to a vertical or zero-potential energy orientation, and stopping at the zero potential energy point; the ideal stopping point, indicating optimal strength under the test, may be right at the zero potential energy point. Thus, the data representing the stopping point in the ideal baseline may be right at the point in the pendulum arc where there is zero potential energy. Similarly, a perfect performance of the strength test may be one in which the weight of the user remains evenly distributed between the left and right feet throughout the exercise, and so in the ideal baseline the pressure sensor readings from pressure sensor under the right and left feet may be the same as each other.

In some embodiments, the processor 209 identifies a motion deficiency by comparing the data obtained from the user's performance of the exercise motion to the data in the baseline. The processor 209 may compare one or more sensor readings to the corresponding datum in the baseline; for instance, in the above-described strength test, if the user stops the pendulum after it has swung past the point in the baseline corresponding to cessation of movement by the pendulum, the processor 209 may determine that the user performance of the strength test indicated insufficient strength. The degree to which the user allowed the pendulum to travel past the baseline cessation point may be used to generate a score indicating the degree of the user's strength deficiency. Likewise, if the baseline indicates swinging the pendulum through a certain range of motion, the user's failure to match the range of motion may indicate a deficit in range of motion for the user, and the degree to which the user failed to reach the extremes of the range of motion may be used to generate a score indicating the severity of the range of motion deficit.

The baseline may also call for a certain number of repetitions of the exercise motion to be performed in a certain amount of time; in that case, if the user begins performing the exercise motion well but then slows down or ceases to be able to perform up to the baseline, the processor 209 may determine that the user has insufficient stamina.

In some embodiments, identifying the motion deficiency involves comparing a first parameter of the detected exercise motion to a second parameter of the detected exercise motion. For instance, where the exercise motion involves moving two arms or legs independently, detecting a motion deficiency may involve detecting that one arm or leg has performed differently from another; a first arm or leg may accelerate more slowly than its counterpart, for example. Likewise, the load cell or load cells may detect greater pressure on one side than on the other, indicating uneven weight distribution or uneven application of strength by the user during the exercise motion. Thus, comparison of a first parameter of the exercise motion to a second parameter of the same exercise motion may permit the processor 209 to determine that there is an asymmetry or lack of balance in the performance of the exercise. In some embodiments, can also identify an injured or deficient body part or kinetic chain. For instance, if the user's right arm is substantially weaker than the user's left arm, this may indicate that the user's right arm is lacking in strength or injured. The comparison may also include baseline data; for instance, where the user's right arm produces substantially less acceleration than the user's left arm, and the user's left arm is performing well as compared to the baseline, the processor 209 may determine that the user's right arm has the deficiency, whereas if the left arm is also not matching the baseline, each arm may have a distinct issue.

In some embodiments, identifying the health issue involves determining a quality of motion of the exercise motion. In some embodiments, determining the quality of motion involves assessing the ability to replicate a given target range for motion in a given time frame. In some embodiments, determination of quality of motion involves determination of how well the user can continue to control their motion over time. For instance, the exercise motion may require causing a pendulum to traverse a certain angle a certain number of times in a given time-period; if the fails to cover the range of motion for each repetition, or fails to perform the required number of repetitions, or both, the processor 209 may determine that quality of motion is lacking. The motion assessed may be selected based on fundamental muscle groups or fundamental kinetic chains, such as those most important for basic mobility, or as a foundation for athletic motion.

Identifying the motion deficiency may involve determining symmetry of the detected exercise motion. This may involve determining that the user can traverse a greater range of motion with one side than with the other side; for instance, an assessment of symmetry may determine that the right hand or leg can swing a pendulum through 35 degrees, while the left can only swing through 20 degrees. Likewise, the symmetry assessment may involve a detection of differences in strength; for instance, the right arm or leg may exert 30 pounds of pressure on a load cell, while the left arm or leg exerts only 25 pounds of pressure. The symmetry assessment may also involve determining a load balance of the detected exercise motion; for instance, the user may lean to one side or the other, creating different pressure sensor readings on the two sides. From this the processor 209 may determine how the user distributes the weight, when standing or during an exercise. Likewise, load cell data may inform the processor 209 how the user distributes pressure when pushing against a wall or other object (this can also be detected by pressure cells the user is standing on); this may involve pressing with both sides (e.g. both arms) simultaneously or alternately.

In some embodiments, identifying the motion deficiency also involves determining a range of motion of the user based on the detected exercise motion. For instance, gyroscopes may be used to determine the angle through which a pendulum is brought during the exercise motion. As noted above, the processor 209 may determine in which direction the user fails to match a baseline range of motion, and the degree to which the range of motion of the exercise motion is deficient.

In some embodiments, identifying the motion deficiency further comprises determining strength of the user based on the detected exercise motion. In some embodiments, the strength assessment is accomplished by measuring direct pressure, for instance with a dynamometer, where the user presses on something and the dynamometer is recording a change (e.g. voltage change in load cell). Strength may alternatively be assessed using the user's ability to move a pendulum or similar device through certain angles in certain ways. For instance, when the user is braced at waist level, holds handles in hands, and swings both legs back on a pendulum, then forward again, the user's lumbar/hamstring strength may be determined by the user's ability to stop the pendulum at the zero degree point, as noted above.

Figure 3C:
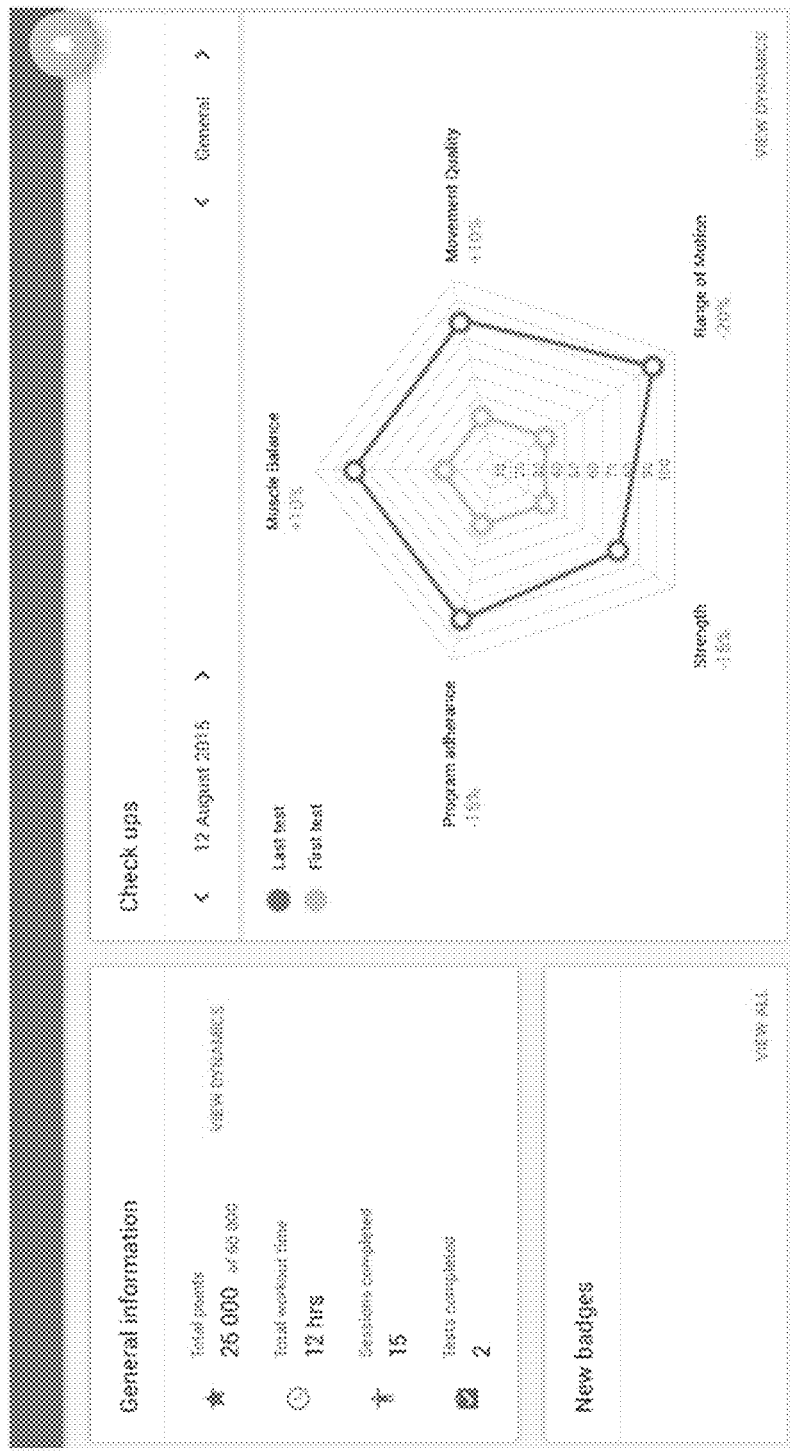
FIG. 3C is a screen capture illustrating one embodiment of a display presented to a user.

The above assessments may be combined to determine an overall score; the overall score may be presented graphically as shown for example in FIG. 3C. The graphic may compare each score the user achieved to a scale with higher numbers indicating better performance; subsequent performances showing improvements may be presented on the graphic as discussed in further detail below.

The method 300 includes formulating, by the processor, a corrective motion based on the detected motion deficiency (303). In some embodiments, the processor 209 formulates the corrective motion in part by creating a user baseline using the detected exercise motion; the baseline may be created as described above for creating a baseline for assessment of the exercise motion. The user baseline may be compared to subsequent exercise motions by the user as described above to track process; the measurement may be presented to the user, for instance as shown in FIG. 3C. In some embodiments, the user baseline is created by recording at least one second exercise motion and aggregating the first exercise motion and the at least one second exercise motion to create the user baseline. The aggregation may be performed by averaging as described above for aggregating exercise motion performance for the creation of a baseline; thus the baseline may be created by computing the average value of one or more parameters from the exercise motions.

In some embodiments, the corrective motion requires the user to match one or more parameters of the user baseline. The corrective motion may require the user to perform an exercise motion at the level of performance the user demonstrated periodically, gradually improving the user's performance. In other embodiments, the corrective motion requires the user to exceed one or more parameters of the user baseline; for instance, the corrective motion may call for the user to reach the user's average range of motion, or just beyond. The user may be required to perform the exercise motion at the maximum parameters previously achieved by the user. In some embodiments, requiring the user to attempt exercise motions that are slightly beyond the user's measured performance enables the user to improve the user's physical condition by striving to improve in small increments.

In some embodiments, formulating the corrective motion involves periodically updating the user baseline based on at least one subsequent exercise motion. The user baseline may be updated by averaging all past performances of the exercise motion by that user. The user baseline may be updated by discarding the previous baseline and basing the current baseline on the latest exercise motion the user has performed; in some embodiments this is done only if the latest exercise motion represents an improvement over the previous baseline. In some embodiments, the corrective motion is periodically updated to bring parameters the user must perform closer to parameters matching the ideal exercise motion for the user, or closer to parameters matching the baseline to which the user's exercise motion was initially compared. The processor may also create a schedule for the user to follow. For instance, the corrective motion may be included in a program that requires the performance of at least one corrective motion on a regular basis, with incremental improvements, until the user's exercise motion is within some margin of error of the ideal motion.

The method 300 includes providing, by the processor, the corrective motion to the user (304). In some embodiments, providing the corrective motion to the user involves displaying the corrective motion to the user. The display of the corrective motion may include a verbal description of steps to follow. The display of the corrective motion may include a graphical depiction of the corrective motion. For example, displaying the corrective motion to the user may involve displaying a path for user to follow while performing the corrective motion; in one embodiment, where the corrective motion is to be performed on a pendulum 203, the path to follow may be an arc as shown for instance in FIG. 3B. The arc may display in a first color or texture showing the full possible range of motion of the pendulum 203, and a second color or texture showing the fraction of that full range that the user is expected to traverse. The corrective motion may similarly be provided to the user by means of a web application, mobile application, or other program operating on a remote device such as a computer, tablet, or smartphone.

The method 300 may further involve providing feedback as the user performs the corrective motion. The feedback may involve displaying the results of the user's actions after the performance of the corrective motion, for instance as shown in FIG. 3C. In other embodiments, the user's performance is displayed to the user in real time, with a comparison to the desired corrective motion. For instance, the display 214 may display a cursor indicating the current position of the user along the path of the corrective motion. As a non-limiting example, a cursor (e.g., a white circle) indicating the current position of the pendulum within the full range of motion of the pendulum may track the user through the arc the user describes within the pendulum; the user may thus view whether the user is covering the full arc required by the corrective motion, and not exceeding that arc. The processor 209 may continue to track any assessments described above for identifying the motion deficiency, by performing the assessments with regard to data collected while the user performs the corrective motion; the updated assessments may be compared to the initial assessments to track the user's progress. The user may be authenticated at each session using the wireless identification device 215. In other embodiments, an administrator uses a tablet to register new users in the gym, or monitor existing users. User feedback may similarly be provided to the user by means of a web application, mobile application, or other program operating on a remote device such as a computer, tablet, or smartphone.

Figure 4:
FIG. 4 is a flow diagram illustrating one embodiment of the disclosed method.

FIG. 4 illustrates some embodiments of a method 400 for identifying and correcting motion deficiencies through exercise. The method 400 includes recording, by an exercise device comprising a frame and a pendulum having a proximal end journaled on the frame and a distal end, using at least one sensor, an exercise motion comprising the user moving the pendulum (401). The method 400 includes identifying, by the exercise device, a health deficit of the user based on the detected exercise motion (402).

Referring to FIG. 4 in greater detail, and by reference to FIGS. 2A-B, the method 400 includes recording, by an exercise device comprising a frame and a pendulum having a proximal end journaled on the frame and a distal end, using at least one sensor, an exercise motion comprising the user moving the pendulum (401). This may be implemented as described above in reference to FIG. 3A. The pendulum and frame may be any pendulum 203 and frame 202 described above in reference to FIGS. 2A-B; the pendulum and frame may be incorporated in any exercise machine as described above in reference to FIGS. 2A-B.

The method 400 includes identifying, by the exercise device, a motion deficiency of the user based on the detected exercise motion (402). This may be implemented as described above in reference to FIG. 3A.

The method 400 may also include formulating, by the processor, a corrective motion based on the detected health deficit. This may be implemented as described above in reference to FIG. 3A.

The method 400 may also include providing, by the processor, the corrective motion to the user. This may be implemented as described above in reference to FIG. 3A. The exercise machine may also record the user performing the corrective motion, provide user feedback, or perform any other step described above in reference to FIG. 3A.

Although the foregoing systems and methods have been described in some detail for purposes of clarity of understanding, it will be apparent that certain changes and modifications may be practiced within the scope of the appended claims.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

Although the invention is described herein with reference to specific embodiments, various modifications and changes can be made without departing from the scope of the present invention as set forth in the claims below. Accordingly, the specification and figures are to be regarded in an illustrative rather than a restrictive sense, and all such modifications are intended to be included within the scope of the present invention. Any benefits, advantages, or solutions to problems that are described herein with regard to specific embodiments are not intended to be construed as a critical, required, or essential feature or element of any or all the claims.

Unless stated otherwise, terms such as "first" and "second" are used to arbitrarily distinguish between the elements such terms describe. Thus, these terms are not necessarily intended to indicate temporal or other prioritization of such elements.

The foregoing detailed description is merely exemplary in nature and is not intended to limit the invention or application and uses of the invention. Furthermore, there is no intention to be bound by any expressed or implied theory presented in the preceding technical field, background, brief summary, or the following detailed description.

What is claimed is:

1. A method for identifying and correcting motion deficiencies through exercise, the method comprising:
    providing a system for identifying and correcting motion deficiencies through exercise, the system comprising:
        a processor;
        a frame;
        a pendulum having a proximal end journaled on the frame and a distal end;
        a platform at the distal end of the pendulum, the platform sized to accommodate both feet of a user;
        a plurality of pressure sensors incorporated into the platform and a plurality of motion sensors, wherein the plurality of pressure sensors and the plurality of motion sensors are configured to sense an exercise motion performed by a user standing on the platform, thereby the plurality of pressure sensors and the plurality of motion sensors are incorporated into the pendulum;
    a display coupled to the processor, wherein the processor is coupled to the plurality of pressure sensors and the plurality of motion sensors, wherein the plurality of pressure sensors and the plurality of motion sensors collect data on a position of the user and balance at every segment of time;
    using the plurality of motion sensors and the plurality of pressure sensors coupled to the processor to record the exercise motion of the user;
    determining a weight distribution on the platform by recording pressure applied by the user on the plurality of pressure sensors and recording a distribution of pressure between two limbs of the user during the exercise motion;
    assessing if the exercise motion is able to stop and accelerate the pendulum at precise endpoints of a path corresponding to the exercise motion to determine quality of the recorded exercise motion;
    counting an amount of times an angle of the pendulum is traversed in a given time period when determining repetitions of the exercise motion and the quality of the recorded exercise motion;
    generating a baseline data;
    comparing the recorded exercise motion to baseline data;
    identifying a motion deficiency of the user, based on feedback from both the pressure sensor and the motion sensor and the baseline data;
    formulating, by the processor, a corrective motion based on the motion deficiency; and
    displaying the corrective motion as a graphical depiction, wherein the graphical depiction comprises: a path for the user to follow when performing the corrective motion with a cursor displaying a current position, while keeping the balance, in a given timeline, wherein:
    the path for the user to follow corresponds to a desired motion of the pendulum,
    the cursor corresponds to the current position along a path of the pendulum when providing the feedback as the user performs the corrective motion, and
    wherein the balance corresponds to the weight distribution between the two limbs and the timeline corresponds to a rate or amount of time per repetition.

2. The method of claim 1, wherein recording the exercise motion further comprises recording the user swinging a pendulum through an arc.

3. The method of claim 1, wherein recording the exercise motion further comprises recording the user performing a squat.

4. The method of claim 1, wherein recording the exercise motion further comprises:
    recording an acceleration and deceleration of the exercise motion; and
    recording a quality of execution of the exercise range between the two exercise motion return points.

5. The method of claim 1, wherein recording the exercise motion further comprises detecting muscle vibration of the user.

6. The method of claim 1, further comprising: recording an earlier exercise motion by the user; and using the earlier exercise motion to create the baseline data.

7. The method of claim 1 further comprising: recording an earlier exercise motion by another user; and using the earlier exercise motion to create the baseline data.

8. The method of claim 1 further comprising: recording a plurality of exercise motions by a plurality of users; and aggregating the plurality of recorded exercise motions to produce the baseline.

9. The method of claim 1 further comprising creating the baseline using one or more ideal performance characteristics.

10. The method of claim 1, wherein identifying the motion deficiency further comprises comparing a first parameter of the detected exercise motion to a second parameter of the detected exercise motion.

11. The method of claim 1, wherein identifying the motion deficiency further comprises determining a quality of motion of the exercise motion.

12. The method of claim 1, wherein identifying the motion deficiency further comprises determining symmetry of the detected exercise motion.

13. The method of claim 1, wherein identifying the motion deficiency further comprises determining a load balance of the detected exercise motion.

14. The method of claim 1, wherein identifying the motion deficiency further comprises determining strength of the user based on the detected exercise motion.

15. The method of claim 1, wherein formulating the corrective motion further comprises creating a user baseline using the detected exercise motion.

16. The method of claim 15 wherein the recorded exercise motion is a first exercise motion, and further comprising: recording at least one second exercise motion; and aggregating the first exercise motion and the at least one second exercise motion to create the user baseline.

17. The method of claim 15, wherein formulating the corrective motion further comprises requiring the user to match one or more parameters of the user baseline.

18. The method of claim 15, wherein formulating the corrective motion further comprises requiring the user to exceed one or more parameters of the user baseline.

19. The method of claim 15, wherein formulating the corrective motion further comprises periodically updating the user baseline based on at least one subsequent exercise motion.

20. The method of claim 1, wherein formulating the corrective motion further comprises creating a schedule for the user to follow.

21. The method of claim 1 further comprising tracking user performance of at least one corrective motion.

* * * * *